US008288525B2

(12) United States Patent
de Fougerolles et al.

(10) Patent No.: US 8,288,525 B2
(45) Date of Patent: Oct. 16, 2012

(54) COMPOSITIONS AND METHODS FOR INHIBITING EXPRESSION OF CD45 GENE

(75) Inventors: Antonin de Fougerolles, Brookline, MA (US); Pamela Tan, Kulmbach (DE); Anna Borodovsky, Cambridge, MA (US); Tatiana Novobrantseva, Wellesley, MA (US); Sina Bavari, Frederick, MD (US); Kelly Lyn Warfield, Adamstown, MD (US)

(73) Assignee: Alnylam Pharmaceuticals, Inc., Cambridge, MA (US)

(*) Notice: Subject to any disclaimer, the term of this patent is extended or adjusted under 35 U.S.C. 154(b) by 0 days.

(21) Appl. No.: 12/867,230

(22) PCT Filed: Feb. 12, 2009

(86) PCT No.: PCT/US2009/033931
§ 371 (c)(1),
(2), (4) Date: Oct. 27, 2010

(87) PCT Pub. No.: WO2009/137128
PCT Pub. Date: Nov. 12, 2009

(65) Prior Publication Data
US 2011/0034537 A1    Feb. 10, 2011

Related U.S. Application Data

(60) Provisional application No. 61/028,162, filed on Feb. 12, 2008.

(51) Int. Cl.
*C12Q 1/68* (2006.01)
(52) U.S. Cl. .......... 536/24.5; 536/24.1; 536/24.31; 514/44; 435/6; 435/325; 435/375
(58) Field of Classification Search .......... None
See application file for complete search history.

(56) References Cited

U.S. PATENT DOCUMENTS

| | | | |
|---|---|---|---|
| 7,427,605 | B2 | 9/2008 | Davis et al. |
| 7,718,629 | B2 | 5/2010 | Bumcrot et al. |
| 2003/0143732 | A1 | 7/2003 | Fosnaugh et al. |
| 2003/0148519 | A1* | 8/2003 | Engelke et al. ......... 435/455 |
| 2003/0170891 | A1 | 9/2003 | McSwiggen |
| 2004/0259247 | A1 | 12/2004 | Tuschl et al. |
| 2006/0263435 | A1 | 11/2006 | Davis et al. |
| 2007/0004664 | A1 | 1/2007 | McSwiggen et al. |
| 2007/0031844 | A1 | 2/2007 | Khvorova et al. |
| 2007/0281899 | A1 | 12/2007 | Bumcrot et al. |
| 2009/0149403 | A1 | 6/2009 | MacLachlan |
| 2009/0247614 | A1* | 10/2009 | Manoharan et al. ....... 514/44 R |
| 2011/0015250 | A1 | 1/2011 | Bumcrot et al. |

FOREIGN PATENT DOCUMENTS

| | | |
|---|---|---|
| WO | WO 2004/080406 | 9/2004 |
| WO | WO 2004/090108 | 10/2004 |

OTHER PUBLICATIONS

Agrawal, S., et al., "Antisense oligonucleotides: towards clinical trials." Trends in Biotechnology. Oct. 1996, vol. 14, pp. 376-387.
Bass, B., "The short answer," Nature, May 24, 2001, pp. 428-429, vol. 411.
Elbashir, S., et al., "Analysis of gene function in somatic mammalian cells using small interfering RNAs," Methods, 2002, pp. 199-213, vol. 26.
Elbashir, S., et al., "Duplexes of 21-nucleotide RNAs mediate RNA interference in mammalian cell culture," Nature, May 24, 2001, p. 494-498, vol. 411.
Elbashir, S., et al., "Functional Anatomy of siRNAs for Mediating Efficient RNAi in Drosophila Melanogaster Embryo Lysate", The EMBO Journal, 2001, pp. 6877-6888, vol. 20, No. 23.
Elbashir, S., et al., "RNA Interference is Mediated by 21-and 22 Nucleotide RNAs," Genes & Development, 2001, pp. 188-200, vol. 15.
Fire, A., "RNA-triggered Gene Silencing," Trends in Genetics, Sep. 1999, pp. 358-363, vol. 15, No. 9.
Fire, A., et al., "Potent and Specific Genetic Interference by Double Stranded RNA in Caenorhabditis elegans," Nature, Feb. 19, 1998, pp. 806-811, vol. 391.
Tuschl, T., "Functional genomics: RNA sets the standard," Nature, Jan. 16, 2003, vol. 421, No. 6920, pp. 220-221.
Tuschl T., "RNA Interference and Small Interfering RNAs" Chembiochem, 2001, pp. 239-245, vol. 2.
Tuschl, T., et al., "Small Interfering RNAs: A Revolutionary Tool for the Analysis of Gene Function and Gene Therapy," Molecular Interventions, 2002, pp. 158-167, vol. 2, No. 3.
Tuschl, T., "Mammalian RNA Interference," RNAi, A Guide to Gene Silencing, Chapter 13, G.J. Hannon (ed,), 2003, pp. 265-295.
Tuschl, T., et al., "Targeted mRNA Degradation by Double-Stranded RNA in Vitro," Genes & Development, 1999, pp. 3191-3197, vol. 13.
Tuschl, T., "Expanding small RNA interference," Nature Biotechnology, May 2002, pp. 446-448, vol. 20.
Vickers, T., et al., "Efficient Reduction of Target RNAs by Small Interfering RNA and RNase H-dependent Antisense Agents," The Journal of Biological Chemistry, Feb. 28, 2003, pp. 7108-7118, vol. 278, No. 9.
Maurer, N., et al. "Spontaneous Entrapment of Polynucleotides Upon Electrostatic Interaction with Ethanol-Destabilized Cationic Liposomes," Biophysical Journal, May 2001, pp. 2310-2326, vol. 80.
Semple, S., et al., "Efficient Encapsulation of Antisense Oligonucleotides in Lipid Vesicles Using Ionizable Aminolipids: Formation of Novel Small Multilamellar Vesicle Structures," Biochim. Biophys. Acta., 2001, pp. 152-166, vol. 1510.
Anand, A.R., et al., "HIV-1, gp120-mediated apoptosis of T cells is regulated by the membrane tyrosine phosphatase CD45," Journal of Biological Chemistry, May 2006, pp. 12289-12299, vol. 281, No. 18.
Hermiston, M., et al., "CD45: a critical regulator of signaling thresholds in immune cells," Annual review of immunology, 2003, vol. 21, pp. 107-137.
Oliveira, D.M., et al., "Transient RNA interference in hematopoietic progenitors with functional consequences," Genesis, Aug. 2003, pp. 203-208, vol. 36, No. 4.
Tchilian, E., et al., "Altered CD45 expression and disease," Trends in immunology, Mar. 2006, pp. 146-153, vol. 27, No. 3.

(Continued)

*Primary Examiner* — Kimberly Chong
(74) *Attorney, Agent, or Firm* — Fenwick & West LLP

(57) ABSTRACT

The invention relates to a double-stranded ribonucleic acid (dsRNA) for inhibiting the expression of the CD45 gene.

14 Claims, 10 Drawing Sheets

OTHER PUBLICATIONS

PCT International Search Report and Written Opinion, PCT/US2009/033931, Jul. 1, 2010, 16 Pages.

Reynolds, et al. (2004) "Rational siRNA design for RNA interference," Nature Biotechnology, vol. 22, No. 3, pp. 326-330.

Robbins, M., et al., "Stable expression of shRNAs in human CD34+ progenitor cells can avoid induction of interferon responses to siRNAs in vitro," Nature Biotechnology, May 2006, pp. 566-571, vol. 24, No. 5.

Rose, S., et al., "Functional polarity is introduced by Dicer processing of short substrate RNAs," Nucleic Acids Research, 2005, pp. 4140-4156, vol. 33, No. 13.

Weil, et al (2002) "Targeting the Kinesin Eg5 to Monitor siRNA Transfection in Mammalian Cells," *Biotechniques* 33(6):1244-1248.

Zimmerman, et al. (2006) "RNAi-mediated gene silencing in non-human primates," *Nature*, vol. 441, May 4: 111-114.

Communication Pursuant to Article 94(3) EPC, mailed Jun. 1, 2011, for European Patent Application No. EP 09743115.9, 4 pages.

* cited by examiner

FIG. 5A

```
   1 agtattttg gagaagttag taaaaccgaa tctgacatca tcacctagca gttcatgcag
  61 ctagcaagtg gtttgttctt agggtaacag aggaggaaat tgttcctcgt ctgataagac
 121 aacagtggag aaaggacgca tgctgtttct tagggacacg gctgacttcc agatatgacc
 181 atgtatttgt ggcttaaact cttggcattt ggctttgcct ttctggacac agaagtattt
 241 gtgacagggc aaagcccaac accttcccc actggattga ctacagcaaa gatgcccagt
 301 gttccacttt caagtgaccc cttacctact cacaccactg cattctcacc cgcaagcacc
 361 tttgaaagag aaaatgactt ctcagagacc acaacttctc ttagtccaga caatacttcc
 421 acccaagtat ccccggactc tttggataat gctagtgctt taataccac aggtgtttca
 481 tcagtacaga cgcctcacct tcccacgcac gcagactcgc agacgccctc tgctggaact
 541 gacacgcaga cattcagcgg ctccgccgcc aatgcaaaac tcaaccctac cccaggcagc
 601 aatgctatct cagatgtccc aggagagagg agtacagcca gcacctttcc tacagaccca
 661 gtttccccat tgacaaccac cctcagcctt gcacaccaca gctctgctgc cttacctgca
 721 cgcacctcca acaccaccat cacagcgaac acctcagatg cctaccttaa tgcctctgaa
 781 acaaccactc tgagcccttc tggaagcgct gtcatttcaa ccacaacaat agctactact
 841 ccatctaagc caacatgtga tgaaaaatat gcaaacatca ctgtggatta cttatataac
 901 aaggaaacta aattatttac agcaaagcta aatgttaatg agaatgtgga atgtggaaac
 961 aatacttgca caaacaatga ggtgcataac cttacagaat gtaaaaatgc gtctgtttcc
1021 atatctcata attcatgtac tgctcctgat aagacattaa tattagatgt gccaccaggg
1081 gttgaaaagt ttcagttaca tgattgtaca caagttgaaa agcagatac tactatttgt
1141 ttaaaatgga aaaatattga aacctttact tgtgatacac agaatattac ctacagattt
1201 cagtgtggta atatgatatt tgataataaa gaaattaaat tagaaaacct tgaacccgaa
1261 catgagtata agtgtgactc agaaatactc tataataacc acaagtttac taacgcaagt
1321 aaaattatta aaacagattt tgggagtcca ggagagcctc agattatttt ttgtagaagt
1381 gaagctgcac atcaaggagt aattacctgg aatccccctc aaagatcatt tcataatttt
1441 accctctgtt atataaaaga gacagaaaaa gattgcctca atctggataa aaacctgatc
1501 aaatatgatt tgcaaaattt aaaaccttat acgaaatatg ttttatcatt acatgcctac
1561 atcattgcaa aagtgcaacg taatggaagt gctgcaatgt gtcatttcac aactaaaagt
1621 gctcctccaa gccaggtctg gaacatgact gtctccatga catcagataa tagtatgcat
1681 gtcaagtgta ggcctcccag ggaccgtaat ggcccccatg aacgttacca tttggaagtt
1741 gaagctggaa atactctggt tagaaatgag tcgcataaga attgcgattt ccgtgtaaaa
1801 gatcttcaat attcaacaga ctacactttt aaggccttt ttcacaatgg agactatcct
1861 ggagaaccct ttattttaca tcattcaaca tcttataatt ctaaggcact gatagcattt
1921 ctggcatttc tgattattgt gacatcaata gccctgcttg ttgttctcta caaatctat
1981 gatctacata agaaaagatc ctgcaattta gatgaacagc aggagcttgt tgaaagggat
2041 gatgaaaaac aactgatgaa tgtggagcca atccatgcag atattttgtt ggaaacttat
2101 aagaggaaga ttgctgatga aggaagactt tttctggctg aatttcagag catcccgcgg
2161 gtgttcagca gtttcctat aaaggaagct cgaaagccct taaccagaa taaaaaccgt
2221 tatgttgaca ttcttcctta tgattataac cgtgttgaac tctctgagat aaacggagat
2281 gcagggtcaa actacataaa tgccagctat attgatggtt caagaacc aggaaatac
2341 attgctgcac aaggtcccag ggatgaaact gttgatgatt tctggaggat gatttgggaa
2401 cagaaagcca cagttattgt catggtcact cgatgtgaag aaggaaacag gaacaagtgt
2461 gcagaatact ggccgtcaat ggaagagggc actcgggctt ttggagatgt tgttgtaaag
2521 atcaaccagc acaaaagatg tccagattac atcattcaga aattgaacat tgtaaataaa
2581 aagaaaaag caactggaag agaggtgact cacattcagt tcaccagctg gccagaccac
2641 ggggtgcctg aggatcctca cttgctcctc aaactgagaa ggagagtgaa tgccttcagc
```

FIG. 5B

```
2701 aatttcttca gtggtcccat tgtggtgcac tgcagtgctg gtgttgggcg cacaggaacc
2761 tatatcggaa ttgatgccat gctagaaggc ctggaagccg agaacaaagt ggatgtttat
2821 ggttatgttg tcaagctaag gcgacagaga tgcctgatgg ttcaagtaga ggcccagtac
2881 atcttgatcc atcaggcttt ggtggaatac aatcagtttg gagaaacaga agtgaatttg
2941 tctgaattac atccatatct acataacatg aagaaaaggg atccacccag tgagccgtct
3001 ccactagagg ctgaattcca gagacttcct tcatatagga gctggaggac acagcacatt
3061 ggaaatcaag aagaaaataa aagtaaaaac aggaattcta atgtcatccc atatgactat
3121 aacagagtgc cacttaaaca tgagctggaa atgagtaaag agagtgagca tgattcagat
3181 gaatcctctg atgatgacag tgattcagag gaaccaagca aatacatcaa tgcatctttt
3241 ataatgagct actggaaacc tgaagtgatg attgctgctc agggaccact gaaggagacc
3301 attggtgact tttggcagat gatcttccaa agaaaagtca aagttattgt tatgctgaca
3361 gaactgaaac atggagacca ggaaatctgt gctcagtact ggggagaagg aaagcaaaca
3421 tatggagata ttgaagttga cctgaaagac acagacaaat cttcaactta tacccttcgt
3481 gtctttgaac tgagacattc caagaggaaa gactctcgaa ctgtgtacca gtaccaatat
3541 acaaactgga gtgtggagca gcttcctgca gaacccaagg aattaatctc tatgattcag
3601 gtcgtcaaac aaaaacttcc ccagaagaat tcctctgaag ggaacaagca tcacaagagt
3661 acacctctac tcattcactg cagggatgga tctcagcaaa cgggaatatt ttgtgctttg
3721 ttaaatctct tagaaagtgc ggaaacagaa gaggtagtgg atattttca agtggtaaaa
3781 gctctacgca aagctaggcc aggcatggtt tccacattcg agcaatatca attcctatat
3841 gacgtcattg ccagcaccta ccctgctcag aatggacaag taaagaaaaa caaccatcaa
3901 gaagataaaa ttgaatttga taatgaagtg acaaagtaa agcaggatgc taattgtgtt
3961 aatccacttg gtgccccaga aaagctccct gaagcaaagg aacaggctga aggttctgaa
4021 cccacgagtg gcactgaggg gccagaacat tctgtcaatg gtcctgcaag tccagcttta
4081 aatcaaggtt cataggaaaa gacataaatg aggaaactcc aaacctcctg ttagctgtta
4141 tttctatttt tgtagaagta ggaagtgaaa ataggtatac agtggattaa ttaaatgcag
4201 cgaaccaata tttgtagaag ggttatattt tactactgtg gaaaaatatt taagatagtt
4261 ttgccagaac agtttgtaca gacgtatgct tattttaaaa ttttatctct tattcagtaa
4321 aaaacaactt ctttgtaatc gttatgtgtg tatatgtatg tgtgtatggg tgtgtgtttg
4381 tgtgagagac agagaaagag agagaattct ttcaagtgaa tctaaaagct tttgcttttc
4441 ctttgttttt atgaagaaaa aatacatttt atattagaag tgttaactta gcttgaagga
4501 tctgttttta aaaatcataa actgtgtgca gactcaataa aatcatgtac atttctgaaa
4561 tgacctcaag atgtcctcct tgttctactc atatatatct atcttatata gtttactatt
4621 ttacttctag agatagtaca taaggtggt atgtgtgtgt atgctactac aaaaaagttg
4681 ttaactaaat taacattggg aaatcttata ttccatatat tagcatttag tccaatgtct
4741 ttttaagctt atttaattaa aaaatttcca gtgagcttat catgctgtct ttacatgggg
4801 ttttcaattt tgcatgctcg attattccct gtacaatatt taaaatttat tgcttgatac
4861 ttttgacaac aaattaggtt ttgtacaatt gaacttaaat aaatgtcatt aaaataaata
4921 aatgcaatat gtattaatat tcattgtata aaaatagaag aatacaaaca tatttgttaa
4981 atatttacat atgaaattta atatagctat ttttatggaa ttttttcattg atatgaaaaa
5041 tatgatattg catatgcata gttcccatgt taaatcccat tcataacttt cattaaagca
5101 tttactttga atttctccaa tgcttagaat gttttacca ggaatggatg tcgctaatca
5161 taataaaatt caaccattat ttttttcttg tttataatac attgtgttat atgttcaaat
5221 atgaaatgtg tatgcaccta ttgaaatatg tttaatgcat ttattaacat tgcaggaca
5281 cttttacagg ccccaattat ccaatagtct aataattgtt taagatctag
```

FIG. 6A

```
   1 gacatcacca tttagcagtg catgtagcta gcaagtggtt tgttcttagg gtaagagagt
  61 aggaaacttg ctccccatct gataagacag agtgcaaagg agaccctatt tcttaggggc
 121 acagctgatc tccagatatg accatgggtt tgtggctcaa acttctggcc tttggatttg
 181 cccttctgga cacagaagtc tttgtcacag ggcaaacacc tacacccagt gatggtgcca
 241 gcctcacaac tcttacacca tccactctgg gccttgcaag cactgaccct ccaagcacaa
 301 ccatagctac cacaacgaag caaacatgtg ctgccatgtt tgggaacatt actgtgaatt
 361 acacctatga atctagtaat cagacttta aggcagacct caaagatgtc caaaatgcta
 421 agtgtggaaa tgaggattgt gaaaacgtgt taaataatct agaagaatgc tcacagataa
 481 aaaacatcag tgtgtctaat gactcatgtg ctccagctac aactatagat ttatatgtac
 541 caccagggac tgacaagttt tcgctacatg actgcacacc aaaagaaaag gctaatactt
 601 caatttgttt ggagtggaaa acaaaaaacc ttgatttcag aaaatgcaac agtgacaata
 661 tttcatatgt actccactgt gagccagaaa ataatacaaa atgcattaga agaaatacat
 721 tcatacctga aagatgtcag ttggacaacc ttcgtgccca aacaaattac acatgtgtag
 781 cagaaatctt atatcgcggt gtaaaactcg tcaaaaatgt tataaatgtg cagacagatt
 841 tggggattcc agaaacgcct aagcctagtt gtggggatcc agctgcaaga aaaacgttag
 901 tctcttggcc tgagcctgta tctaaacctg agtctgcatc taaaccccat ggatatgttt
 961 tatgctataa gaacaattca gaaaatgta aagtttgcc taataatgtg accagttttg
1021 aggtggaaag cttgaaacct tataaatact atgaagtgtc cctacttgcc tatgtcaatg
1081 ggaagattca agaaatggg actgctgaga agtgcaattt tcacacaaaa gcagatcgtc
1141 cggacaaggt caatggaatg aaaacctccc ggccgacaga caatagtata aatgttacat
1201 gtggtcctcc ttatgaaact aatggcccta aaaccttta cattttggta gtcagaagtg
1261 gaggttcttt tgttacaaaa tacaacaaga caaactgtca gttttatgta gataatctct
1321 actattcaac tgactatgag tttctggtct cttttcacaa tggagtgtac gagggagatt
1381 cagttataag aaatgagtca acaaatttta atgctaaagc actgattata ttcctggtgt
1441 ttctgattat tgtgacatca atagccttgc ttgttgtttt gtataaaatc tatgatctgc
1501 gcaagaaaag atccagcaat ttagatgaac aacaggaact cgttgaaagg gatgatgaaa
1561 agcagctgat ggatgtggag ccaatccatt ctgacatttt gttggaaaca tacaaaagga
1621 agattgctga tgagggcaga ctgttcctgg ctgaatttca gagcattcca cgggtattca
1681 gcaagtttcc catcaaagat gcccgaaagc cccacaatca gaataaaaac cgttatgttg
1741 acattcttcc ctatgattat aaccgtgtgg aactctctga ataaatgga gatgcagggt
1801 ccacctacat aaatgccagc tacattgatg gcttcaagga acccaggaaa tacattgctg
1861 cacaagggcc ccgggatgag acagttgatg acttctggag gatgatctgg gagcaaaagg
1921 ccacagttat tgtcatggtc acacgatgtg aagaaggaaa caggaacaag tgcgcagaat
1981 actggccaag catggaggaa ggcactcggg cttcaaaga tattgttgtg acaatcaatg
2041 accacaaacg atgtcctgat tacatcattc agaagctgaa cgttgcacat aaaaaagaaa
2101 aagcaactgg aagagaagtg actcatatcc aattccaccag ctggccagac catggggttc
2161 ctgaagaccc tcacctgctc tcaaacttc gacggagagt taatgctttt agcaacttct
2221 tcagtggtcc cattgtggtg cactgcagtg ctggtgttgg gcgtacaggt acctacattg
2281 gaattgatgc catgctggaa ggcctggaag cagagggcaa agtggatgtc tatggttatg
2341 ttgtcaagct aaggcgacag aggtgtctga tggtgcaagt ggaggcacag tatatcctga
2401 ttcatcaggc tttagtggaa tacaatcagt tggagaaac agaagtgaac ttgtctgagt
2461 tacattcatg cctacacaac atgaagaaga gagatccacc cagtgacccc tcccctctgg
2521 aggctgaata ccagagactt ccttcataca ggagttggag gacacagcac attggaaatc
```

FIG. 6B

```
2581 aagaagaaaa taagaagaag aacaggaatt ctaatgttgt tccatatgac tttaacagag
2641 tgccacttaa gcatgaactg gagatgagca aagagagtga gcctgaatca gatgagtctt
2701 cagatgatga cagtgactca gaagaaacca gcaaatacat taatgcatcc tttgtgatga
2761 gttactggaa accagaaatg atgattgctg ctcagggcc actaaaagaa acgatcggtg
2821 acttttggca gatgatattc caaagaaaag tcaaagttat tgtgatgttg acagagttag
2881 tgaatggaga ccaggaagtc tgtgctcagt actggggcga aggaaagcag acttatggag
2941 acatggaagt ggagatgaaa gacacaaaca gagcctcagc ctacactctc cgaacttttg
3001 agctgagaca ttccaagagg aaggagccca gaactgtgta ccagtaccag tgtaccacat
3061 ggaaagggga agagctgcct gcagaaccca agacctggt gtctatgatt caggacctca
3121 aacagaagct tcccaaggct tccccagaag ggatgaagta tcacaagcat gcatccatcc
3181 tcgtccactg cagagatgga tcccagcaga cagggttgtt ctgtgccttg ttcaatctct
3241 tggaaagtgc agaaacagaa gatgtggttg atgttttcca agtggtaaag tctctacgca
3301 aagcacggcc tggggtggtg tgcagctatg agcaatacca gttcctctat gacatcatcg
3361 ccagcatcta tcccgcccag aatggacaag tcaagaaaac aaacagccaa gacaaaattg
3421 aatttcataa tgaagtggat ggaggcaagc aggatgctaa ctgtgtccgt ccagatggtc
3481 ctctgaataa agcccaggaa gacagcagag gggtgggaac cccggagcct accaatagtg
3541 ctgaggaacc agaacatgct gccaatggtt ctgcgagccc agctccaacc cagagttcat
3601 aggaaaggag tcatgtggga caacgcagac tctcacatta gttctttcta ttttctaga
3661 cctaatgaaa gaacatggct gtgcagtggt ttatggaatc tgtgttcacc tttgccactg
3721 tataaaaata tttaagtttg tcaaaacatt ttgtacagtt ttatgcttat tttaaaagtg
3781 tatctatgtc attcagcagg aatgtatatg tgagagaggg tgtctgtgtg tgtgagagtg
3841 tgtttatgta tgagtgactg tgtgtgtgca tgtttgtgcg tgtgtatgac atctaaatgt
3901 gattggagaa tactttcaag ccatttcaaa tgcttcgag aaacagtgtg ccttttctcc
3961 tcttgaggaa actatacatt ttatatctaa actgttaatt tgtttgaggg attaattttt
4021 taaaatccca ttgaaagtgg attcagttgt aagaataaca atgtgtacca ttctggaatg
4081 acctcaaggt gtcctccttg tcctgttgat gatcttgtag tttaagatgc tcttttgga
4141 tatagataag cgtatgtaag agtgctgtgg gtgtgtacag ctgatctggg acgtgaacaa
4201 aatcaacatg tgagacttat gttccatata ctgtcatttc atcactatct cttaatgcat
4261 atttaatcaa acatgaaaat ctcaagggag actattttg tatccacatg ggaagtagaa
4321 cattgcaagt cagttgctgt ctacacaata gataaaaatt actagttaat gctcttggtc
4381 atatcgatat atgctatgaa cctaaataat tgcccttagc caaatataat gtatgttaaa
4441 aacacataga ataaaaacag gggcatgaaa acttgtttgt actgaatatt tacataggta
4501 acctcgtaca gttagttctg ttatggaatt caccatttat gggaaatgta aaattgacta
4561 tggccatttc ctatgcttaa gaccatcttt gacttgcatt actgtgtatt tatcttgaat
4621 ttccccactg ttttgtttac tcttactgag atataatatt gataaccata ataaactttc
4681 aactattatc ttctttgctt atgtggcgtg tgttacatgt ttgtaattga cagtgaagca
4741 atttcttctt caagctgaga ttggttttcc cattttgttc attgatgaga aaaatgaata
4801 attatcagat aggcgcatca gaagggata aagaggactc tgttttctca ctagccactc
4861 acagatttct atctcatgtc atctgggaaa ggttctgttg ctctttgctg gaaaacattg
4921 tggaagtttg cagttctgat gctgatgtac cttcaggctg gttttatgt tgatttgtga
4981 tttgtgattt gcttcagaat gctgatcatc ttcaatgata tcttttggaa cacagtttac
5041 ttagtagctg tttacttagc agcacatttg caacagcatc aaaagctatg ttactataaa
5101 atcagtgcgt gaagtctgat ttacattttg ctcaaggatc tgggtaaagt tttctaccaa
5161 gaatgttgag gactcatgaa aatgtgaagt tctccaactt ctaaaatttt ttaggacttt
5221 caataaacta taaaattatt caaaatc
```

FIG. 7A

```
   1 atgaccatgt gtttgtggct taaacttttg gcatttgtct ttgcctttct ggacacagaa
  61 gtatttgtga cagggcaagg ctcaacactt tcccccactg gctgtctgca agctgaggag
 121 caaggaagcc aatcggagtc ccaaaacctc aaaagcaggg aagctgacag tgcagcctca
 181 gtcagtggcc aaaggcctga gaaccctggc aaatcactgg agacggagaa cgacaaagat
 241 gcccagtgtt ccactttcaa gtgacccctt acctactcac accactgcat tctcacccgc
 301 aagcatctct gaaagagaaa atgacttctc agagaccaca ccatctctta gttcagacaa
 361 tacttcaacc cacgtatccc cggactcttt ggataacgct agtgctttta atacgacagg
 421 tgtttcatca gcactgacgc ctcaccttcc cacgcatgca gactcgcaga cgccctctac
 481 tggaactgac acgcagacac ccagcggctc cgccgccaat accacactca gccctacccc
 541 acgcagcaat gatatctcag atgtcccagg agagaggagt acagccagca cctttcctac
 601 agacccaatt tccccattag caaccaccct catccctgca cgcaacagct ctgctgcctt
 661 acctgcacgc acctccaaca ccaccatcac agcgaacacc tcagtttcct accttaatgc
 721 ctctgaaaca accactccga gcccttctgg aagcactgtc atttcaaccc caacaatagc
 781 tactactaca tctaagccaa catgtgctga aaaatatgca accatccctg tggattactt
 841 atataacaac aaaactaaat tatttacagc aaagctaaat gttaatgaga atgtggaatg
 901 tacaaacaat aatcacacac acaatatttg cacaaacaat gaggtgctta atcttccaga
 961 atgtaaagaa atgaatgttt tcgtatctca taattcatgt acagatcgtc ataaagaatt
1021 aaaattagat gtgccaccag aggttgaaaa gtttcagtta gatgattgta caccggatgt
1081 agaagcaaat accactattt gtttaaaatg gaaaattatt gaacctttg cttgtgataa
1141 aagtaaaatt acctacagat tcaatgtgg taataaaaca taataagg aaggcattta
1201 tttagaaaac cttgaacctg aatatgagta taagtgtgac tcagaaatac tctataataa
1261 ccacaagtat attaacataa ccaaacttat aaaaacagat tttgggattc caggacagcc
1321 tcagaatgtt gtttgtagac atgaagatgc acatcaagga gtaattacct ggaatccccc
1381 tcaaagatca tttcataatt ttactctctg ttatgtaagc aagacagcaa aaaaatgcct
1441 cagtctggat aaacacctga caacatatca tttgcaaaat ttgaaccctt atacaaacta
1501 tagtttatca ttacatgcct acatcattgc aaaagtgcaa cgtaatgaaa ctgctgcaac
1561 atgtaatttc acaactgaaa gtgcacctcc aagccaggtc cagaacatga ttgtctccac
1621 atcagataat agtatgcgtg tcaagtgtga gggtcccagg gacgttaatg gccccactgg
1681 actttaccat ctggaagtcg aagctggaaa tactctagtt agaaatctgt cacaatctaa
1741 gtgcgatttc tctgtaaaca atcttcaata ttcaacatac tacaatctta aggtaaaagt
1801 atgctctcta cattactata gtaccaacat acatgataat gattgattca tattcatata
1861 tagcactccc tataattcta aggcactgat agcatttctg gcatttctga ttattgtgac
1921 atcaatagcc ctacttgttg ttctctataa aatctatgat ctacataaga aaagatcctg
1981 caatttggat gaacaacagg agcttgttga agggatgat gaaaacaac tgatgaatgt
2041 ggagccaatc catgcagata ttttgttgga aacttataag aggaagattg ctgatgaagg
2101 aagactttt ctggctgaat tcagagcat cccgcgggtg ttcagcaagt ttcctataaa
2161 ggaagctcga aagcccttta accagaataa aaaccgttat gttgacattc ttccttatga
2221 ttataaccgt gttgaactct ctgagataaa tggagatgca gggtcaaact acataaatgc
2281 cagctatatt gatggtttca agaacccag gaaatacatt gctgcacaag gtcccaggga
2341 tgaaaccgtt gatgatttct ggaggatgat tgggaacag aaagccacag ttattgtcat
2401 ggtcactcga tgtgaagaag aaacaggaa caagtgtgca gaatactggc cgtcaatgga
2461 agagggcact cgggcttttg gagatgttgt tgtaaagatc aaccagcaca aaagatgtcc
2521 agattacatc attcagaaat tgaacattgt aaataaaaaa gaaaagcaa ctggaagaga
2581 ggtgactcac attcagttta ccagctggcc agaccacggg gtgcctgagg atcctcactt
```

FIG. 7B

```
2641 gctcctcaaa ctgagaagga gagtgaatgc cttcagcaat ttcttcagtg gtcccattgt
2701 ggtgcactgc agtgctggtg tcgggcgcac aggcacctat attggaattg atgccatgct
2761 agaaggcctg gaagctgaga acaaagtaga tgtttatggt tacgttgtca agctaaggcg
2821 acagagatgc ctgatggttc aagtagaggc ccagtacatc ttgatccatc aggctttggt
2881 tgaatacaat cagtttggag aaacagaagt gaatttgtct gaattacatc catatctaca
2941 taacatgaag aaaagggatc cacccagtga gccatctcca ctagaggctg aattccagag
3001 acttccttca tataggagct ggaggacaca gcacattgga aatcaggaag aaaataaaaa
3061 taaaaacagg aattctaatg tcatcccata tgactataac agagtgccac ttaaacatga
3121 gctggaaatg agtaaagaga gtgaccatga ttcagatgaa tcctctgatg atgacagtga
3181 ttcagaggaa ccaagcaaat acatcaatgc atctttata atgagctact ggaaacctga
3241 agtgatgatt gctgctcagg gaccactgaa ggagaccatt ggtgactttt ggcagatgat
3301 cttccaaaga aaagtcaaag ttattgttat gctgacagaa ctgaaacacg agaccagga
3361 aatctgtgct cagtactggg gagaaggaaa gcaaacatat ggagatatcg aagttgacat
3421 gaaagacaca aacaaatctt caacttacac ccttcgtgtc tttgaactga gacattccaa
3481 gaggaaagac tctcgaactg tgtaccagta ccaatataca aactggagtg tggagcagct
3541 tcctgcagaa cccaaggaat tagtctctct gattcaggtc ctcaaagaaa acttcccca
3601 gaagaattcc tccgaaggga acaagcatca caagagtaca cctctcctca ttcactgcag
3661 ggatggatct cagcaaacgg gaatattttg tgctttgtta aatctcttag aaagtgcgga
3721 aacagaagag gtagtggata ttttcaagt ggtaaaagct ctacgcaaag ctaggcctgg
3781 catggtttcc acatttgagc aataccaatt cctatatgac atcattgcca gcacctaccc
3841 tgctcagaat ggacaagtaa agaaaaacaa ccatcaagaa gataaaattg aatttgataa
3901 tgaagtggac aaagtaaagc aggatgctaa ttgtgttaat ccacttggtg ccacagaaaa
3961 gctccctgaa gcaaaggaac aggctacagg ttctgaaccc acaagtggca ctgaggggcc
4021 agaacattct gtcaatggtc ctgcaagtcc agctttaaat caaggttcat aggaaaagac
4081 ataaatgggg aaactccaaa cctcctgtta gctgttattt ctattttct agaagtagga
4141 agtgaaaata gtatacagtg gattaattaa atgtattgaa ccaatatttg tggaagggtt
4201 ctattttact actgtggaaa aatatttaag atagttttgc cagaacagtt tgtacagacg
4261 tatgcttatt ttaaaatttt atttcttatt cagtaagaaa caacttcttt gtaaccttta
4321 catgtgtatg tatatgtgtg tatgcgtgtg tttgtgtgag agagaaagag aattctttca
4381 agtgaatcta aaagcttttg ctttgccttt ttgtttttat caagaaaaaa tacattttat
4441 attagaagtg tttacttagc ttgaaggatc tgttttaaa atcataaact gtgtgcagac
4501 tataaaatca tgtacatttc taaaatgacc tcaagatgtc ctccttgttc tactcatata
4561 tatcttatat atcttatata gttccagatt ttacttctag agatagtaca taaagtggt
4621 atgtgtgtgt atagctacta caaaacagtt aactaaatta acatttggaa atcttatatt
4681 ccatatatta tcatttaatc caatatcttt ttaagcttat ttaattaaaa aatttccagt
4741 gagcttatct ggctgtcttt acatggggtt tacaattttt tatcatctat tattccctgt
4801 acaatattta aaatttattg cttgatactt ttgaccacga attatgtttt gtacaattga
4861 acttaaataa acgtcattaa aataaaccaa tgcaatatgt attaatattc attgtataaa
4921 aataaaaaaa tacaaatata tttgttaaat gtttacatat gaatttaac atagctattt
4981 ttatggaatt tttcattgat atgaaaaata taatattgca tatgcatagg tctcatgtta
5041 aataccattc ataactttca ttaaagcatt tactttgaac ttctccaatg cttagattct
5101 ttttaccggg aatggatatc actaatcata ataaaattca acgatttttt ttcttgttt
5161 ataatacatt gtgttatatg ttcaaatctg aaatgtgtat gcacctgttg aaatatgttt
5221 aatgcagtta ttaacatttg cagaacaatt ttacaggccc cagttatcca atagtctaat
5281 aattgtttaa gatctagaaa aaaatcaaga atagtggtat gtttcatgaa gtaataaaaa
       5341 ctcattttca tgaa
```

COMPOSITIONS AND METHODS FOR INHIBITING EXPRESSION OF CD45 GENE

CROSS-REFERENCE TO RELATED APPLICATIONS

This application claims priority to U.S. Application Ser. No. 61/028,162, filed Feb. 12, 2008. The entire contents of the provisional application are hereby incorporated by reference in the present application.

Sequence Listing

The instant application contains a Sequence Listing which has been submitted via EFS-Web and is hereby incorporated by reference in its entirety. Said ASCII copy, created on Aug. 5, 2010, is named 15491US CRF sequencelisting.txt and is 126,484 bytes in size.

Government Support

This invention was made with government support under HDTRA1-07-C-0082 awarded by the Defense/Defense Threat Reduction Agency, and HHSN266200600012C awarded by the Department of Health and Human Services/ NIH/NAIAD. The government has certain rights in the invention.

FIELD OF THE INVENTION

This invention relates to double-stranded ribonucleic acid (dsRNA), and its use in mediating RNA interference to inhibit the expression of the CD45 gene and the use of the dsRNA to treat infectious diseases and autoimmune disease.

BACKGROUND OF THE INVENTION

CD45 is a hematopoietic cell-specific transmembrane protein tyrosine phosphatase essential for T and B cell antigen receptor-mediated signaling and also plays a important role in cytokine receptor signaling, chemokine and cytokine response and apoptosis regulation in multiple different leukocyte cell subsets (T cells, B cells, NK cells, myeloid cells, granulocytes, and dendritic cells). CD45 constitutes nearly 10% of T and B cell surface protein. The protein includes a large extracellular domain, and a phosphatase containing cytosolic domain. CD45 may act as both a positive and negative regulator depending on the nature of the stimulus and the cell type involved. CD45 RNA transcripts are alternatively spliced at the N-terminus, which results in extracellular domains of various sizes. The protein controls the activity of Src-family kinases, which if left unregulated, can cause cancer and autoimmunity. Mice and humans lacking CD45 expression have been shown to be immunodeficient.

Multiple human or rodent mutations that result in altered CD45 expression or functional activity are associated with distinct malignancies, including autoimmunity, immunodeficiency, overt activation of T cells, susceptibility to infection, type I or type II associated immune disorders, and haemotologic malignancies (reviewed in Tchilian and Beverly, Trends in Immunology, 2006).

Double-stranded RNA molecules (dsRNA) have been shown to block gene expression in a highly conserved regulatory mechanism known as RNA interference (RNAi). WO 99/32619 (Fire et al.) discloses the use of a dsRNA of at least 25 nucleotides in length to inhibit the expression of the unc-22 gene in C. elegans. dsRNA has also been shown to degrade target RNA in other organisms, including plants (see, e.g., WO 99/53050, Waterhouse et al.; and WO 99/61631, Heifetz et al.), Drosophila (see, e.g., Yang, D., et al., Curr. Biol. (2000) 10:1191-1200), and mammals (see WO 00/44895, Limmer; and DE 101 00 586.5, Kreutzer et al.).

SUMMARY OF THE INVENTION

The invention provides double-stranded ribonucleic acid (dsRNA), as well as compositions and methods for inhibiting the expression of the CD45 gene in a cell or mammal using such dsRNA. The invention also provides compositions and methods for treating pathological conditions and diseases caused by the expression of the CD45 gene, such as infectious disease and autoimmune disease. The dsRNA featured in the invention includes an RNA strand (the antisense strand) having a region which is less than 30 nucleotides in length, generally 19-24 nucleotides in length, and which is substantially complementary or fully complementary to the corresponding region of an mRNA transcript of the CD45 gene.

In one aspect, the invention features, double-stranded ribonucleic acid (dsRNA) molecules for inhibiting the expression of the CD45 gene. The dsRNA includes at least two sequences that are complementary, e.g., substantially or fully complementary, to each other. The dsRNA includes a sense strand including a first sequence and an antisense strand including a second sequence. The antisense strand includes a nucleotide sequence which is substantially or fully complementary to the corresponding region of an mRNA encoding CD45, and the region of complementarity is less than 30 nucleotides in length, generally 19-24 nucleotides in length, e.g., 19 to 21 nucleotides in length. In some embodiments, the dsRNA is from about 10 to about 15 nucleotides, and in other embodiments the dsRNA is from about 25 to about 30 nucleotides in length. In another embodiment, the dsRNA is at least 15 nucleotides in length. The dsRNA, upon contacting with a cell expressing the CD45, e.g., in an assay described herein, e.g., in a P388D1 cell assay as described herein (or an assay based on a cell with similar properties), inhibits the expression of the CD45 gene by at least 20% or 25%, and preferably by at least 35%, or preferably by at least 40%. In one embodiment, the CD45 dsRNA is formulated in a stable nucleic acid particle (SNALP).

The dsRNA molecules featured in the invention include dsRNAs that cleave a CD45 mRNA in a target sequence selected from the group consisting of SEQ ID NOs:97-144. The dsRNAs featured herein also include dsRNAs having a first sequence selected from the group consisting of the sense sequences of Tables 2, 4 and 5, and a second sequence selected from the group consisting of the antisense sequences of Tables 2, 4 and 5. The dsRNA molecules featured in the invention can include naturally occurring nucleotides or can included at least one modified nucleotide, such as a 2'-O-methyl modified nucleotide, a nucleotide including a 5'-phosphorothioate group, and a terminal nucleotide linked to a cholesteryl derivative or dodecanoic acid bisdecylamide group. Alternatively, the modified nucleotide may be chosen from the group of: a 2'-deoxy-2'-fluoro modified nucleotide, a 2'-deoxy-modified nucleotide, a locked nucleotide, an abasic nucleotide, 2'-amino-modified nucleotide, 2'-alkyl-modified nucleotide, morpholino nucleotide, a phosphoramidate, and a non-natural base comprising nucleotide. Generally, the first sequence of the dsRNA is selected from the group consisting of the sense sequences of Tables 2, 4 and 5, and the second sequence is selected from the group consisting of the antisense sequences of Tables 2, 4 and 5.

In another aspect, the invention provides a cell including a dsRNA targeting CD45. The cell can be a mammalian cell, such as a human cell.

In another aspect, the invention features a pharmaceutical composition containing a dsRNA, such as a dsRNA described herein, e.g., in Tables 2, 4 and 5, and a pharmaceutically acceptable carrier. In one embodiment, the pharmaceutical composition does not include another agent that silences gene expression. In another embodiment, the pharmaceutical composition does not include another dsRNA, e.g., a dsRNA of a length or overhang structure described herein. In another embodiment, the pharamaceutical composition consists of or consists essentially of the subject dsRNA. In another embodiment, the pharmaceutical composition includes more than one dsRNA. In yet other embodiments, the pharmaceutical composition includes more than one but not more than 2, 3 or 4 dsRNAs.

In another aspect, the invention provides a method for inhibiting the expression of the CD45 gene in a cell, including the following steps:
  (a) introducing into the cell a double-stranded ribonucleic acid (dsRNA), e.g., a dsRNA described herein, e.g., a dsRNA that cleaves a CD45 mRNA in a target sequence selected from the group consisting of SEQ ID NOs:97-144, wherein the dsRNA includes at least two sequences that are complementary, e.g., substantially or fully complementary, to each other. The dsRNA includes a sense strand including a first sequence and an antisense strand including a second sequence. The antisense strand includes a region of complementarity which is substantially or fully complementary to the corresponding region of an mRNA encoding CD45, and wherein the region of complementarity is less than 30 nucleotides in length, generally 19-24 nucleotides in length, and preferably, wherein the dsRNA, upon contact with a cell expressing the CD45, inhibits expression of the CD45 gene by at least 20%, at least 25%, or at least 40%; and
  (b) maintaining the cell produced in step (a) for a time sufficient to obtain degradation of the mRNA transcript of the CD45 gene, thereby inhibiting expression of the CD45 gene in the cell.

In another aspect, the invention provides methods for treating, preventing or managing infectious disease by administering to a patient in need of such treatment, prevention or management a therapeutically or prophylactically effective amount of one or more of the CD45 dsRNAs featured in the invention.

In another aspect, the invention provides methods for treating, preventing or managing autoimmune disease, including administering to a patient in need of such treatment, prevention or management a therapeutically or prophylactically effective amount of one or more of the CD45 dsRNAs featured in the invention.

In another aspect, the invention provides methods for treating, preventing or managing inflammation, including administering to a patient in need of such treatment, prevention or management a therapeutically or prophylactically effective amount of one or more of the CD45 dsRNAs featured in the invention.

In another aspect, the invention provides methods for treating, preventing or managing a viral infection, including administering to a patient in need of such treatment, prevention or management a therapeutically or prophylactically effective amount of one or more of the CD45 dsRNAs featured in the invention.

In another aspect, the invention provides vectors for inhibiting the expression of the CD45 gene in a cell, including a regulatory sequence operably linked to a nucleotide sequence that encodes at least one strand of one of the dsRNAs featured in the invention.

In another aspect, the invention provides a cell including a vector for inhibiting the expression of the CD45 gene in a cell. The vector includes a regulatory sequence operably linked to a nucleotide sequence that encodes at least one strand of one of the CD45 dsRNAs featured in the invention.

BRIEF DESCRIPTION OF THE FIGURES

FIG. 1A demonstrates reduction in CD45 protein expression following a single injection with 10 mg/kg formulated CD45 siRNA as compared to saline or irrelevant siRNA. FIG. 1B shows two independent dose response experiments demonstrating that substantial reduction in CD45 expression is seen in vivo following a single injection of 0.6-15 mg/kg formulated CD45 siRNA relative to irrelevant siRNA.

FIGS. 5A and 5B illustrate the sequence of human CD45 cDNA (SEQ ID NO:339) as recorded at GenBank Accession No. NM_002838.2 (version dated Jan. 13, 2008).

FIGS. 6A and 6B illustrate the sequence of mouse CD45 cDNA (SEQ ID NO:340) as recorded at GenBank Accession No. NM_011210 (version dated Jan. 27, 2008).

FIGS. 7A and 7B illustrate the sequence of rhesus CD45 cDNA (SEQ ID NO:341) as recorded at GenBank Accession No. XR_012672.1 (version dated Jun. 14, 2006).

DETAILED DESCRIPTION OF THE INVENTION

Figure 1A:
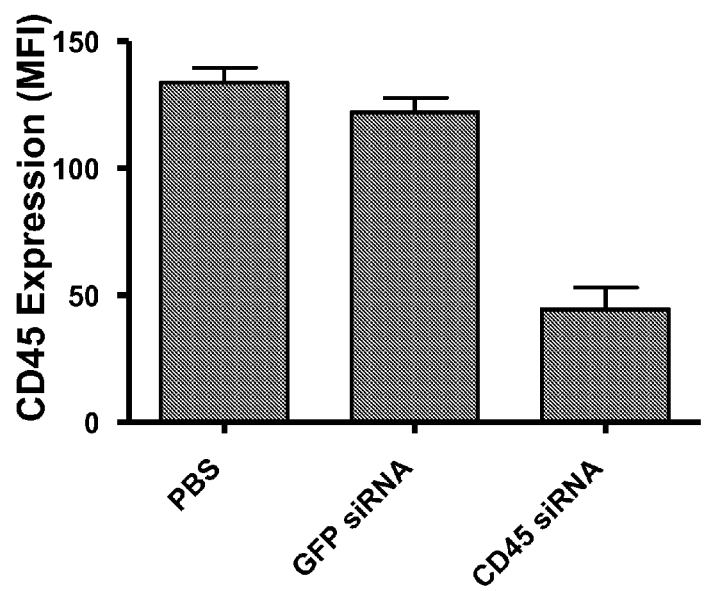
FIGS. 1A and 1B are graphs showing that a lipid-formulated dsRNA targeting CD45 delivered to mice intraperitoneally inhibited protein expression of CD45 in vivo in peritoneal macrophages as compared to an irrelevant similarly formulated dsRNA targeting GFP.

The invention provides double-stranded ribonucleic acid (dsRNA), as well as compositions and methods for inhibiting the expression of the CD45 gene in a cell or mammal using the dsRNA. The invention also provides compositions and methods for treating pathological conditions and diseases in a mammal caused by the expression of the CD45 gene using dsRNA. dsRNA directs the sequence-specific degradation of mRNA through a process known as RNA interference (RNAi). The process occurs in a wide variety of organisms, including mammals and other vertebrates.

The dsRNAs featured in the invention includes an RNA strand (the antisense strand) having a region which is less than 30 nucleotides in length, generally 19-24 nucleotides in length, and is substantially or fully complementary to at least part of an mRNA transcript of the CD45 gene. The use of these dsRNAs enables the targeted degradation of mRNAs of genes that are implicated in autoimmunity and infectious disease in mammals. Using cell-based and animal assays, the present inventors have demonstrated that very low dosages of these dsRNA can specifically and efficiently mediate RNAi, resulting in significant inhibition of expression of the CD45 gene. Thus, the methods and compositions featured in the invention including these dsRNAs are useful for treating autoimmunity and infectious disease.

The following detailed description discloses how to make and use the dsRNA and compositions containing dsRNA to inhibit the expression of a target CD45 gene, as well as compositions and methods for treating diseases and disorders caused by the expression of CD45, such as an infectious disease or autoimmune disease. The pharmaceutical compositions featured in the invention include a dsRNA having an antisense strand having a region of complementarity which is less than 30 nucleotides in length, generally 19-24 nucleotides in length, and is substantially complementary to at least part of an RNA transcript of the CD45 gene, together with a pharmaceutically acceptable carrier.

Accordingly, certain aspects featured in the invention provide pharmaceutical compositions including a dsRNA targeting CD45 together with a pharmaceutically acceptable carrier, methods of using the compositions to inhibit expression of the CD45 gene, and methods of using the pharmaceutical compositions to treat diseases caused by expression of the CD45 gene.

I. Definitions

For convenience, the meaning of certain terms and phrases used in the specification, examples, and appended claims, are provided below. If there is an apparent discrepancy between the usage of a term in other parts of this specification and its definition provided in this section, the definition in this section shall prevail.

"G," "C," "A," "T" and "U" each generally stand for a nucleotide that contains guanine, cytosine, adenine, thymidine and uracil as a base, respectively. However, it will be understood that the term "ribonucleotide" or "nucleotide" can also refer to a modified nucleotide, as further detailed below, or a surrogate replacement moiety. The skilled person is well aware that guanine, cytosine, adenine, thymidine and uracil may be replaced by other moieties without substantially altering the base pairing properties of an oligonucleotide including a nucleotide bearing such replacement moiety. For example, without limitation, a nucleotide including inosine as its base may base pair with nucleotides containing adenine, cytosine, or uracil. Hence, nucleotides containing uracil, guanine, or adenine may be replaced in the dsRNAs featured in the invention by a nucleotide containing, for example, inosine. In another example, adenine and cytosine anywhere in the oligonucleotide can be replaced with guanine and uracil, respectively to form G-U Wobble base pairing with the target mRNA. Sequences including such replacement moieties are embodiments featured in the invention.

By "CD45" as used herein is meant a CD45 mRNA, protein, peptide, or polypeptide. The term "CD45" is also known in the art as PTPRC (protein tyrosine phosphatase, receptor type, C), B220, GP180, LCA, LY5, and T200. The sequence of human CD45 cDNA is recorded at GenBank Accession No. NM_002838.2 (version dated Jan. 13, 2008) (see FIGS. 5A and 5B). Other human CD45 sequences are recorded at GenBank Accession Nos. NM_080921.2, NM_080922.2, NM_080923.2, Y00062.1, Y00638.1, BC014239.2, BC017863.1, BC031525.1, BC121086.1, BC121087.1, BC127656.1, BC127657.1, AY429565.1, AY567999.1, AK130573.1, DA670254.1, DA948670.1, AY429566.1, and CR621867.1. Mouse CD45 mRNA sequences are found at GenBank Accession Nos. NM_011210.2, AK054056.1, AK088215.1, AK154893.1, AK171802.1, BC028512.1, EF101553.1, L36091.1, M11934.1, M14342.1, M14343.1, M15174.1, M17320.1, and M92933.1. Rhesus monkey CD45 mRNA sequence are found at GenBank Accession No. XR_012672.1.

As used herein, "target sequence" refers to a contiguous portion of the nucleotide sequence of an mRNA molecule formed during the transcription of the CD45 gene, including mRNA that is a product of RNA processing of a primary transcription product.

As used herein, the term "strand including a sequence" refers to an oligonucleotide including a chain of nucleotides that is described by the sequence referred to using the standard nucleotide nomenclature.

The terms "complementary", "fully complementary" and "substantially complementary" herein may be used with respect to the base matching between the sense strand and the antisense strand of a dsRNA, or between the antisense strand of a dsRNA and a target sequence, as will be understood from the context of their use.

As used herein, and unless otherwise indicated, the term "complementary," when used to describe a first nucleotide sequence in relation to a second nucleotide sequence, refers to the ability of an oligonucleotide or polynucleotide including the first nucleotide sequence to hybridize and form a duplex structure under certain conditions with an oligonucleotide or polynucleotide including the second nucleotide sequence, as will be understood by the skilled person. Complimentary includes both fully complimentary and substantially complimentary states. Fully complimentary means comlimentary at each nucleotide pair of to compared sequences, e.g., an antisence strand and the corresponding portion of a target mRNA. For substantial complementarity, such conditions can, for example, be stringent conditions, where stringent conditions may include: 400 mM NaCl, 40 mM PIPES pH 6.4, 1 mM EDTA, 50° C. or 70° C. for 12-16 hours followed by washing. Other conditions, such as physiologically relevant conditions as may be encountered inside an organism, can apply. The skilled person will be able to determine the set of conditions most appropriate for a test of complementarity of two sequences in accordance with the ultimate application of the hybridized nucleotides. In other embodiments, substantial complimentarity can mean not more than 4, 3 or 2 mismatched base pairs upon hybridization, while retaining the ability to hybridize under the conditions most relevant to their ultimate application. Where two oligonucleotides are designed to form, upon hybridization, one or more single stranded overhangs, such overhangs shall not be regarded as mismatches with regard to the determination of complementarity. For example, a dsRNA including one oligonucleotide 21 nucleotides in length and another oligonucleotide 23 nucleotides in length, wherein the longer oligonucleotide includes a sequence of 21 nucleotides that is fully complementary to the shorter oligonucleotide, may yet be referred to as "fully complementary" for the purposes of the invention.

"Complementary" sequences, as used herein, may also include, or be formed entirely from, non-Watson-Crick base pairs and/or base pairs formed from non-natural and modified nucleotides, in as far as the above requirements with respect to their ability to hybridize are fulfilled. Such non-Watson-Crick base pairs includes, but not limited to, G:U Wobble or Hoogstein base pairing.

As used herein, a polynucleotide which is "substantially complementary to at least part of" a messenger RNA (mRNA) refers to a polynucleotide which is substantially complementary to a contiguous portion of the mRNA of interest (e.g., encoding CD45). For example, a polynucleotide is complementary to at least a part of a CD45 mRNA if the sequence is substantially complementary to a non-interrupted portion of an mRNA encoding CD45.

The term "double-stranded RNA" or "dsRNA", as used herein, refers to a ribonucleic acid molecule, or complex of ribonucleic acid molecules, having a duplex structure including two anti-parallel and substantially complementary, as defined above, nucleic acid strands. The two strands forming the duplex structure may be different portions of one larger RNA molecule, or they may be separate RNA molecules. Where the two strands are part of one larger molecule, and therefore are connected by an uninterrupted chain of nucleotides between the 3'-end of one strand and the 5' end of the respective other strand forming the duplex structure, the connecting RNA chain is referred to as a "hairpin loop". Where the two strands are connected covalently by means other than an uninterrupted chain of nucleotides between the 3'-end of one strand and the 5' end of the respective other strand forming the duplex structure, the connecting structure is referred to as a "linker." The RNA strands may have the same or a different number of nucleotides. The maximum number of base pairs is the number of nucleotides in the shortest strand of the dsRNA. In addition to the duplex structure, a dsRNA may comprise one or more nucleotide overhangs. A dsRNA as used herein is also referred to as a "small inhibitory RNA" or "siRNA."

As used herein, a "nucleotide overhang" refers to the unpaired nucleotide or nucleotides that protrude from the duplex structure of a dsRNA when a 3'-end of one strand of the dsRNA extends beyond the 5'-end of the other strand, or vice versa. "Blunt" or "blunt end" means that there are no unpaired nucleotides at that end of the dsRNA, i.e., no nucleotide overhang. A "blunt ended" dsRNA is a dsRNA that is double-stranded over its entire length, i.e., no nucleotide overhang at either end of the molecule.

The term "antisense strand" refers to the strand of a dsRNA which includes a region that is substantially complementary to the corresponding sequence of a target sequence. As used herein, the term "region of complementarity" refers to the region on the antisense strand that is substantially complementary to a sequence, for example a target sequence, as defined herein. Where the region of complementarity is not fully complementary to the target sequence, the mismatches may be in the internal or terminal regions of the molecule. Generally, the most tolerated mismatches are in the terminal regions, e.g., within 6, 5, 4, 3, or 2 nucleotides of the 5' and/or 3' terminus.

The term "sense strand," as used herein, refers to the strand of a dsRNA that includes a region that is substantially complementary to a region of the antisense strand.

The term "identity" is the relationship between two or more polynucleotide sequences, as determined by comparing the sequences. Identity also means the degree of sequence relatedness between polynucleotide sequences, as determined by the match between strings of such sequences. While there exist a number of methods to measure identity between two polynucleotide sequences, the term is well known to skilled artisans (see, e.g., Sequence Analysis in Molecular Biology, von Heinje, G., Academic Press (1987); and Sequence Analysis Primer, Gribskov, M. and Devereux, J., eds., M. Stockton Press, New York (1991)). "Substantially identical," as used herein, means there is a very high degree of homology (preferably 100% sequence identity) between the sense strand of the dsRNA and the corresponding part of the target gene. However, dsRNA having greater than 90% or 95% sequence identity may be used in the present invention, and thus sequence variations that might be expected due to genetic mutation, strain polymorphism, or evolutionary divergence can be tolerated. Although 100% identity is typical, the dsRNA may contain single or multiple base-pair random mismatches between the RNA and the target gene.

As used herein, the term "SNALP" refers to a stable nucleic acid-lipid particle. A SNALP represents a vesicle of lipids coating a reduced aqueous interior comprising a nucleic acid such as an iRNA agent or a plasmid from which an iRNA agent is transcribed. SNALPs are described, e.g., in U.S. Patent Application Publication Nos. 20060240093, 20070135372, and U.S. Ser. No. 61/045,228 filed Apr. 15, 2008. These applications are hereby incorporated by reference.

"Introducing into a cell," when referring to a dsRNA, means facilitating uptake or absorption into the cell, as is understood by those skilled in the art. Absorption or uptake of dsRNA can occur through unaided diffusive or active cellular processes, or by auxiliary agents or devices. The meaning of this term is not limited to cells in vitro; a dsRNA may also be "introduced into a cell," wherein the cell is part of a living organism. In such instance, introduction into the cell will include the delivery to the organism. For example, for in vivo delivery, dsRNA can be injected into a tissue site or administered systemically. In vivo delivery can also be by a beta-glucan delivery system, such as those described in U.S. Pat. Nos. 5,032,401 and 5,607,677, and U.S. Publication No. 2005/0281781. U.S. Pat. Nos. 5,032,401 and 5,607,677, and U.S. Publication No. 2005/0281781 are hereby incorporated by reference in their entirety. In vitro introduction into a cell includes methods known in the art such as electroporation and lipofection.

The terms "silence" and "inhibit the expression of," "down-regulate the expression of," "suppress the expression of," and the like, in as far as they refer to the CD45 gene, herein refer to the at least partial suppression of the expression of the CD45 gene, as manifested by a reduction of the amount of CD45 mRNA, which may be isolated from a first cell or group of cells in which the CD45 gene is transcribed, and which has or have been treated such that the expression of the CD45 gene is inhibited, as compared to a second cell or group of cells substantially identical to the first cell or group of cells but which has or have not been so treated (control cells). The degree of inhibition is usually expressed in terms of $$\frac{(mRNA \text{ in control cells}) - (mRNA \text{ in treated cells})}{(mRNA \text{ in control cells})} \cdot 100\%$$

Alternatively, the degree of inhibition may be given in terms of a reduction of a parameter that is functionally linked to CD45 gene expression, e.g. the amount of protein encoded by the CD45 gene which is present on the cell surface, or the number of cells displaying a certain phenotype, e.g apoptosis. In principle, CD45 gene silencing may be determined in any cell expressing the CD45, either constitutively or by genomic engineering, and by any appropriate assay. However, when a reference is needed in order to determine whether a given siRNA inhibits the expression of the CD45 gene by a certain degree and therefore is encompassed by the instant invention, the assays provided in the Examples below shall serve as such reference.

For example, in certain instances, expression of the CD45 gene is suppressed by at least about 20%, 25%, 30%, 35%, 40%, 45%, or 50% by administration of the double-stranded oligonucleotide featured in the invention. In one embodiment, the CD45 gene is suppressed by at least about 50%, 60%, or 70% by administration of the double-stranded oligonucleotide featured in the invention. In another embodiment, the CD45 gene is suppressed by at least about 75%, 80%, 90% or 95% by administration of the double-stranded oligonucleotide featured in the invention.

The terms "treat," "treatment," and the like, refer to relief from or alleviation of an infectious disease or an autoimmune disease. In the context of the present invention insofar as it relates to any of the other conditions recited herein below (e.g., a CD45-mediated condition other than an infectious disease or autoimmune disease), the terms "treat," "treatment," and the like mean to relieve or alleviate at least one symptom associated with such condition, or to slow or reverse the progression of such condition.

As used herein, the term "CD45-mediated condition or disease" and related terms and phrases refer to a condition or disorder characterized by inappropriate, e.g., greater than normal, CD45 activity. Inappropriate CD45 functional activity might arise as the result of CD45 expression in cells which normally do not express CD45 or increased CD45 expression (leading to, e.g., autoimmune disease). A CD45-mediated condition or disease may be completely or partially mediated by inappropriate CD45 functional activity. However, a CD45-mediated condition or disease is one in which modulation of CD45 results in some effect on the underlying condition or disorder (e.g., a CD45 inhibitor results in some improvement in patient well-being in at least some patients).

As used herein, the phrases "therapeutically effective amount" and "prophylactically effective amount" refer to an amount that provides a therapeutic benefit in the treatment, prevention, or management of an infectious disease or an overt symptom of infection, or an autoimmune disease. The specific amount that is therapeutically effective can be readily determined by ordinary medical practitioner, and may vary depending on factors known in the art, such as, e.g. the type of infection or autoimmune disease, the patient's history and age, the stage of the disease, and the administration of other agents.

As used herein, a "pharmaceutical composition" includes a pharmacologically effective amount of a dsRNA and a pharmaceutically acceptable carrier. As used herein, "pharmacologically effective amount," "therapeutically effective amount" or simply "effective amount" refers to that amount of a RNA effective to produce the intended pharmacological, therapeutic or preventive result. For example, if a given clinical treatment is considered effective when there is at least a 25% reduction in a measurable parameter associated with a disease or disorder, a therapeutically effective amount of a drug for the treatment of that disease or disorder is the amount necessary to effect at least a 25% reduction in that parameter.

The term "pharmaceutically acceptable carrier" refers to a carrier for administration of a therapeutic agent. Such carriers include, but are not limited to, saline, buffered saline, dextrose, water, glycerol, ethanol, and combinations thereof. The term specifically excludes cell culture medium. For drugs administered orally, pharmaceutically acceptable carriers include, but are not limited to pharmaceutically acceptable excipients such as inert diluents, disintegrating agents, binding agents, lubricating agents, sweetening agents, flavoring agents, coloring agents and preservatives. Suitable inert diluents include sodium and calcium carbonate, sodium and calcium phosphate, and lactose, while corn starch and alginic acid are suitable disintegrating agents. Binding agents may include starch and gelatin, while the lubricating agent, if present, will generally be magnesium stearate, stearic acid or talc. If desired, the tablets may be coated with a material such as glyceryl monostearate or glyceryl distearate, to delay absorption in the gastrointestinal tract.

As used herein, a "transformed cell" is a cell into which a vector has been introduced from which a dsRNA molecule may be expressed.

II. Double-stranded Ribonucleic Acid (dsRNA)

In one embodiment, the invention provides double-stranded ribonucleic acid (dsRNA) molecules for inhibiting the expression of the CD45 gene in a cell or mammal. The dsRNA includes an antisense strand including a region of complementarity which is complementary to the corresponding region of an mRNA formed in the expression of the CD45 gene, and wherein the region of complementarity is less than 30 nucleotides in length, generally 19-24 nucleotides in length. In another embodiment the dsRNA, upon contact with a cell expressing said CD45 gene, inhibits the expression of said CD45 gene, e.g., in an assay described herein, e.g., in a P388D1 cell assay (or an assay based on a similar cell) as described herein, by at least 20%, or preferably by at least 40%. The dsRNA includes two RNA strands that are sufficiently complementary to hybridize to form a duplex structure. The sense strand includes a region which is complementary to the antisense strand, such that the two strands hybridize and form a duplex structure when combined under suitable conditions. Generally, the duplex structure is between 15 and 30, more generally between 18 and 25, yet more generally between 19 and 24, and most generally between 21 and 23 base pairs in length. Similarly, the region of complementarity to the target sequence is between 15 and 30, more generally between 18 and 25, yet more generally between 19 and 24, and most generally between 19 and 21 nucleotides in length. In some embodiments, the dsRNA is between 10 and 15 nucleotides in length, and in other embodiments, the dsRNA is between 25 and 30 nucleotides in length. The dsRNA featured in the invention may further include one or more single-stranded nucleotide overhang(s).

The dsRNA can be synthesized by standard methods known in the art as further discussed below, e.g., by use of an automated DNA synthesizer, such as are commercially available from, for example, Biosearch, Applied Biosystems, Inc. In one embodiment, the CD45 gene is the human CD45 gene. In some embodiments, the antisense strand of the dsRNA includes a sense sequence from Tables 2, 4 and 5, and the sense strand of the dsRNA includes a sense sequence from Tables 2, 4 and 5.

In other embodiments, the dsRNA includes at least one nucleotide sequence selected from the groups of sequences provided in Tables 2, 4 and 5. In other embodiments, the dsRNA includes at least two sequences selected from this group, wherein one of the at least two sequences is complementary to another of the at least two sequences, and one of the at least two sequences is substantially complementary to a sequence of an mRNA generated in the expression of the CD45 gene. Generally, the dsRNA includes two oligonucleotides, wherein one oligonucleotide is described as a sense strand in Tables 2, 4, or 5, and the second oligonucleotide is described as an antisense strand in Tables 2, 4 or 5.

The skilled person is well aware that dsRNAs including a duplex structure of between 20 and 23, but specifically 21, base pairs have been identified as particularly effective in inducing RNA interference (Elbashir et al., EMBO 2001, 20:6877-6888). However, others have found that shorter or longer dsRNAs can be effective as well. In the embodiments described above, by virtue of the nature of the oligonucleotide sequences provided in Tables 2, 4, or 5, the dsRNAs featured in the invention can include at least one strand of a length of minimally 21 nt. It can be reasonably expected that shorter dsRNAs including one of the sequences of Table 2, 4 or 5, minus only a few nucleotides on one or both ends may be similarly effective as compared to the dsRNAs described above. Hence, dsRNAs including a partial sequence of at least 15, 16, 17, 18, 19, 20, or more contiguous nucleotides from one of the sequences of Table 2, 4 or 5, and differing in their ability to inhibit the expression of the CD45 gene in a FACS assay as described herein below by not more than 5, 10, 15, 20, 25, or 30% inhibition from a dsRNA including the full sequence, are contemplated by the invention.

In addition, the dsRNA agents provided in Tables 2, 4 and 5 identify sites in the CD45 mRNA that are susceptible to RNAi based cleavage. As such, the invention further includes dsRNAs that target within the sequence targeted by one of the agents featured in the present invention. As used herein, a second dsRNA is said to target within the sequence of a first dsRNA if the second dsRNA cleaves the message anywhere within the mRNA that is complementary to the antisense strand of the first dsRNA. Such a second agent will generally consist of at least 15 contiguous nucleotides from one of the sequences provided in Tables 2, 4 and 5 coupled to additional nucleotide sequences taken from the region contiguous to the selected sequence in the CD45 gene.

The dsRNA featured in the invention can contain one or more mismatches to the target sequence. In one embodiment, the dsRNA targeting CD45 contains no more than 3 mismatches. If the antisense strand of the dsRNA contains mismatches to a target sequence, it is preferable that the area of mismatch not be located in the center of the region of complementarity. If the antisense strand of the dsRNA contains mismatches to the target sequence, it is preferable that the mismatch be restricted to 5 nucleotides from either end, for example 5, 4, 3, 2, or 1 nucleotide from either the 5' or 3' end of the region of complementarity. For example, for a 23 nucleotide dsRNA strand which is complementary to a region of the CD45 gene, the dsRNA generally does not contain any mismatch within the central 13 nucleotides. The methods described within the invention can be used to determine whether a dsRNA containing a mismatch to a target sequence is effective in inhibiting the expression of the CD45 gene. Consideration of the efficacy of dsRNAs with mismatches in inhibiting expression of the CD45 gene is important, especially if the particular region of complementarity in the CD45 gene is known to have polymorphic sequence variation within the population.

In one embodiment, at least one end of the dsRNA has a single-stranded nucleotide overhang of 1 to 4, generally 1 or 2 nucleotides. dsRNAs having at least one nucleotide overhang have unexpectedly superior inhibitory properties than their blunt-ended counterparts. In one embodiment the presence of only one nucleotide overhang strengthens the interference activity of the dsRNA, without affecting its overall stability. dsRNA having only one overhang has proven particularly stable and effective in vivo, as well as in a variety of cells, cell culture mediums, blood, and serum. Generally, the single-stranded overhang is located at the 3'-terminal end of the antisense strand or, alternatively, at the 3'-terminal end of the sense strand. The dsRNA may also have a blunt end, generally located at the 5'-end of the antisense strand. Such dsRNAs have improved stability and inhibitory activity, thus allowing administration at low dosages, i.e., less than 5 mg/kg body weight of the recipient per day. In one embodiment, the antisense strand of the dsRNA has a 1-10 nucleotide overhang at the 3' end and/or the 5' end. In one embodiment, the sense strand of the dsRNA has a 1-10 nucleotide overhang at the 3' end and/or the 5' end. In another embodiment, one or more of the nucleotides in the overhang is replaced with a nucleoside thiophosphate.

In yet another embodiment, the dsRNA is chemically modified to enhance stability. The nucleic acids featured in the invention may be synthesized and/or modified by methods well established in the art, such as those described in "Current protocols in nucleic acid chemistry", Beaucage, S. L. et al. (Edrs.), John Wiley & Sons, Inc., New York, N.Y., USA, which is hereby incorporated herein by reference. Specific examples of dsRNA compounds useful in this invention include dsRNAs containing modified backbones or no natural internucleoside linkages. As defined in this specification, dsRNAs having modified backbones include those that retain a phosphorus atom in the backbone and those that do not have a phosphorus atom in the backbone. For the purposes of this specification, and as sometimes referenced in the art, modified dsRNAs that do not have a phosphorus atom in their internucleoside backbone can also be considered to be oligonucleosides.

Modified dsRNA backbones include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those) having inverted polarity wherein the adjacent pairs of nucleoside units are linked 3'-5' to 5'-3' or 2'-5' to 5'-2'. Various salts, mixed salts and free acid forms are also included.

Representative U.S. patents that teach the preparation of the above phosphorus-containing linkages include, but are not limited to, U.S. Pat. Nos. 3,687,808; 4,469,863; 4,476,301; 5,023,243; 5,177,195; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,316; 5,550,111; 5,563,253; 5,571,799; 5,587,361; and 5,625,050, each of which is herein incorporated by reference Modified dsRNA backbones that do not include a phosphorus atom therein have backbones that are formed by short chain alkyl or cycloalkyl internucleoside linkages, mixed heteroatoms and alkyl or cycloalkyl internucleoside linkages, or ore or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative U.S. patents that teach the preparation of the above oligonucleosides include, but are not limited to, U.S. Pat. Nos. 5,034,506; 5,166,315; 5,185,444; 5,214,134; 5,216,141; 5,235,033; 5,64,562; 5,264,564; 5,405,938; 5,434,257; 5,466,677; 5,470,967; 5,489,677; 5,541,307; 5,561,225; 5,596,086; 5,602,240; 5,608,046; 5,610,289; 5,618,704; 5,623,070; 5,663,312; 5,633,360; 5,677,437; and, 5,677,439, each of which is herein incorporated by reference.

In other dsRNA mimetics, both the sugar and the internucleoside linkage, i.e., the backbone, of the nucleotide units are replaced with novel groups. The base units are maintained for hybridization with an appropriate nucleic acid target compound. One such oligomeric compound, a dsRNA mimetic that has been shown to have excellent hybridization properties, is referred to as a peptide nucleic acid (PNA). In PNA compounds, the sugar backbone of a dsRNA is replaced with an amide containing backbone, in particular an aminoethylglycine backbone. The nucleobases are retained and are bound directly or indirectly to aza nitrogen atoms of the amide portion of the backbone. Representative U.S. patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al., Science, 1991, 254, 1497-1500.

Typical embodiments include dsRNAs with phosphorothioate backbones and oligonucleosides with heteroatom backbones, and in particular—$CH_2$—NH—$CH_2$—, —$CH_2$—N($CH_3$)—O—$CH_2$—[known as a methylene (methylimino) or MMI backbone], —$CH_2$—O—N($CH_3$)—$CH_2$—, —$CH_2$—N($CH_3$)—N($CH_3$)—$CH_2$— and —N($CH_3$)—$CH_2$—$CH_2$— [wherein the native phosphodiester backbone is represented as —O—P—O—$CH_2$—] of the above-referenced U.S. Pat. No. 5,489,677, and the amide backbones of the above-referenced U.S. Pat. No. 5,602,240. Other suitable dsRNAs have morpholino backbone structures of the above-referenced U.S. Pat. No. 5,034,506.

Modified dsRNAs may also contain one or more substituted sugar moieties. Typical dsRNAs include one of the following at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Other dsRNAs include $O[(CH_2)_nO]_mCH_3$, $O(CH_2)_nOCH_3$, $O(CH_2)_nNH_2$, $O(CH_2)_nCH_3$, $O(CH_2)_nONH_2$, and $O(CH_2)_n ON[(CH_2)_nCH_3)]_2$, where n and m are from 1 to about 10. Other typical dsRNAs include one of the following at the 2' position: $C_1$ to $C_{10}$ lower alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an dsRNA, or a group for improving the pharmacodynamic properties of an dsRNA, and other substituents having similar properties. In one embodiment, the modification includes 2'-methoxyethoxy (2'-O—$CH_2CH_2OCH_3$, also known as 2'-O-(2-methoxyethyl) or 2'-MOE) (Martin et al., Helv. Chim. Acta, 1995, 78, 486-504), i.e., an alkoxy-alkoxy group. Another suitable modification includes 2'-dimethylaminooxyethoxy, i.e., a $O(CH_2)_2ON(CH_3)_2$ group, also known as 2'-DMAOE, as described in examples hereinbelow, and 2'-dimethylaminoethoxyethoxy (also known in the art as 2'-O-dimethylaminoethoxyethyl or 2'-DMAEOE), i.e., 2'-O—$CH_2$—O—$CH_2$—N($CH_3$)$_2$, also described in examples hereinbelow.

Other suitable modifications include 2'-methoxy (2'-$OCH_3$), 2'-aminopropoxy (2'-$OCH_2CH_2CH_2NH_2$) and 2'-fluoro (2'-F). Similar modifications may also be made at other positions on the dsRNA, particularly the 3' position of the sugar on the 3' terminal nucleotide or in 2'-5' linked dsRNAs and the 5' position of 5' terminal nucleotide. DsRNAs may also have sugar mimetics such as cyclobutyl moieties in place of the pentofuranosyl sugar. Representative U.S. patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920, certain of which are commonly owned with the instant application, and each of which is herein incorporated by reference in its entirety.

dsRNAs may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl anal other 8-substituted adenines and guanines, 5-halo, particularly 5-bromo, 5-trifluoromethyl and other 5-substituted uracils and cytosines, 7-methylguanine and 7-methyladenine, 8-azaguanine and 8-azaadenine, 7-deazaguanine and 7-daazaadenine and 3-deazaguanine and 3-deazaadenine. Further nucleobases include those disclosed in U.S. Pat. No. 3,687,808, those disclosed in The Concise Encyclopedia Of Polymer Science And Engineering, pages 858-859, Kroschwitz, J. L, ed. John Wiley & Sons, 1990, these disclosed by Englisch et al., Angewandte Chemie, International Edition, 1991, 30, 613, and those disclosed by Sanghvi, Y S., Chapter 15, DsRNA Research and Applications, pages 289-302, Crooke, S. T. and Lebleu, B., Ed., CRC Press, 1993. Certain of these nucleobases are particularly useful for increasing the binding affinity of the oligomeric compounds featured in the invention. These include 5-substituted pyrimidines, 6-azapyrimidines and N-2, N-6 and 0-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi, Y. S., Crooke, S. T. and Lebleu, B., Eds., DsRNA Research and Applications, CRC Press, Boca Raton, 1993, pp. 276-278) and are suitable base substitutions, particularly when combined with 2'-O-methoxyethyl sugar modifications.

Representative U.S. patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,30; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; and 5,681,941, each of which is herein incorporated by reference, and U.S. Pat. No. 5,750,692, also herein incorporated by reference.

Another modification of the dsRNAs featured in the invention involves chemically linking to the dsRNA one or more moieties or conjugates which enhance the activity, cellular distribution or cellular uptake of the dsRNA. Such moieties include but are not limited to lipid moieties such as a cholesterol moiety (Letsinger et al., Proc. Natl. Acid. Sci. USA, 199, 86, 6553-6556), cholic acid (Manoharan et al., Biorg. Med. Chem. Let., 1994 4 1053-1060), a thioether, e.g., beryl-5-tritylthiol (Manoharan et al., Ann. N.Y. Acad. Sci., 1992, 660, 306-309; Manoharan et al., Biorg. Med. Chem. Let., 1993, 3, 2765-2770), a thiocholesterol (Oberhauser et al., Nucl. Acids Res., 1992, 20, 533-538), an aliphatic chain, e.g., dodecandiol or undecyl residues (Saison-Behmoaras et al., EMBO J, 1991, 10, 1111-1118; Kabanov et al., FEBS Lett., 1990, 259, 327-330; Svinarchuk et al., Biochimie, 1993, 75, 49-54), a phospholipid, e.g., di-hexadecyl-rac-glycerol or triethyl-ammonium 1,2-di-O-hexadecyl-rac-glycero-3-Hphosphonate (Manoharan et al., Tetrahedron Lett., 1995, 36, 3651-3654; Shea et al., Nucl. Acids Res., 1990, 18, 3777-3783), a polyamine or a polyethylene glycol chain (Manoharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochim. Biophys. Acta, 1995, 1264, 229-237), or an octadecylamine or hexylamino-carbonyloxycholesterol moiety (Crooke et al., J. Pharmacol. Exp. Ther., 1996, 277, 923-937).

Representative U.S. patents that teach the preparation of such dsRNA conjugates include, but are not limited to, U.S. Pat. Nos. 4,828,979; 4,948,882; 5,218,105; 5,525,465; 5,541, 313; 5,545,730; 5,552,538; 5,578,717, 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241; 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, each of which is herein incorporated by reference.

It is not necessary for all positions in a given compound to be uniformly modified, and in fact more than one of the aforementioned modifications may be incorporated in a single compound or even at a single nucleoside within a dsRNA. The present invention also includes dsRNA compounds which are chimeric compounds. "Chimeric" dsRNA compounds or "chimeras," in the context of this invention, are dsRNA compounds, particularly dsRNAs, which contain two or more chemically distinct regions, each made up of at least one monomer unit, i.e., a nucleotide in the case of a dsRNA compound. These dsRNAs typically contain at least one region wherein the dsRNA is modified so as to confer upon the dsRNA increased resistance to nuclease degradation, increased cellular uptake, and/or increased binding affinity for the target nucleic acid. An additional region of the dsRNA may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of dsRNA inhibition of gene expression. Consequently, comparable results can often be obtained with shorter dsRNAs when chimeric dsRNAs are used, compared to phosphorothioate deoxydsRNAs hybridizing to the same target region. Cleavage of the RNA target can be routinely detected by gel electrophoresis and, if necessary, associated nucleic acid hybridization techniques known in the art.

In certain instances, the dsRNA may be modified by a non-ligand group. A number of non-ligand molecules have been conjugated to dsRNAs in order to enhance the activity, cellular distribution or cellular uptake of the dsRNA, and procedures for performing such conjugations are available in the scientific literature. Such non-ligand moieties have included lipid moieties, such as cholesterol (Letsinger et al., Proc. Natl. Acad. Sci. USA, 1989, 86:6553), cholic acid (Manoharan et al., Bioorg. Med. Chem. Lett., 1994, 4:1053), a thioether, e.g., hexyl-5-tritylthiol (Manoharan et al., Ann. N.Y. Acad. Sci., 1992, 660:306; Manoharan et al., Bioorg. Med. Chem. Let., 1993, 3:2765), a thiocholesterol (Oberhauser et al., Nucl. Acids Res., 1992, 20:533), an aliphatic chain, e.g., dodecandiol or undecyl residues (Saison-Behmoaras et al., EMBO J., 1991, 10:111; Kabanov et al., FEBS Lett., 1990, 259:327; Svinarchuk et al., Biochimie, 1993, 75:49), a phospholipid, e.g., di-hexadecyl-rac-glycerol or triethylammonium 1,2-di-O-hexadecyl-rac-glycero-3-H-phosphonate (Manoharan et al., Tetrahedron Lett., 1995, 36:3651; Shea et al., Nucl. Acids Res., 1990, 18:3777), a polyamine or a polyethylene glycol chain (Manoharan et al., Nucleosides & Nucleotides, 1995, 14:969), or adamantane acetic acid (Manoharan et al., Tetrahedron Lett., 1995, 36:3651), a palmityl moiety (Mishra et al., Biochim. Biophys. Acta, 1995, 1264:229), or an octadecylamine or hexylamino-carbonyl-oxycholesterol moiety (Crooke et al., J. Pharmacol. Exp. Ther., 1996, 277:923). Representative United States patents that teach the preparation of such dsRNA conjugates have been listed above. Typical conjugation protocols involve the synthesis of dsRNAs bearing an aminolinker at one or more positions of the sequence. The amino group is then reacted with the molecule being conjugated using appropriate coupling or activating reagents. The conjugation reaction may be performed either with the dsRNA still bound to the solid support or following cleavage of the dsRNA in solution phase. Purification of the dsRNA conjugate by HPLC typically affords the pure conjugate. The use of a cholesterol conjugate is particularly suitable since such a moiety can increase targeting vaginal epithelium cells, a site of CD45 expression.

Vector Encoded dsRNA Agents

The dsRNA featured in the invention can also be expressed from recombinant viral vectors intracellularly in vivo. The recombinant viral vectors featured in the invention comprise sequences encoding the dsRNA and any suitable promoter for expressing the dsRNA sequences. Suitable promoters include, for example, the U6 or H1 RNA pol III promoter sequences and the cytomegalovirus promoter. Selection of other suitable promoters is within the skill in the art. The recombinant viral vectors can also comprise inducible or regulatable promoters for expression of the dsRNA in a particular tissue or in a particular intracellular environment. The use of recombinant viral vectors to deliver dsRNA to cells in vivo is discussed in more detail below.

dsRNA featured in the invention can be expressed from a recombinant viral vector either as two separate, complementary RNA molecules, or as a single RNA molecule with two complementary regions.

Any viral vector capable of accepting the coding sequences for the dsRNA molecule(s) to be expressed can be used, for example vectors derived from adenovirus (AV); adeno-associated virus (AAV); retroviruses (e.g, lentiviruses (LV), Rhabdoviruses, murine leukemia virus); herpes virus, and the like. The tropism of viral vectors can be modified by pseudotyping the vectors with envelope proteins or other surface antigens from other viruses, or by substituting different viral capsid proteins, as appropriate.

For example, lentiviral vectors can be pseudotyped with surface proteins from vesicular stomatitis virus (VSV), rabies, Ebola, Mokola, and the like. AAV vectors can be made to target different cells by engineering the vectors to express different capsid protein serotypes. For example, an AAV vector expressing a serotype 2 capsid on a serotype 2 genome is called AAV 2/2. This serotype 2 capsid gene in the AAV 2/2 vector can be replaced by a serotype 5 capsid gene to produce an AAV 2/5 vector. Techniques for constructing AAV vectors which express different capsid protein serotypes are within the skill in the art; see, e.g., Rabinowitz J E et al. (2002), J Virol 76:791-801, the entire disclosure of which is herein incorporated by reference.

Selection of recombinant viral vectors suitable for use in the invention, methods for inserting nucleic acid sequences for expressing the dsRNA into the vector, and methods of delivering the viral vector to the cells of interest are within the skill in the art. See, for example, Dornburg R (1995), Gene Therap. 2: 301-310; Eglitis M A (1988), Biotechniques 6: 608-614; Miller A D (1990), Hum Gene Therap. 1: 5-14; Anderson W F (1998), Nature 392: 25-30; and Rubinson D A et al., Nat. Genet. 33: 401-406, the entire disclosures of which are herein incorporated by reference.

Typical viral vectors are those derived from AV and AAV. In one embodiment, the dsRNA featured in the invention is expressed as two separate, complementary single-stranded RNA molecules from a recombinant AAV vector including, for example, either the U6 or H1 RNA promoters, or the cytomegalovirus (CMV) promoter.

A suitable AV vector for expressing the dsRNA featured in the invention, a method for constructing the recombinant AV vector, and a method for delivering the vector into target cells, are described in Xia H et al. (2002), Nat. Biotech. 20: 1006-1010.

Suitable AAV vectors for expressing the dsRNA featured in the invention, methods for constructing the recombinant AV vector, and methods for delivering the vectors into target cells are described in Samulski R et al. (1987), J. Virol. 61: 3096-3101; Fisher K J et al. (1996), J. Virol, 70: 520-532; Samulski R et al. (1989), J. Virol. 63: 3822-3826; U.S. Pat. No. 5,252,479; U.S. Pat. No. 5,139,941; International Patent Application No. WO 94/13788; and International Patent Application No. WO 93/24641, the entire disclosures of which are herein incorporated by reference.

III. Pharmaceutical Compositions Including dsRNA

The invention provides pharmaceutical compositions including a dsRNA, as described herein, and a pharmaceutically acceptable carrier. The pharmaceutical composition including the dsRNA is useful for treating a disease or disorder associated with the expression or activity of the CD45 gene, such as pathological processes mediated by CD45 expression. Such pharmaceutical compositions are formulated based on the mode of delivery. One example is compositions that are formulated for systemic administration via parenteral delivery.

The pharmaceutical compositions featured in the invention are administered in dosages sufficient to inhibit expression of the CD45 gene. The present inventors have found that, because of their improved efficiency, compositions including the dsRNA can be administered at surprisingly low dosages. Dosages of 0.6 mg or greater of dsRNA per kilogram body weight of recipient per day is sufficient to suppress expression of the CD45 gene by greater than 35%, with higher dosages capable of achieving 65% reduction in expression of the CD45 gene.

In general, a suitable dose of dsRNA will be in the range of 0.01 to 200.0 milligrams per kilogram body weight of the recipient per day, generally in the range of 0.02 to 50 mg per kilogram body weight per day. For example, the dsRNA can be administered at 0.01, 0.1, 0.05 mg/kg, 0.5 mg/kg, 1 mg/kg, 2 mg/kg, 3 mg/kg, 5 mg/kg, 10 mg/kg, 20 mg/kg, 30 mg/kg, 40 mg/kg, or 50 mg/kg per single dose. The pharmaceutical composition may be administered once daily, or the dsRNA may be administered as two, three, or more sub-doses at appropriate intervals throughout the day or even using continuous infusion or delivery through a controlled release formulation. In that case, the dsRNA contained in each sub-dose must be correspondingly smaller in order to achieve the total daily dosage. The dosage unit can also be compounded for delivery over several days, e.g., using a conventional sustained release formulation which provides sustained release of the dsRNA over a several day period. Sustained release formulations are well known in the art and are particularly useful for vaginal delivery of agents, such as could be used with the dsRNAs featured in the invention. In this embodiment, the dosage unit contains a corresponding multiple of the daily dose.

The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of a composition can include a single treatment or a series of treatments. Estimates of effective dosages and in vivo half-lives for the individual dsRNAs encompassed by the invention can be made using conventional methodologies or on the basis of in vivo testing using an appropriate animal model, as described elsewhere herein.

Advances in mouse genetics have generated a number of mouse models for the study of various human diseases, such as pathological processes mediated by CD45 expression. Such models are used for in vivo testing of dsRNA, as well as for determining a therapeutically effective dose.

The present invention also includes pharmaceutical compositions and formulations which include dsRNA targeting CD45. The pharmaceutical compositions may be administered in a number of ways depending upon whether local or systemic treatment is desired and upon the area to be treated. Administration may be topical (e.g., by a transdermal patch), pulmonary (e.g., by inhalation or insufflation of powders or aerosols, including by nebulizer; intratracheal, intranasal, epidermal and transdermal), oral or parenteral. Administration may also be designed to result in preferential localization to particular tissues through local delivery, e.g., by direct intraarticular injection into joints, by rectal administration for direct delivery to the gut and intestines, by intravaginal administration for delivery to the cervix and vagina, by intravitreal administration for delivery to the eye. Parenteral administration includes intravenous, intraarterial, intraarticular, subcutaneous, intraperitoneal or intramuscular injection or infusion; subdermal, e.g., via an implanted device; or intracranial, e.g., by intrathecal or intraventricular administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful. Typical topical formulations include those in which the dsRNAs featured in the invention are in admixture with a topical delivery agent such as lipids, liposomes, fatty acids, fatty acid esters, steroids, chelating agents and surfactants. Typical lipids and liposomes include neutral (e.g., dioleoylphosphatidyl DOPE ethanolamine, dimyristoylphosphatidyl choline DMPC, distearolyphosphatidyl choline) negative (e.g., dimyristoylphosphatidyl glycerol DMPG), and cationic (e.g., dioleoyltetramethylaminopropyl DOTAP and dioleoylphosphatidyl ethanolamine DOTMA). DsRNAs featured the invention may be encapsulated within liposomes or may form complexes thereto, in particular to cationic liposomes. Alternatively, dsRNAs may be complexed to lipids, in particular to cationic lipids. Typical fatty acids and esters include but are not limited arachidonic acid, oleic acid, eicosanoic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a $C_{1-10}$ alkyl ester (e.g., isopropylmyristate IPM), monoglyceride, diglyceride or pharmaceutically acceptable salt thereof. Topical formulations are described in detail in U.S. patent application Ser. No. 09/315,298 filed May 20, 1999, which is incorporated herein by reference in its entirety.

In one embodiment, a dsRNA featured in the invention is fully encapsulated in the lipid formulation (e.g., to form a SPLP, pSPLP, SNALP, or other nucleic acid-lipid particle). As used herein, the term "SNALP" refers to a stable nucleic acid-lipid particle, including SPLP. As used herein, the term "SPLP" refers to a nucleic acid-lipid particle comprising plasmid DNA encapsulated within a lipid vesicle. SNALPs and SPLPs typically contain a cationic lipid, a non-cationic lipid, and a lipid that prevents aggregation of the particle (e.g., a PEG-lipid conjugate). SNALPs and SPLPs are extremely useful for systemic applications, as they exhibit extended circulation lifetimes following intravenous (i.v.) injection and accumulate at distal sites (e.g., sites physically separated from the administration site). SPLPs include "pSPLP," which include an encapsulated condensing agent-nucleic acid complex as set forth in PCT Publication No. WO 00/03683. The particles of the present invention typically have a mean diameter of about 50 nm to about 150 nm, more typically about 60 nm to about 130 nm, more typically about 70 nm to about 110 nm, most typically about 70 to about 90 nm, and are substantially nontoxic.

In addition, the nucleic acids when present in the nucleic acid-lipid particles of the present invention are resistant in aqueous solution to degradation with a nuclease. Nucleic acid-lipid particles and their method of preparation are disclosed in, e.g., U.S. Pat. Nos. 5,976,567; 5,981,501; 6,534,484; 6,586,410; 6,815,432; and PCT Publication No. WO 96/40964.

In one embodiment, the lipid to drug ratio (mass/mass ratio) (e.g., lipid to dsRNA ratio) will be in the range of from about 1:1 to about 50:1, from about 1:1 to about 25:1, from about 3:1 to about 15:1, from about 4:1 to about 10:1, from about 5:1 to about 9:1, or about 6:1 to about 9:1.

The cationic lipid may be, for example, N,N-dioleyl-N,N-dimethylammonium chloride (DODAC), N,N-distearyl-N,N-dimethylammonium bromide (DDAB), N-(1-(2,3-dioleoyloxy)propyl)-N,N,N-trimethylammonium chloride (DOTAP), N-(1-(2,3-dioleyloxy)propyl)-N,N,N-trimethylammonium chloride (DOTMA), N,N-dimethyl-2,3-dioleyloxy)propylamine (DODMA), 1,2-DiLinoleyloxy-N,N-dimethylaminopropane (DLinDMA),1,2-Dilinolenyloxy-N,N-dimethylaminopropane (DLenDMA), 1,2-Dilinoleylcarbamoyloxy-3-dimethylaminopropane (DLin-C-DAP), 1,2-Dilinoleyoxy-3-(dimethylamino)acetoxypropane (DLin-DAC), 1,2-Dilinoleyoxy-3-morpholinopropane (DLin-MA), 1,2-Dilinoleoyl-3-dimethylaminopropane (DLinDAP), 1,2-Dilinoleylthio-3-dimethylaminopropane (DLin-S-DMA), 1-Linoleoyl-2-linoleyloxy-3-dimethylaminopropane (DLin-2-DMAP), 1,2-Dilinoleyloxy-3-trimethylaminopropane chloride salt (DLin-TMA.Cl), 1,2-Dilinoleoyl-3-trimethylaminopropane chloride salt (DLin-TAP.Cl), 1,2-Dilinoleyloxy-3-(N-methylpiperazino)propane (DLin-MPZ), or 3-(N,N-Dilinoleylamino)-1,2-propanediol (DLinAP), 3-(N,N-Dioleylamino)-1,2-propanedio (DOAP), 1,2-Dilinoleyloxo-3-(2-N,N-dimethylamino)ethoxypropane (DLin-EG-DMA), 2,2-Dilinoleyl-4-dimethylaminomethyl-[1,3]-dioxolane (DLin-K-DMA), or a mixture thereof. The cationic lipid may comprise from about 20 mol % to about 50 mol % or about 40 mol % of the total lipid present in the particle.

The non-cationic lipid may be an anionic lipid or a neutral lipid including, but not limited to, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoyl-phosphatidylethanolamine (DOPE), palmitoyloleoylphosphatidylcholine (POPC), palmitoyloleoyl-phosphatidylethanolamine (POPE), dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), distearoyl-phosphatidyl-ethanolamine (DSPE), 16-O-monomethyl PE, 16-O-dimethyl PE, 18-1-trans PE, 1-stearoyl-2-oleoyl-phosphatidyethanolamine (SOPE), cholesterol, or a mixture thereof. The non-cationic lipid may be from about 5 mol % to about 90 mol %, about 10 mol %, or about 58 mol % if cholesterol is included, of the total lipid present in the particle.

The conjugated lipid that inhibits aggregation of particles may be, for example, a polyethyleneglycol (PEG)-lipid including, without limitation, a PEG-diacylglycerol (DAG), a PEG-dialkyloxypropyl (DAA), a PEG-phospholipid, a PEG-ceramide (Cer), or a mixture thereof. The PEG-DAA conjugate may be, for example, a PEG-dilauryloxypropyl ($C_{12}$), a PEG-dimyristyloxypropyl ($C_{14}$), a PEG-dipalmityloxypropyl ($C_{16}$), or a PEG-distearyloxypropyl ($C_{18}$). The conjugated lipid that prevents aggregation of particles may be from 0 mol % to about 20 mol % or about 2 mol % of the total lipid present in the particle.

In some embodiments, the nucleic acid-lipid particle further includes cholesterol at, e.g., about 10 mol % to about 60 mol % or about 48 mol % of the total lipid present in the particle.

In one embodiment, the lipidoid ND98.4HCl (MW 1487) (Formula 1), Cholesterol (Sigma-Aldrich), and PEG-Ceramide C16 (Avanti Polar Lipids) can be used to prepare lipid-siRNA nanoparticles (i.e., LNP01 particles). Stock solutions of each in ethanol can be prepared as follows: ND98, 133 mg/mL; Cholesterol, 25 mg/mL, PEG-Ceramide C16, 100 mg/mL. The ND98, Cholesterol, and PEG-Ceramide C16 stock solutions can then be combined in a, e.g., 42:48:10 molar ratio. The combined lipid solution can be mixed with aqueous siRNA (e.g., in sodium acetate pH 5) such that the final ethanol concentration is about 35-45% and the final sodium acetate concentration is about 100-300 mM. Lipid-siRNA nanoparticles typically form spontaneously upon mixing. Depending on the desired particle size distribution, the resultant nanoparticle mixture can be extruded through a polycarbonate membrane (e.g., 100 nm cut-off) using, for example, a thermobarrel extruder, such as Lipex Extruder (Northern Lipids, Inc). In some cases, the extrusion step can be omitted. Ethanol removal and simultaneous buffer exchange can be accomplished by, for example, dialysis or tangential flow filtration. Buffer can be exchanged with, for example, phosphate buffered saline (PBS) at about pH 7, e.g., about pH 6.9, about pH 7.0, about pH 7.1, about pH 7.2, about pH 7.3, or about pH 7.4.

Formula 1

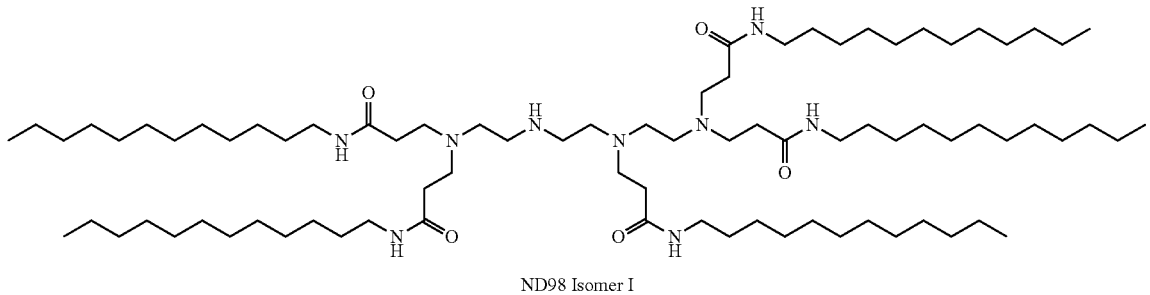

ND98 Isomer I

LNP01 formulations are described, e.g., in International Application Publication No. WO 2008/042973, which is hereby incorporated by reference.

Formulations prepared by either the standard or extrusion-free method can be characterized in similar manners. For example, formulations are typically characterized by visual inspection. They should be whitish translucent solutions free from aggregates or sediment. Particle size and particle size distribution of lipid-nanoparticles can be measured by light scattering using, for example, a Malvern Zetasizer Nano ZS (Malvern, USA). Particles should be about 20-300 nm, such as 40-100 nm in size. The particle size distribution should be unimodal. The total siRNA concentration in the formulation, as well as the entrapped fraction, is estimated using a dye exclusion assay. A sample of the formulated siRNA can be incubated with an RNA-binding dye, such as Ribogreen (Molecular Probes) in the presence or absence of a formulation disrupting surfactant, e.g., 0.5% Triton-X100. The total siRNA in the formulation can be determined by the signal from the sample containing the surfactant, relative to a standard curve. The entrapped fraction is determined by subtracting the "free" siRNA content (as measured by the signal in the absence of surfactant) from the total siRNA content. Percent entrapped siRNA is typically >85%. For SNALP formulation, the particle size is at least 30 nm, at least 40 nm, at least 50 nm, at least 60 nm, at least 70 nm, at least 80 nm, at least 90 nm, at least 100 nm, at least 110 nm, and at least 120 nm. The suitable range is typically about at least 50 nm to about at least 110 nm, about at least 60 nm to about at least 100 nm, or about at least 80 nm to about at least 90 nm.

Compositions and formulations for oral administration include powders or granules, microparticulates, nanoparticulates, suspensions or solutions in water or non-aqueous media, capsules, gel capsules, sachets, tablets or minitablets. Thickeners, flavoring agents, diluents, emulsifiers, dispersing aids or binders may be desirable. Typical oral formulations are those in which dsRNAs featured in the invention are administered in conjunction with one or more penetration enhancers surfactants and chelators. Typical surfactants include fatty acids and/or esters or salts thereof, bile acids and/or salts thereof. Typical bile acids/salts include chenodeoxycholic acid (CDCA) and ursodeoxychenodeoxycholic acid (UDCA), cholic acid, dehydrocholic acid, deoxycholic acid, glucholic acid, glycholic acid, glycodeoxycholic acid, taurocholic acid, taurodeoxycholic acid, sodium tauro-24,25-dihydro-fusidate and sodium glycodihydrofusidate. Typical fatty acids include arachidonic acid, undecanoic acid, oleic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a monoglyceride, a diglyceride or a pharmaceutically acceptable salt thereof (e.g. sodium). Suitable combinations of penetration enhancers include, for example, fatty acids/salts in combination with bile acids/salts. One typical combination is the sodium salt of lauric acid, capric acid and UDCA. Further penetration enhancers include polyoxyethylene-9-lauryl ether, polyoxyethylene-20-cetyl ether. DsRNAs featured in the invention may be delivered orally, in granular form including sprayed dried particles, or complexed to form micro or nanoparticles. DsRNA complexing agents include poly-amino acids; polyimines; polyacrylates; polyalkylacrylates, polyoxethanes, polyalkylcyanoacrylates; cationized gelatins, albumins, starches, acrylates, polyethyleneglycols (PEG) and starches; polyalkylcyanoacrylates; DEAE-derivatized polyimines, pollulans, celluloses and starches. Typical complexing agents include chitosan, N-trimethylchitosan, poly-L-lysine, polyhistidine, polyornithine, polyspermines, protamine, polyvinylpyridine, polythiodiethylaminomethylethylene P(TDAE), polyaminostyrene (e.g. p-amino), poly(methylcyanoacrylate), poly(ethylcyanoacrylate), poly(butylcyanoacrylate), poly(isobutylcyanoacrylate), poly(isohexylcynaoacrylate), DEAE-methacrylate, DEAE-hexylacrylate, DEAE-acrylamide, DEAE-albumin and DEAE-dextran, polymethylacrylate, polyhexylacrylate, poly(D,L-lactic acid), poly(DL-lactic-co-glycolic acid (PLGA), alginate, and polyethyleneglycol (PEG). Oral formulations for dsRNAs and their preparation are described in detail in U.S. application. Ser. No. 08/886,829 (filed Jul. 1, 1997), Ser. No. 09/108,673 (filed Jul. 1, 1998), Ser. No. 09/256,515 (filed Feb. 23, 1999), Ser. No. 09/082,624 (filed May 21, 1998) and Ser. No. 09/315,298 (filed May 20, 1999), each of which is incorporated herein by reference in their entirety.

Compositions and formulations for parenteral, intrathecal or intraventricular administration may include sterile aqueous solutions which may also contain buffers, diluents and other suitable additives such as, but not limited to, penetration enhancers, carrier compounds and other pharmaceutically acceptable carriers or excipients.

Pharmaceutical compositions featured in the invention include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical formulations featured in the invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general, the formulations are prepared by uniformly and intimately bringing into association the active ingredients with liquid carriers or finely divided solid carriers or both, and then, if necessary, shaping the product.

The compositions featured in the invention may be formulated into any of many possible dosage forms such as, but not limited to, tablets, capsules, gel capsules, liquid syrups, soft gels, suppositories, and enemas. The compositions featured in the invention may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers.

In one embodiment, the pharmaceutical composition may be formulated and used as a foam. Pharmaceutical foams include formulations such as, but not limited to, emulsions, microemulsions, creams, jellies and liposomes. While basically similar in nature these formulations vary in the components and the consistency of the final product. The preparation of such compositions and formulations is generally known to those skilled in the pharmaceutical and formulation arts and may be applied to the formulation of the compositions featured herein.

Emulsions

The compositions featured in the invention may be prepared and formulated as emulsions. Emulsions are typically heterogenous systems of one liquid dispersed in another in the form of droplets usually exceeding 0.1 µm in diameter (Idson, in Pharmaceutical Dosage Forms, Lieberman, Rieger and Banker (Eds.), 1988, Marcel Dekker, Inc., New York, N.Y., volume 1, p. 199; Rosoff, in Pharmaceutical Dosage Forms, Lieberman, Rieger and Banker (Eds.), 1988, Marcel Dekker, Inc., New York, N.Y., Volume 1, p. 245; Block in Pharmaceutical Dosage Forms, Lieberman, Rieger and Banker (Eds.), 1988, Marcel Dekker, Inc., New York, N.Y., volume 2, p. 335; Higuchi et al., in Remington's Pharmaceutical Sciences, Mack Publishing Co., Easton, Pa., 1985, p. 301). Emulsions are often biphasic systems including two immiscible liquid phases intimately mixed and dispersed with each other. In general, emulsions may be of either the water-in-oil (w/o) or the oil-in-water (o/w) variety. When an aqueous phase is finely divided into and dispersed as minute droplets into a bulk oily phase, the resulting composition is called a water-in-oil (w/o) emulsion. Alternatively, when an oily phase is finely divided into and dispersed as minute droplets into a bulk aqueous phase, the resulting composition is called an oil-in-water (o/w) emulsion. Emulsions may contain additional components in addition to the dispersed phases, and the active drug which may be present as a solution in either the aqueous phase, oily phase or itself as a separate phase. Pharmaceutical excipients such as emulsifiers, stabilizers, dyes, and anti-oxidants may also be present in emulsions as needed. Pharmaceutical emulsions may also be multiple emulsions that are comprised of more than two phases such as, for example, in the case of oil-in-water-in-oil (o/w/o) and water-in-oil-in-water (w/o/w) emulsions. Such complex formulations often provide certain advantages that simple binary emulsions do not. Multiple emulsions in which individual oil droplets of an o/w emulsion enclose small water droplets constitute a w/o/w emulsion. Likewise a system of oil droplets enclosed in globules of water stabilized in an oily continuous phase provides an o/w/o emulsion.

Emulsions are characterized by little or no thermodynamic stability. Often, the dispersed or discontinuous phase of the emulsion is well dispersed into the external or continuous phase and maintained in this form through the means of emulsifiers or the viscosity of the formulation. Either of the phases of the emulsion may be a semisolid or a solid, as is the case of emulsion-style ointment bases and creams. Other means of stabilizing emulsions entail the use of emulsifiers that may be incorporated into either phase of the emulsion. Emulsifiers may broadly be classified into four categories: synthetic surfactants, naturally occurring emulsifiers, absorption bases, and finely dispersed solids (Idson, in Pharmaceutical Dosage Forms, Lieberman, Rieger and Banker (Eds.), 1988, Marcel Dekker, Inc., New York, N.Y., volume 1, p. 199).

Synthetic surfactants, also known as surface active agents, have found wide applicability in the formulation of emulsions and have been reviewed in the literature (Rieger, in Pharmaceutical Dosage Forms, Lieberman, Rieger and Banker (Eds.), 1988, Marcel Dekker, Inc., New York, N.Y., volume 1, p. 285; Idson, in Pharmaceutical Dosage Forms, Lieberman, Rieger and Banker (Eds.), Marcel Dekker, Inc., New York, N.Y., 1988, volume 1, p. 199). Surfactants are typically amphiphilic and comprise a hydrophilic and a hydrophobic portion. The ratio of the hydrophilic to the hydrophobic nature of the surfactant has been termed the hydrophile/lipophile balance (HLB) and is a valuable tool in categorizing and selecting surfactants in the preparation of formulations. Surfactants may be classified into different classes based on the nature of the hydrophilic group: nonionic, anionic, cationic and amphoteric (Rieger, in Pharmaceutical Dosage Forms, Lieberman, Rieger and Banker (Eds.), 1988, Marcel Dekker, Inc., New York, N.Y., volume 1, p. 285).

Naturally occurring emulsifiers used in emulsion formulations include lanolin, beeswax, phosphatides, lecithin and acacia. Absorption bases possess hydrophilic properties such that they can soak up water to form w/o emulsions yet retain their semisolid consistencies, such as anhydrous lanolin and hydrophilic petrolatum. Finely divided solids have also been used as good emulsifiers especially in combination with surfactants and in viscous preparations. These include polar inorganic solids, such as heavy metal hydroxides, nonswelling clays such as bentonite, attapulgite, hectorite, kaolin, montmorillonite, colloidal aluminum silicate and colloidal magnesium aluminum silicate, pigments and nonpolar solids such as carbon or glyceryl tristearate.

A large variety of non-emulsifying materials are also included in emulsion formulations and contribute to the properties of emulsions. These include fats, oils, waxes, fatty acids, fatty alcohols, fatty esters, humectants, hydrophilic colloids, preservatives and antioxidants (Block, in Pharmaceutical Dosage Forms, Lieberman, Rieger and Banker (Eds.), 1988, Marcel Dekker, Inc., New York, N.Y., volume 1, p. 335; Idson, in Pharmaceutical Dosage Forms, Lieberman, Rieger and Banker (Eds.), 1988, Marcel Dekker, Inc., New York, N.Y., volume 1, p. 199).

Hydrophilic colloids or hydrocolloids include naturally occurring gums and synthetic polymers such as polysaccharides (for example, acacia, agar, alginic acid, carrageenan, guar gum, karaya gum, and tragacanth), cellulose derivatives (for example, carboxymethylcellulose and carboxypropylcellulose), and synthetic polymers (for example, carbomers, cellulose ethers, and carboxyvinyl polymers). These disperse or swell in water to form colloidal solutions that stabilize emulsions by forming strong interfacial films around the dispersed-phase droplets and by increasing the viscosity of the external phase.

Since emulsions often contain a number of ingredients such as carbohydrates, proteins, sterols and phosphatides that may readily support the growth of microbes, these formulations often incorporate preservatives. Commonly used preservatives included in emulsion formulations include methyl paraben, propyl paraben, quaternary ammonium salts, benzalkonium chloride, esters of p-hydroxybenzoic acid, and boric acid. Antioxidants are also commonly added to emulsion formulations to prevent deterioration of the formulation. Antioxidants used may be free radical scavengers such as tocopherols, alkyl gallates, butylated hydroxyanisole, butylated hydroxytoluene, or reducing agents such as ascorbic acid and sodium metabisulfite, and antioxidant synergists such as citric acid, tartaric acid, and lecithin.

The application of emulsion formulations via dermatological, oral and parenteral routes and methods for their manufacture have been reviewed in the literature (Idson, in Pharmaceutical Dosage Forms, Lieberman, Rieger and Banker (Eds.), 1988, Marcel Dekker, Inc., New York, N.Y., volume 1, p. 199). Emulsion formulations for oral delivery have been very widely used because of ease of formulation, as well as efficacy from an absorption and bioavailability standpoint (Rosoff, in Pharmaceutical Dosage Forms, Lieberman, Rieger and Banker (Eds.), 1988, Marcel Dekker, Inc., New York, N.Y., volume 1, p. 245; Idson, in Pharmaceutical Dosage Forms, Lieberman, Rieger and Banker (Eds.), 1988, Marcel Dekker, Inc., New York, N.Y., volume 1, p. 199). Mineral-oil base laxatives, oil-soluble vitamins and high fat nutritive preparations are among the materials that have commonly been administered orally as o/w emulsions.

In one embodiment, the compositions of dsRNAs and nucleic acids are formulated as microemulsions. A microemulsion may be defined as a system of water, oil and amphiphile which is a single optically isotropic and thermodynamically stable liquid solution (Rosoff, in Pharmaceutical Dosage Forms, Lieberman, Rieger and Banker (Eds.), 1988, Marcel Dekker, Inc., New York, N.Y., volume 1, p. 245). Typically, microemulsions are systems that are prepared by first dispersing an oil in an aqueous surfactant solution and then adding a sufficient amount of a fourth component, generally an intermediate chain-length alcohol to form a transparent system. Therefore, microemulsions have also been described as thermodynamically stable, isotropically clear dispersions of two immiscible liquids that are stabilized by interfacial films of surface-active molecules (Leung and Shah, in: Controlled Release of Drugs: Polymers and Aggregate Systems, Rosoff, M., Ed., 1989, VCH Publishers, New York, pages 185-215). Microemulsions commonly are prepared via a combination of three to five components that include oil, water, surfactant, cosurfactant and electrolyte. Whether the microemulsion is of the water-in-oil (w/o) or an oil-in-water (o/w) type is dependent on the properties of the oil and surfactant used and on the structure and geometric packing of the polar heads and hydrocarbon tails of the surfactant molecules (Schott, in Remington's Pharmaceutical Sciences, Mack Publishing Co., Easton, Pa., 1985, p. 271).

The phenomenological approach utilizing phase diagrams has been extensively studied and has yielded a comprehensive knowledge, to one skilled in the art, of how to formulate microemulsions (Rosoff, in Pharmaceutical Dosage Forms, Lieberman, Rieger and Banker (Eds.), 1988, Marcel Dekker, Inc., New York, N.Y., volume 1, p. 245; Block, in Pharmaceutical Dosage Forms, Lieberman, Rieger and Banker (Eds.), 1988, Marcel Dekker, Inc., New York, N.Y., volume 1, p. 335). Compared to conventional emulsions, microemulsions offer the advantage of solubilizing water-insoluble drugs in a formulation of thermodynamically stable droplets that are formed spontaneously.

Surfactants used in the preparation of microemulsions include, but are not limited to, ionic surfactants, non-ionic surfactants, Brij 96, polyoxyethylene oleyl ethers, polyglycerol fatty acid esters, tetraglycerol monolaurate (ML310), tetraglycerol monooleate (MO310), hexaglycerol monooleate (PO310), hexaglycerol pentaoleate (PO500), decaglycerol monocaprate (MCA750), decaglycerol monooleate (M0750), decaglycerol sequioleate (SO750), decaglycerol decaoleate (DAO750), alone or in combination with cosurfactants. The cosurfactant, usually a short-chain alcohol such as ethanol, 1-propanol, and 1-butanol, serves to increase the interfacial fluidity by penetrating into the surfactant film and consequently creating a disordered film because of the void space generated among surfactant molecules. Microemulsions may, however, be prepared without the use of cosurfactants and alcohol-free self-emulsifying microemulsion systems are known in the art. The aqueous phase may typically be, but is not limited to, water, an aqueous solution of the drug, glycerol, PEG300, PEG400, polyglycerols, propylene glycols, and derivatives of ethylene glycol. The oil phase may include, but is not limited to, materials such as Captex 300, Captex 355, Capmul MCM, fatty acid esters, medium chain (C8-C12) mono, di, and tri-glycerides, polyoxyethylated glyceryl fatty acid esters, fatty alcohols, polyglycolized glycerides, saturated polyglycolized C8-C10 glycerides, vegetable oils and silicone oil.

Microemulsions are particularly of interest from the standpoint of drug solubilization and the enhanced absorption of drugs. Lipid based microemulsions (both o/w and w/o) have been proposed to enhance the oral bioavailability of drugs, including peptides (Constantinides et al., Pharmaceutical Research, 1994, 11, 1385-1390; Ritschel, Meth. Find. Exp. Clin. Pharmacol., 1993, 13, 205). Microemulsions afford advantages of improved drug solubilization, protection of drug from enzymatic hydrolysis, possible enhancement of drug absorption due to surfactant-induced alterations in membrane fluidity and permeability, ease of preparation, ease of oral administration over solid dosage forms, improved clinical potency, and decreased toxicity (Constantinides et al., Pharmaceutical Research, 1994, 11, 1385; Ho et al., J. Pharm. Sci., 1996, 85, 138-143). Often microemulsions may form spontaneously when their components are brought together at ambient temperature. This may be particularly advantageous when formulating thermolabile drugs, peptides or dsRNAs. Microemulsions have also been effective in the transdermal delivery of active components in both cosmetic and pharmaceutical applications. It is expected that the microemulsion compositions and formulations featured in the invention will facilitate the increased systemic absorption of dsRNAs and nucleic acids from the gastrointestinal tract, as well as improve the local cellular uptake of dsRNAs and nucleic acids within the gastrointestinal tract, vagina, buccal cavity and other areas of administration.

Microemulsions may also contain additional components and additives such as sorbitan monostearate (Grill 3), Labrasol, and penetration enhancers to improve the properties of the formulation and to enhance the absorption of the dsRNAs and nucleic acids featured in the invention. Penetration enhancers used in microemulsions may be classified as belonging to one of five broad categories—surfactants, fatty acids, bile salts, chelating agents, and non-chelating non-surfactants (Lee et al., Critical Reviews in Therapeutic Drug Carrier Systems, 1991, p. 92). Each of these classes has been discussed above.

Liposomes

There are many organized surfactant structures besides microemulsions that have been studied and used for the formulation of drugs. These include monolayers, micelles, bilayers and vesicles. Vesicles, such as liposomes, have attracted great interest because of their specificity and the duration of action they offer from the standpoint of drug delivery. As used herein, the term "liposome" means a vesicle composed of amphiphilic lipids arranged in a spherical bilayer or bilayers.

Liposomes are unilamellar or multilamellar vesicles which have a membrane formed from a lipophilic material and an aqueous interior. The aqueous portion contains the composition to be delivered. Cationic liposomes possess the advantage of being able to fuse to the cell wall. Non-cationic liposomes, although not able to fuse as efficiently with the cell wall, are taken up by macrophages in vivo.

In order to cross intact mammalian skin, lipid vesicles must pass through a series of fine pores, each with a diameter less than 50 nm, under the influence of a suitable transdermal gradient. Therefore, it is desirable to use a liposome which is highly deformable and able to pass through such fine pores.

Further advantages of liposomes include; liposomes obtained from natural phospholipids are biocompatible and biodegradable; liposomes can incorporate a wide range of water and lipid soluble drugs; liposomes can protect encapsulated drugs in their internal compartments from metabolism and degradation (Rosoff, in Pharmaceutical Dosage Forms, Lieberman, Rieger and Banker (Eds.), 1988, Marcel Dekker, Inc., New York, N.Y., volume 1, p. 245). Important considerations in the preparation of liposome formulations are the lipid surface charge, vesicle size and the aqueous volume of the liposomes.

Liposomes are useful for the transfer and delivery of active ingredients to the site of action. Because the liposomal membrane is structurally similar to biological membranes, when liposomes are applied to a tissue, the liposomes start to merge with the cellular membranes and as the merging of the liposome and cell progresses, the liposomal contents are emptied into the cell where the active agent may act.

Liposomal formulations have been the focus of extensive investigation as the mode of delivery for many drugs. There is growing evidence that for topical administration, liposomes present several advantages over other formulations. Such advantages include reduced side-effects related to high systemic absorption of the administered drug, increased accumulation of the administered drug at the desired target, and the ability to administer a wide variety of drugs, both hydrophilic and hydrophobic, into the skin.

Several reports have detailed the ability of liposomes to deliver agents including high-molecular weight DNA into the skin. Compounds including analgesics, antibodies, hormones and high-molecular weight DNAs have been administered to the skin. The majority of applications resulted in the targeting of the upper epidermis Liposomes fall into two broad classes. Cationic liposomes are positively charged liposomes which interact with the negatively charged DNA molecules to form a stable complex. The positively charged DNA/liposome complex binds to the negatively charged cell surface and is internalized in an endosome. Due to the acidic pH within the endosome, the liposomes are ruptured, releasing their contents into the cell cytoplasm (Wang et al., Biochem. Biophys. Res. Commun., 1987, 147, 980-985).

Liposomes which are pH-sensitive or negatively-charged, entrap DNA rather than complex with it. Since both the DNA and the lipid are similarly charged, repulsion rather than complex formation occurs. Nevertheless, some DNA is entrapped within the aqueous interior of these liposomes. pH-sensitive liposomes have been used to deliver DNA encoding the thymidine kinase gene to cell monolayers in culture. Expression of the exogenous gene was detected in the target cells (Zhou et al., Journal of Controlled Release, 1992, 19, 269-274).

One major type of liposomal composition includes phospholipids other than naturally-derived phosphatidylcholine. Neutral liposome compositions, for example, can be formed from dimyristoyl phosphatidylcholine (DMPC) or dipalmitoyl phosphatidylcholine (DPPC). Anionic liposome compositions generally are formed from dimyristoyl phosphatidylglycerol, while anionic fusogenic liposomes are formed primarily from dioleoyl phosphatidylethanolamine (DOPE). Another type of liposomal composition is formed from phosphatidylcholine (PC) such as, for example, soybean PC, and egg PC. Another type is formed from mixtures of phospholipid and/or phosphatidylcholine and/or cholesterol.

Several studies have assessed the topical delivery of liposomal drug formulations to the skin. Application of liposomes containing interferon to guinea pig skin resulted in a reduction of skin herpes sores while delivery of interferon via other means (e.g. as a solution or as an emulsion) were ineffective (Weiner et al., Journal of Drug Targeting, 1992, 2, 405-410). Further, an additional study tested the efficacy of interferon administered as part of a liposomal formulation to the administration of interferon using an aqueous system, and concluded that the liposomal formulation was superior to aqueous administration (du Plessis et al., Antiviral Research, 1992, 18, 259-265).

Non-ionic liposomal systems have also been examined to determine their utility in the delivery of drugs to the skin, in particular systems including non-ionic surfactant and cholesterol. Non-ionic liposomal formulations including Novasome™ I (glyceryl dilaurate/cholesterol/po-lyoxyethylene-10-stearyl ether) and Novasome™ II (glyceryl distearate/cholesterol/polyoxyethylene-10-stearyl ether) were used to deliver cyclosporin-A into the dermis of mouse skin. Results indicated that such non-ionic liposomal systems were effective in facilitating the deposition of cyclosporin-A into different layers of the skin (Hu et al. S. T. P. Pharma. Sci., 1994, 4, 6, 466).

Liposomes also include "sterically stabilized" liposomes, a term which, as used herein, refers to liposomes including one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome (A) includes one or more glycolipids, such as monosialoganglioside $G_{M1}$, or (B) is derivatized with one or more hydrophilic polymers, such as a polyethylene glycol (PEG) moiety. While not wishing to be bound by any particular theory, it is thought in the art that, at least for sterically stabilized liposomes containing gangliosides, sphingomyelin, or PEG-derivatized lipids, the enhanced circulation half-life of these sterically stabilized liposomes derives from a reduced uptake into cells of the reticuloendothelial system (RES) (Allen et al., FEBS Letters, 1987, 223, 42; Wu et al., Cancer Research, 1993, 53, 3765).

Various liposomes including one or more glycolipids are known in the art. Papahadjopoulos et al. (Ann. N.Y. Acad. Sci., 1987, 507, 64) reported the ability of monosialoganglioside $G_{M1}$, galactocerebroside sulfate and phosphatidylinositol to improve blood half-lives of liposomes. These findings were expounded upon by Gabizon et al. (Proc. Natl. Acad. Sci. U.S.A., 1988, 85, 6949). U.S. Pat. No. 4,837,028 and WO 88/04924, both to Allen et al., disclose liposomes including (1) sphingomyelin and (2) the ganglioside $G_{M1}$ or a galactocerebroside sulfate ester. U.S. Pat. No. 5,543,152 (Webb et al.) discloses liposomes including sphingomyelin. Liposomes including 1,2-sn-dimyristoylphosphat-idylcholine are disclosed in WO 97/13499 (Lim et al).

Many liposomes including lipids derivatized with one or more hydrophilic polymers, and methods of preparation thereof, are known in the art. Sunamoto et al. (Bull. Chem. Soc. Jpn., 1980, 53, 2778) described liposomes including a nonionic detergent, $2C_{12}15G$, that contains a PEG moiety. Illum et al. (FEBS Lett., 1984, 167, 79) noted that hydrophilic coating of polystyrene particles with polymeric glycols results in significantly enhanced blood half-lives. Synthetic phospholipids modified by the attachment of carboxylic groups of polyalkylene glycols (e.g., PEG) are described by Sears (U.S. Pat. Nos. 4,426,330 and 4,534,899). Klibanov et al. (FEBS Lett., 1990, 268, 235) described experiments demonstrating that liposomes including phosphatidylethanolamine (PE) derivatized with PEG or PEG stearate have significant increases in blood circulation half-lives. Blume et al. (Biochimica et Biophysica Acta, 1990, 1029, 91) extended such observations to other PEG-derivatized phospholipids, e.g., DSPE-PEG, formed from the combination of distearoylphosphatidylethanolamine (DSPE) and PEG. Liposomes having covalently bound PEG moieties on their external surface are described in European Patent No. EP 0 445 131 B1 and WO 90/04384 to Fisher. Liposome compositions containing 1-20 mole percent of PE derivatized with PEG, and methods of use thereof, are described by Woodle et al. (U.S. Pat. Nos. 5,013,556 and 5,356,633) and Martin et al. (U.S. Pat. No. 5,213,804 and European Patent No. EP 0 496 813 B1). Liposomes including a number of other lipid-polymer conjugates are disclosed in WO 91/05545 and U.S. Pat. No. 5,225,212 (both to Martin et al.) and in WO 94/20073 (Zalipsky et al.) Liposomes including PEG-modified ceramide lipids are described in WO 96/10391 (Choi et al). U.S. Pat. No. 5,540,935 (Miyazaki et al.) and U.S. Pat. No. 5,556,948 (Tagawa et al.) describe PEG-containing liposomes that can be further derivatized with functional moieties on their surfaces.

A limited number of liposomes including nucleic acids are known in the art. WO 96/40062 to Thierry et al. discloses methods for encapsulating high molecular weight nucleic acids in liposomes. U.S. Pat. No. 5,264,221 to Tagawa et al. discloses protein-bonded liposomes and asserts that the contents of such liposomes may include an dsRNA RNA. U.S. Pat. No. 5,665,710 to Rahman et al. describes certain methods of encapsulating oligodeoxynucleotides in liposomes. WO 97/04787 to Love et al. discloses liposomes including dsRNA dsRNAs targeted to the raf gene.

Transfersomes are yet another type of liposomes, and are highly deformable lipid aggregates which are attractive candidates for drug delivery vehicles. Transfersomes may be described as lipid droplets which are so highly deformable that they are easily able to penetrate through pores which are smaller than the droplet. Transfersomes are adaptable to the environment in which they are used, e.g. they are self-optimizing (adaptive to the shape of pores in the skin), self-repairing, frequently reach their targets without fragmenting, and often self-loading. To make transfersomes it is possible to add surface edge-activators, usually surfactants, to a standard liposomal composition. Transfersomes have been used to deliver serum albumin to the skin. The transfersome-mediated delivery of serum albumin has been shown to be as effective as subcutaneous injection of a solution containing serum albumin.

Surfactants find wide application in formulations such as emulsions (including microemulsions) and liposomes. The most common way of classifying and ranking the properties of the many different types of surfactants, both natural and synthetic, is by the use of the hydrophile/lipophile balance (HLB). The nature of the hydrophilic group (also known as the "head") provides the most useful means for categorizing the different surfactants used in formulations (Rieger, in Pharmaceutical Dosage Forms, Marcel Dekker, Inc., New York, N.Y., 1988, p. 285).

If the surfactant molecule is not ionized, it is classified as a nonionic surfactant. Nonionic surfactants find wide application in pharmaceutical and cosmetic products and are usable over a wide range of pH values. In general their HLB values range from 2 to about 18 depending on their structure. Nonionic surfactants include nonionic esters such as ethylene glycol esters, propylene glycol esters, glyceryl esters, polyglyceryl esters, sorbitan esters, sucrose esters, and ethoxylated esters. Nonionic alkanolamides and ethers such as fatty alcohol ethoxylates, propoxylated alcohols, and ethoxylated/propoxylated block polymers are also included in this class. The polyoxyethylene surfactants are the most popular members of the nonionic surfactant class.

If the surfactant molecule carries a negative charge when it is dissolved or dispersed in water, the surfactant is classified as anionic. Anionic surfactants include carboxylates such as soaps, acyl lactylates, acyl amides of amino acids, esters of sulfuric acid such as alkyl sulfates and ethoxylated alkyl sulfates, sulfonates such as alkyl benzene sulfonates, acyl isethionates, acyl taurates and sulfosuccinates, and phosphates. The most important members of the anionic surfactant class are the alkyl sulfates and the soaps.

If the surfactant molecule carries a positive charge when it is dissolved or dispersed in water, the surfactant is classified as cationic. Cationic surfactants include quaternary ammonium salts and ethoxylated amines. The quaternary ammonium salts are the most used members of this class.

If the surfactant molecule has the ability to carry either a positive or negative charge, the surfactant is classified as amphoteric. Amphoteric surfactants include acrylic acid derivatives, substituted alkylamides, N-alkylbetaines and phosphatides.

The use of surfactants in drug products, formulations and in emulsions has been reviewed (Rieger, in Pharmaceutical Dosage Forms, Marcel Dekker, Inc., New York, N.Y., 1988, p. 285).

Penetration Enhancers

In one embodiment, various penetration enhancers are used to effect the efficient delivery of nucleic acids, particularly dsRNAs, to the skin of animals. Most drugs are present in solution in both ionized and nonionized forms. However, usually only lipid soluble or lipophilic drugs readily cross cell membranes. It has been discovered that even non-lipophilic drugs may cross cell membranes if the membrane to be crossed is treated with a penetration enhancer. In addition to aiding the diffusion of non-lipophilic drugs across cell membranes, penetration enhancers also enhance the permeability of lipophilic drugs.

Penetration enhancers may be classified as belonging to one of five broad categories, i.e., surfactants, fatty acids, bile salts, chelating agents, and non-chelating non-surfactants (Lee et al., Critical Reviews in Therapeutic Drug Carrier Systems, 1991, p. 92). Each of the above mentioned classes of penetration enhancers are described below in greater detail.

Surfactants (or "surface-active agents") are chemical entities, which when dissolved in an aqueous solution, reduce the surface tension of the solution or the interfacial tension between the aqueous solution and another liquid, with the result that absorption of dsRNAs through the mucosa is enhanced. In addition to bile salts and fatty acids, these penetration enhancers include, for example, sodium lauryl sulfate, polyoxyethylene-9-lauryl ether and polyoxyethylene-20-cetyl ether) (Lee et al., Critical Reviews in Therapeutic Drug Carrier Systems, 1991, p. 92); and perfluorochemical emulsions, such as FC-43. Takahashi et al., J. Pharm. Pharmacol., 1988, 40, 252).

Fatty acids: Various fatty acids and their derivatives which act as penetration enhancers include, for example, oleic acid, lauric acid, capric acid (n-decanoic acid), myristic acid, palmitic acid, stearic acid, linoleic acid, linolenic acid, dicaprate, tricaprate, monoolein (1-monooleoyl-rac-glycerol), dilaurin, caprylic acid, arachidonic acid, glycerol 1-monocaprate, 1-dodecylazacycloheptan-2-one, acylcarnitines, acylcholines, $C_{1-10}$ alkyl esters thereof (e.g., methyl, isopropyl and t-butyl), and mono- and di-glycerides thereof (i.e., oleate, laurate, caprate, myristate, palmitate, stearate, linoleate, etc.) (Lee et al., Critical Reviews in Therapeutic Drug Carryier Systems, 1991, p. 92; Muranishi, Critical Reviews in Therapeutic Drug Carrier Systems, 1990, 7, 1-33; El Hariri et al., J. Pharm. Pharmacol., 1992, 44, 651-654).

Bile salts: The physiological role of bile includes the facilitation of dispersion and absorption of lipids and fat-soluble vitamins (Brunton, Chapter 38 in: Goodman & Gilman's The Pharmacological Basis of Therapeutics, 9th Ed., Hardman et al. Eds., McGraw-Hill, New York, 1996, pp. 934-935). Various natural bile salts, and their synthetic derivatives, act as penetration enhancers. Thus the term "bile salts" includes any of the naturally occurring components of bile as well as any of their synthetic derivatives. The bile salts include, for example, cholic acid (or its pharmaceutically acceptable sodium salt, sodium cholate), dehydrocholic acid (sodium dehydrocholate), deoxycholic acid (sodium deoxycholate), glucholic acid (sodium glucholate), glycholic acid (sodium glycocholate), glycodeoxycholic acid (sodium glycodeoxycholate), taurocholic acid (sodium taurocholate), taurodeoxycholic acid (sodium taurodeoxycholate), chenodeoxycholic acid (sodium chenodeoxycholate), ursodeoxycholic acid (UDCA), sodium tauro-24,25-dihydro-fusidate (STDHF), sodium glycodihydrofusidate and polyoxyethylene-9-lauryl ether (POE) (Lee et al., Critical Reviews in Therapeutic Drug Carrier Systems, 1991, page 92; Swinyard, Chapter 39 In: Remington's Pharmaceutical Sciences, 18th Ed., Gennaro, ed., Mack Publishing Co., Easton, Pa., 1990, pages 782-783; Muranishi, Critical Reviews in Therapeutic Drug Carrier Systems, 1990, 7, 1-33; Yamamoto et al., J. Pharm. Exp. Ther., 1992, 263, 25; Yamashita et al., J. Pharm. Sci., 1990, 79, 579-583).

"Chelating Agents" are defined as compounds that remove metallic ions from solution by forming complexes therewith, with the result that absorption of dsRNAs through the mucosa is enhanced. With regards to their use as penetration enhancers, chelating agents have the added advantage of also serving as DNase inhibitors, as most characterized DNA nucleases require a divalent metal ion for catalysis and are thus inhibited by chelating agents (Jarrett, J. Chromatogr., 1993, 618, 315-339). Chelating agents include but are not limited to disodium ethylenediaminetetraacetate (EDTA), citric acid, salicylates (e.g., sodium salicylate, 5-methoxysalicylate and homovanilate), N-acyl derivatives of collagen, laureth-9 and N-amino acyl derivatives of beta-diketones (enamines) (Lee et al., Critical Reviews in Therapeutic Drug Carrier Systems, 1991, page 92; Muranishi, Critical Reviews in Therapeutic Drug Carrier Systems, 1990, 7, 1-33; Buur et al., J. Control Rel., 1990, 14, 43-51).

Non-chelating non-surfactants: As used herein, non-chelating non-surfactant penetration enhancing compounds can be defined as compounds that demonstrate insignificant activity as chelating agents or as surfactants but that nonetheless enhance absorption of dsRNAs through the alimentary mucosa (Muranishi, Critical Reviews in Therapeutic Drug Carrier Systems, 1990, 7, 1-33). This class of penetration enhancers include, for example, unsaturated cyclic ureas, 1-alkyl- and 1-alkenylazacyclo-alkanone derivatives (Lee et al., Critical Reviews in Therapeutic Drug Carrier Systems, 1991, page 92); and non-steroidal anti-inflammatory agents such as diclofenac sodium, indomethacin and phenylbutazone (Yamashita et al., J. Pharm. Pharmacol., 1987, 39, 621-626).

Agents that enhance uptake of dsRNAs at the cellular level may also be added to the pharmaceutical and other compositions featured in the invention. For example, cationic lipids, such as lipofectin (Junichi et al, U.S. Pat. No. 5,705,188), cationic glycerol derivatives, and polycationic molecules, such as polylysine (Lollo et al., PCT Application WO 97/30731), are also known to enhance the cellular uptake of dsRNAs.

Other agents may be utilized to enhance the penetration of the administered nucleic acids, including glycols such as ethylene glycol and propylene glycol, pyrrols such as 2-pyrrol, azones, and terpenes such as limonene and menthone.

Carriers

Certain compositions featured herein also incorporate carrier compounds in the formulation. As used herein, "carrier compound" or "carrier" can refer to a nucleic acid, or analog thereof, which is inert (i.e., does not possess biological activity per se), but is recognized as a nucleic acid by in vivo processes that reduce the bioavailability of a nucleic acid having biological activity by, for example, degrading the biologically active nucleic acid or promoting its removal from circulation. The coadministration of a nucleic acid and a carrier compound, typically with an excess of the latter substance, can result in a substantial reduction of the amount of nucleic acid recovered in the liver, kidney or other extracirculatory reservoirs, presumably due to competition between the carrier compound and the nucleic acid for a common receptor. For example, the recovery of a partially phosphorothioate dsRNA in hepatic tissue can be reduced when it is coadministered with polyinosinic acid, dextran sulfate, polycytidic acid or 4-acetamido-4'isothiocyano-stilbene-2,2'-disulfonic acid (Miyao et al., DsRNA Res. Dev., 1995, 5, 115-121; Takakura et al., DsRNA & Nucl. Acid Drug Dev., 1996, 6, 177-183).

Excipients

In contrast to a carrier compound, a "pharmaceutical carrier" or "excipient" is a pharmaceutically acceptable solvent, suspending agent or any other pharmacologically inert vehicle for delivering one or more nucleic acids to an animal. The excipient may be liquid or solid and is selected, with the planned manner of administration in mind, so as to provide for the desired bulk, consistency, etc., when combined with a nucleic acid and the other components of a given pharmaceutical composition. Typical pharmaceutical carriers include, but are not limited to, binding agents (e.g., pregelatinized maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrants (e.g., starch, sodium starch glycolate, etc.); and wetting agents (e.g., sodium lauryl sulphate, etc).

Pharmaceutically acceptable organic or inorganic excipients suitable for non-parenteral administration, and that do not deleteriously react with nucleic acids, can also be used to formulate the compositions featured in the present invention. Suitable pharmaceutically acceptable carriers include, but are not limited to, water, salt solutions, alcohols, polyethylene glycols, gelatin, lactose, amylose, magnesium stearate, talc, silicic acid, viscous paraffin, hydroxymethylcellulose, polyvinylpyrrolidone and the like.

Formulations for topical administration of nucleic acids may include sterile and non-sterile aqueous solutions, non-aqueous solutions in common solvents such as alcohols, or solutions of the nucleic acids in liquid or solid oil bases. The solutions may also contain buffers, diluents and other suitable additives. Pharmaceutically acceptable organic or inorganic excipients suitable for non-parenteral administration which do not deleteriously react with nucleic acids can be used.

Suitable pharmaceutically acceptable excipients include, but are not limited to, water, salt solutions, alcohol, polyethylene glycols, gelatin, lactose, amylose, magnesium stearate, talc, silicic acid, viscous paraffin, hydroxymethylcellulose, polyvinylpyrrolidone and the like.

Other Components

The compositions featured in the invention may additionally contain other adjunct components conventionally found in pharmaceutical compositions, at their art-established usage levels. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions featured in the present invention, such as dyes, flavoring agents, preservatives, antioxidants, opacifiers, thickening agents and stabilizers. However, such materials, when added, should not unduly interfere with the biological activities of the components of the compositions featured in the invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

Aqueous suspensions may contain substances which increase the viscosity of the suspension including, for example, sodium carboxymethylcellulose, sorbitol and/or dextran. The suspension may also contain stabilizers.

Certain embodiments featured in the invention provide pharmaceutical compositions containing (a) one or more antisense compounds and (b) one or more other therapeutic agents which function by a non-antisense mechanism. For example, the one or more other therapeutic agents include antibiotic or antiviral agents. Exemplary antibiotics include, e.g., amphotericin B, norfloxacin, miconazole nitrate, ofloxacin, idoxuridine, chloramphenicol, colistin sodium methanesulfonate, carbenicillin sodium, beta-lactam antibiotics, cefoxitin, n-formanidolthienamycin and other thienamycin derivatives, tetracyclines, neomycin, carbenicillin, colistin, penicillin G, polymyxin B, vancomycin, cefazolin, cephaloridine, chibrorifamycin, gramicidin, bacitracin and sulfonamides. Exemplary antiviral agents include, e.g., acyclovir and interferon. For the treatment of autoimmune disease the one or more other therapeutic agents can include, e.g., interferon beta (e.g., IFNbeta-1a and IFN-1b, gliatriamer acetate (Copaxone), cyclophosphamide, methotrexate, azathioprine (Imuran), cladribine (Leustatin), cyclosporine, mitoxantrone, and glucocorticoids (e.g., adrenocorticotropic hormone (ACTH), methylprednisolone, and dexamethasone). For treatment of Graves' disease, for example, the additional therapeutic agent can be, e.g., an antithyroid drug, such as propylthiouracil (PTU) or methimazole. The invention also includes methods of treating a disorder described herein by administration of a dsRNA described herein and one or more other therapeutic agents which function by a non-antisense mechanism, e.g., one or more of the agents listed above. The agents can be administered in a single formulation or may be administered separately, at the same or at different times.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Suitable compounds typically exhibit high therapeutic indices.

The data obtained from cell culture assays and animal studies can be used in formulation a range of dosage for use in humans. The dosage of compositions featured in the invention lies generally within a range of circulating concentrations that include the ED50 with little or no toxicity. The dosage may vary within this range depending upon the dosage form employed and the route of administration utilized. For any compound used in the methods featured in the invention, the therapeutically effective dose can be estimated initially from cell culture assays. A dose may be formulated in animal models to achieve a circulating plasma concentration range of the compound or, when appropriate, of the polypeptide product of a target sequence (e.g., achieving a decreased concentration of the polypeptide) that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

In addition to their administration individually or as a plurality, as discussed above, the dsRNAs featured in the invention can be administered in combination with other known agents effective in treatment of pathological processes mediated by CD45 expression. In any event, the administering physician can adjust the amount and timing of dsRNA administration on the basis of results observed using standard measures of efficacy known in the art or described herein.

Methods for Treating Diseases Caused by Expression of the CD45 Gene

In one embodiment, the invention provides a method for treating a subject having a pathological condition mediated by the expression of the CD45 gene, such as an autoimmune disease or an infectious disease. In this embodiment, the dsRNA acts as a therapeutic agent for controlling the expression of the CD45 protein. The method includes administering a pharmaceutical composition featured in the invention to the patient (e.g., human), such that expression of the CD45 gene is silenced. Because of their high specificity, the dsRNAs featured in the invention specifically target mRNAs of the CD45 gene.

As used herein, the term "CD45-mediated condition or disease" and related terms and phrases refer to a condition or disorder characterized by unwanted or inappropriate, e.g., abnormal CD45 activity. Inappropriate CD45 functional activity might arise as the result of CD45 expression in cells which normally do not express CD45, increased CD45 expression and/or activity (leading to, e.g., autoimmune disorders and diseases, or increased susceptibility to disease). A CD45-mediated condition or disease may be completely or partially mediated by inappropriate CD45 functional activity which may result by way of inappropriate activation of CD45. Regardless, a CD45-mediated condition or disease is one in which modulation of CD45 via RNA interference results in some effect on the underlying condition or disorder (e.g., a CD45 inhibitor results in some improvement in patient well-being in at least some patients).

The anti-CD45 dsRNAs featured in the present invention may be used to treat or diagnose an infection or immune disorder in a subject. The methods include administering to a subject an anti-CD45 dsRNA in an amount effective to treat an infectious disease or autoimmune disorder.

Pathological processes refer to a category of biological processes that produce a deleterious effect. For example, unregulated expression of CD45 is associated with autoimmunity and infectious disease. A compound featured in the invention can typically modulate a pathological process when the compound reduces the degree or severity of the process. For instance, autoimmunity or an infection may be prevented or related pathological processes can be modulated by the administration of compounds that reduce or modulate in some way the expression or at least one activity CD45.

The dsRNA molecules featured herein may, therefore, be used to treat an autoimmune or infectious disease. Autoimmune diseases that can be treated with a dsRNA that targets CD45 include, but are not limited to, Graves' disease, Hashimoto's thyroiditis, multiple sclerosis, and systemic sclerosis. In one embodiment, a dsRNA targeting CD45 is administered to a patient who has received an organ transplant, such as to reduce the risk of damage to the organ (e.g., from ischemia and reperfusion, such as caused by an inflammatory response) and the risk of organ rejection. Infectious diseases that can be treated with a dsRNA that targets CD45 include but are not limited to influenza, anthrax, Ebola, human immunodeficiency virus (HIV), vesicular stomatitis virus (VSV), rabies, Mokola, Rous sarcoma virus, and hepatitis, such as hepatitis A, B and C strains.

The pharmaceutical compositions encompassed by the invention may be administered by any means known in the art including, but not limited to oral or parenteral routes, including intravenous, intramuscular, intraarticular, intraperitoneal, subcutaneous, intravitreal, transdermal, airway (aerosol), nasal, rectal, vaginal and topical (including buccal and sublingual) administration, and epidural administration. In some embodiments, the pharmaceutical compositions are administered intraveneously by infusion or injection.

Before administration of a full dose of a dsRNA targeting CD45, a patient can be administered a smaller dose, such as a 5% infusion reaction, and monitored for adverse effects, such as an allergic reaction. In another example, the patient can be monitored for unwanted immunostimulatory effects, such as increased cytokine (e.g., TNF-alpha or INF-alpha) levels.

Many CD45-associated diseases and disorders are hereditary. Therefore, a patient in need of a dsRNA targeting CD45 can be identified by taking a family history. A healthcare provider, such as a doctor, nurse, or family member, can take a family history before prescribing or administering a dsRNA. A DNA test may also be performed on the patient to identify a mutation in the target gene, before a dsRNA is administered to the patient.

Methods for Inhibiting Expression of the CD45 Gene

In yet another aspect, the invention provides a method for inhibiting the expression of the CD45 gene in a mammal. The method includes administering a CD45 dsRNA to the mammal such that expression of the target CD45 gene is silenced. Because of their high specificity, the dsRNAs specifically target RNAs (primary or processed) of the target CD45 gene. Compositions and methods for inhibiting the expression of the CD45 gene using dsRNAs can be performed as described elsewhere herein.

In one embodiment, the method includes administering a composition including a dsRNA, wherein the dsRNA includes a nucleotide sequence which is complementary to at least a part of an RNA transcript of the CD45 gene of the mammal to be treated. When the organism to be treated is a mammal such as a human, the composition may be administered by any means known in the art including, but not limited to oral or parenteral routes, including intravenous, intramuscular, intraarticular, intracranial, subcutaneous, intravitreal, transdermal, airway (aerosol), nasal, rectal, vaginal and topical (including buccal and sublingual) administration. In some embodiments, the compositions are administered by intraveneous infusion or injection.

TABLE 1

Target positions of duplex dsRNAs

| Duplex Name | ID # | Human Reference NM_002838.2 pos. in 23 mer | SEQ ID NO: | sequence of total 23-mer target site |
|---|---|---|---|---|
| AD-14008 | 69 | 2206-2228 | 97 | CAGAAUAAAAACCGUUAUGUUGA |
| AD-14009 | 225 | 2213-2235 | 98 | AAAACCGUUAUGUUGACAUUCUU |
| AD-14010 | 211 | 1927-1949 | 99 | UUUCUGAUUAUUGUGACAUCAAU |
| AD-14011 | 224 | 2210-2232 | 100 | AUAAAACCGUUAUGUUGACAUU |
| AD-14012 | 233 | 2326-2348 | 101 | GAACCCAGGAAAUACAUUGCUGC |
| AD-14013 | 222 | 2204-2226 | 102 | ACCAGAAUAAAAACCGUUAUGUU |
| AD-14014 | 223 | 2205-2227 | 103 | CCAGAAUAAAAACCGUUAUGUUG |
| AD-14015 | 235 | 2409-2431 | 104 | CACAGUUAUUGUCAUGGUCACUC |
| AD-14016 | 454 | 2207-2229 | 105 | AGAAUAAAAACCGUUAUGUUGAC |
| AD-14017 | 463 | 2329-2351 | 106 | CCCAGGAAAUACAUUGCUGCACA |

TABLE 1-continued

Target positions of duplex dsRNAs

| Duplex Name | ID # | Human Reference NM_002838.2 pos. in 23 mer | SEQ ID NO: | sequence of total 23-mer target site |
|---|---|---|---|---|
| AD-14018 | 1389 | 2212-2234 | 107 | AAAAACCGUUAUGUUGACAUUCU |
| AD-14019 | 610 | 2211-2233 | 108 | UAAAAACCGUUAUGUUGACAUUC |
| AD-14020 | 1094 | 2215-2237 | 109 | AACCGUUAUGUUGACAUUCUUCC |
| AD-14021 | 611 | 2214-2236 | 110 | AAACCGUUAUGUUGACAUUCUUC |
| AD-14022 | 1388 | 2209-2231 | 111 | AAUAAAAACCGUUAUGUUGACAU |
| AD-14023 | 1095 | 2216-2238 | 112 | ACCGUUAUGUUGACAUUCUUCCU |
| AD-14024 | 1147 | 2408-2430 | 113 | CCACAGUUAUUGUCAUGGUCACU |
| AD-14025 | 725 | 1929-1951 | 114 | UCUGAUUAUUGUGACAUCAAUAG |
| AD-14026 | 1364 | 1930-1952 | 115 | CUGAUUAUUGUGACAUCAAUAGC |
| AD-14027 | 1124 | 2330-2352 | 116 | CCAGGAAAUACAUUGCUGCACAA |
| AD-14028 | 1050 | 2028-2050 | 117 | UGUUGAAAGGGAUGAUGAAAAAC |
| AD-14029 | 609 | 2208-2230 | 118 | GAAUAAAAACCGUUAUGUUGACA |
| AD-14030 | 724 | 1928-1950 | 119 | UUCUGAUUAUUGUGACAUCAAUA |
| AD-14031 | 1123 | 2327-2349 | 120 | AACCCAGGAAAUACAUUGCUGCA |
| AD-14032 | 1125 | 2331-2353 | 121 | CAGGAAAUACAUUGCUGCACAAG |
| AD-14033 | 1146 | 2407-2429 | 122 | GCCACAGUUAUUGUCAUGGUCAC |
| AD-14034 | 1403 | 2436-2458 | 123 | UGAAGAAGGAAACAGGAACAAGU |
| AD-14035 | 1365 | 1931-1953 | 124 | UGAUUAUUGUGACAUCAAUAGCC |
| AD-14036 | 1394 | 2328-2350 | 125 | ACCCAGGAAAUACAUUGCUGCAC |
| AD-14037 | 1154 | 2431-2453 | 126 | CGAUGUGAAGAAGGAAACAGGAA |
| AD-14038 | 1022 | 1932-1954 | 127 | GAUUAUUGUGACAUCAAUAGCCC |
| AD-14039 | 1121 | 2324-2346 | 128 | AAGAACCCAGGAAAUACAUUGCU |
| AD-14040 | 1122 | 2325-2347 | 129 | AGAACCCAGGAAAUACAUUGCUG |
| AD-14041 | 760 | 2405-2427 | 130 | AAGCCACAGUUAUUGUCAUGGUC |
| AD-14042 | 1401 | 2429-2451 | 131 | CUCGAUGUGAAGAAGGAAACAGG |
| AD-14043 | 1153 | 2430-2452 | 132 | UCGAUGUGAAGAAGGAAACAGGA |
| AD-14044 | 1402 | 2432-2454 | 133 | GAUGUGAAGAAGGAAACAGGAAC |
| AD-14045 | 1155 | 2433-2455 | 134 | AUGUGAAGAAGGAAACAGGAACA |
| AD-14046 | 744 | 2217-2239 | 135 | CCGUUAUGUUGACAUUCUUCCUU |
| AD-14047 | 1701 | 2406-2428 | 136 | AGCCACAGUUAUUGUCAUGGUCA |
| AD-14048 | 1704 | 2439-2461 | 137 | AGAAGGAAACAGGAACAAGUGUG |
| AD-14049 | 1833 | 2435-2457 | 138 | GUGAAGAAGGAAACAGGAACAAG |
| AD-14050 | 1564 | 2133-2155 | 139 | UCUGGCUGAAUUUCAGAGCAUCC |
| AD-14051 | 1657 | 2027-2049 | 140 | UUGUUGAAAGGGAUGAUGAAAAA |
| AD-14052 | 1673 | 2132-2154 | 141 | UUCUGGCUGAAUUUCAGAGCAUC |
| AD-14053 | 1648 | 1926-1948 | 142 | AUUUCUGAUUAUUGUGACAUCAA |

TABLE 1-continued

Target positions of duplex dsRNAs

| Duplex Name | ID # | Human Reference NM_002838.2 pos. in 23 mer | SEQ ID NO: | sequence of total 23-mer target site |
|---|---|---|---|---|
| AD-14054 | 1703 | 2437-2459 | 143 | GAAGAAGGAAACAGGAACAAGUG |
| AD-14055 | 1647 | 1925-1947 | 144 | CAUUUCUGAUUAUUGUGACAUCA |

TABLE 2

Sense and Antisense sequences of duplex dsRNAs

| Duplex Name | SEQ ID NO: | Name | Sense strand sequence (5' to 3') Double overhang design | SEQ ID NO: | Name | Antisense strand sequence (5' to 3') Double overhang design |
|---|---|---|---|---|---|---|
| AD-14008 | 1 | A22737 | GAAuAAAAAccGuuAuGuuTsT | 2 | A22738 | AAcAuAACGGUUUUuAUUCTsT |
| AD-14009 | 3 | A22739 | AAccGuuAuGuuGAcAuucTsT | 4 | A22740 | GAAUGUcAAcAuAACGGUUUTsT |
| AD-14010 | 5 | A22741 | ucuGAuuAuuGuGAcAucATsT | 6 | A22742 | UGAUGUcAcAAuAAUcAGATsT |
| AD-14011 | 7 | A22743 | AAAAccGuuAuGuuGAcATsT | 8 | A22744 | UGUcAAcAuAACGGUUUUUTsT |
| AD-14012 | 9 | A22745 | AcccAGGAAAuAcAuuGcuTsT | 10 | A22746 | AGcAAUGuAUUUCCUGGGUTsT |
| AD-14013 | 11 | A22747 | cAGAAuAAAAAccGuuAuGTsT | 12 | A22748 | cAuAACGGUUUUuAUUCUGTsT |
| AD-14014 | 13 | A22749 | AGAAuAAAAAccGuuAuGuTsT | 14 | A22750 | AcAuAACGGUUUUuAUUCUTsT |
| AD-14015 | 15 | A22751 | cAGuuAuuGucAuGGucAcTsT | 16 | A22752 | GUGACcAUGAcAAuAACUGTsT |
| AD-14016 | 17 | A22753 | AAuAAAAAccGuuAuGuuGTsT | 18 | A22754 | cAAcAuAACGGUUUUuAUUTsT |
| AD-14017 | 19 | A22755 | cAGGAAAuAcAuuGcuGcATsT | 20 | A22756 | UGcAGcAAUGuAUUUCCUGTsT |
| AD-14018 | 21 | A22757 | AAAccGuuAuGuuGAcAuuTsT | 22 | A22758 | AAUGUcAAcAuAACGGUUUTsT |
| AD-14019 | 23 | A22759 | AAAAccGuuAuGuuGAcAuTsT | 24 | A22760 | AUGUcAAcAuAACGGUUUUTsT |
| AD-14020 | 25 | A22761 | ccGuuAuGuuGAcAuucuuTsT | 26 | A22762 | AAGAAUGUcAAcAuAACGGTsT |
| AD-14021 | 27 | A22763 | AccGuuAuGuuGAcAuucuTsT | 28 | A22764 | AGAAUGUcAAcAuAACGGUTsT |
| AD-14022 | 29 | A22765 | uAAAAAccGuuAuGuuGAcTsT | 30 | A22766 | GUcAAcAuAACGGUUUUuATsT |
| AD-14023 | 31 | A22767 | cGuuAuGuuGAcAuucuucTsT | 32 | A22768 | GAAGAAUGUcAAcAuAACGTsT |
| AD-14024 | 33 | A22769 | AcAGuuAuuGucAuGGucATsT | 34 | A22770 | UGACcAUGAcAAuAACUGUTsT |
| AD-14025 | 35 | A22771 | uGAuuAuuGuGAcAucAAuTsT | 36 | A22772 | AUUGAUGUcAcAAuAAUcATsT |
| AD-14026 | 37 | A22773 | GAuuAuuGuGAcAucAAuATsT | 38 | A22774 | uAUUGAUGUcAcAAuAAUCTsT |
| AD-14027 | 39 | A22775 | AGGAAAuAcAuuGcuGcAcTsT | 40 | A22776 | GUGcAGcAAUGuAUUUCCUTsT |
| AD-14028 | 41 | A22777 | uuGAAAGGGAuGAuGAAAATsT | 42 | A22778 | UUUUcAUcAUCCCUUUcAATsT |
| AD-14029 | 43 | A22779 | AuAAAAAccGuuAuGuuGATsT | 44 | A22780 | UcAAcAuAACGGUUUUuAUTsT |
| AD-14030 | 45 | A22781 | cuGAuuAuuGuGAcAucAATsT | 46 | A22782 | UUGAUGUcAcAAuAAUcAGTsT |
| AD-14031 | 47 | A22783 | cccAGGAAAuAcAuuGcuGTsT | 48 | A22784 | cAGcAAUGuAUUUCCUGGGTsT |
| AD-14032 | 49 | A22785 | GGAAAuAcAuuGcuGcAcATsT | 50 | A22786 | UGUGcAGcAAUGuAUUUCCTsT |
| AD-14033 | 51 | A22787 | cAcAGuuAuuGucAuGGucTsT | 52 | A22788 | GACcAUGAcAAuAACUGUGTsT |
| AD-14034 | 53 | A22789 | AAGAAGGAAAcAGGAAcAATsT | 54 | A22790 | UuGUUCCuGUUUCCUUCUUTsT |
| AD-14035 | 55 | A22791 | AuuAuuGuGAcAucAAuAGTsT | 56 | A22792 | CuAUUGAUGUcAcAAuAAUTsT |

TABLE 2-continued

Sense and Antisense sequences of duplex dsRNAs

| Duplex Name | SEQ ID NO:Name | Sense strand sequence (5' to 3') Double overhang design | SEQ ID NO:Name | Antisense strand sequence (5' to 3') Double overhang design |
|---|---|---|---|---|
| AD-14036 | 57 A22793 | ccAGGAAAuAcAuuGcuGcTsT | 58 A22794 | GcAGcAAUGuAUUUCCUGGTsT |
| AD-14037 | 59 A22795 | AuGuGAAGAAGGAAAcAGGTsT | 60 A22796 | CCUGUUUCCUUCUUcAcAUTsT |
| AD-14038 | 61 A22797 | uuAuuGuGAcAucAAuAGcTsT | 62 A22798 | GCuAUUGAUGUcAcAAuAATsT |
| AD-14039 | 63 A22799 | GAAcccAGGAAAuAcAuuGTsT | 64 A22800 | cAAUGuAUUUCCUGGGUUCTsT |
| AD-14040 | 65 A22801 | AAcccAGGAAAuAcAuuGcTsT | 66 A22802 | GcAAUGuAUUUCCUGGGUUTsT |
| AD-14041 | 67 A22803 | GccAcAGuuAuuGucAuGGTsT | 68 A22804 | CcAUGAcAAuAACUGUGGCTsT |
| AD-14042 | 69 A22805 | cGAuGuGAAGAAGGAAAcATsT | 70 A22806 | UGUUUCCUUCUUcAcAUCGTsT |
| AD-14043 | 71 A22807 | GAuGuGAAGAAGGAAAcAGTsT | 72 A22808 | CUGUUUCCUUCUUcAcAUCTsT |
| AD-14044 | 73 A22809 | uGuGAAGAAGGAAAcAGGATsT | 74 A22810 | UCCUGUUUCCUUCUUcAcATsT |
| AD-14045 | 75 A22811 | GuGAAGAAGGAAAcAGGAATsT | 76 A22812 | UUCCUGUUUCCUUCUUcACTsT |
| AD-14046 | 77 A22813 | GuuAuGuuGAcAuucuuccTsT | 78 A22814 | GGAAGAAUGUcAAcAuAACTsT |
| AD-14047 | 79 A22815 | ccAcAGuuAuuGucAuGGuTsT | 80 A22816 | ACcAUGAcAAuAACUGUGGTsT |
| AD-14048 | 81 A22817 | AAGGAAAcAGGAAcAAGuTsT | 82 A22818 | cACUUGUUCCUGUUUCCUUTsT |
| AD-14049 | 83 A22819 | GAAGAAGGAAAcAGGAAcATsT | 84 A22820 | uGUUCCuGUUUCCUUCUUCTsT |
| AD-14050 | 85 A22821 | uGGcuGAAuuucAGAGcAuTsT | 86 A22822 | AUGCUCUGAAAUUcAGCcATsT |
| AD-14051 | 87 A22823 | GuuGAAAGGGAuGAuGAAATsT | 88 A22824 | UUUcAUcAUCCCUUUcAACTsT |
| AD-14052 | 89 A22825 | cuGGcuGAAuuucAGAGcATsT | 90 A22826 | UGCUCUGAAAUUcAGCcAGTsT |
| AD-14053 | 91 A22827 | uucuGAuuAuuGuGAcAucTsT | 92 A22828 | GAUGUcAcAAuAAUcAGAATsT |
| AD-14054 | 93 A22829 | AGAAGGAAAcAGGAAcAAGTsT | 94 A22830 | CUuGUUCCuGUUUCCUUCUTsT |
| AD-14055 | 95 A22831 | uuucuGAuuAuuGuGAcAuTsT | 96 A22832 | AUGUcAcAAuAAUcAGAAATsT |

TABLE 3

Efficacy of duplex dsRNAs

| Duplex Name | Percent Inhibition[a] | SD[b] | IC20 (nM) (FACS) | IC50 (nM) (FACS) | IC80 (nM) (FACS) | IC20 (nM) (bDNA) | IC50 (nM) (bDNA) | IC80 (nM) (bDNA) |
|---|---|---|---|---|---|---|---|---|
| AD-14008 | 86% | 1% | 0.8895931 | #N/A | #N/A | 0.03996853 | 0.2361971 | #N/A |
| AD-14009 | 34% | 2% | | | | | | |
| AD-14010 | 38% | 3% | | | | | | |
| AD-14011 | 11% | 4% | | | | | | |
| AD-14012 | 62% | 5% | | | | | | |
| AD-14013 | 60% | 1% | | | | | | |
| AD-14014 | 10% | 8% | | | | | | |
| AD-14015 | 71% | 3% | | | | | | |
| AD-14016 | 16% | 10% | | | | | | |
| AD-14017 | 46% | 6% | | | | | | |
| AD-14018 | 84% | 0% | | | | 0.01773181 | 0.12385771 | #N/A |
| AD-14019 | 50% | 6% | | | | | | |
| AD-14020 | 75% | 3% | | | | | | |
| AD-14021 | 83% | 5% | 0.05351334 | 0.28749645 | #N/A | 0.00767305 | 0.06871733 | 3.50954466 |
| AD-14022 | 18% | 9% | | | | | | |
| AD-14023 | 82% | 3% | 0.16806395 | 1.15022087 | #N/A | 0.01854289 | 0.18153564 | 42.4598925 |
| AD-14024 | 45% | 8% | | | | | | |
| AD-14025 | 72% | 3% | | | | | | |
| AD-14026 | 68% | 4% | | | | | | |
| AD-14027 | 20% | 2% | | | | | | |

TABLE 3-continued

Efficacy of duplex dsRNAs

| Duplex Name | Percent Inhibition[a] | SD[b] | IC20 (nM) (FACS) | IC50 (nM) (FACS) | IC80 (nM) (FACS) | IC20 (nM) (bDNA) | IC50 (nM) (bDNA) | IC80 (nM) (bDNA) |
|---|---|---|---|---|---|---|---|---|
| AD-14028 | 79% | 3% | | | | 0.04248737 | 0.28602921 | #N/A |
| AD-14029 | 54% | 1% | | | | | | |
| AD-14030 | 74% | 3% | | | | | | |
| AD-14031 | 79% | 4% | | | | 0.6082823 | 1.9630781 | #N/A |
| AD-14032 | 61% | 10% | | | | | | |
| AD-14033 | 23% | 6% | | | | | | |
| AD-14034 | 55% | 4% | | | | | | |
| AD-14035 | 25% | 0% | | | | | | |
| AD-14036 | 63% | 2% | | | | | | |
| AD-14037 | 78% | 7% | | | | | | |
| AD-14038 | 12% | 1% | | | | | | |
| AD-14039 | 33% | 5% | | | | | | |
| AD-14040 | 17% | 3% | | | | | | |
| AD-14041 | 32% | 0% | | | | | | |
| AD-14042 | 78% | 4% | | | | 0.00990567 | 0.08334966 | #N/A |
| AD-14043 | 44% | 5% | | | | | | |
| AD-14044 | 59% | 6% | | | | | | |
| AD-14045 | 58% | 4% | | | | | | |
| AD-14046 | 50% | 5% | | | | | | |
| AD-14047 | 65% | 2% | | | | | | |
| AD-14048 | 12% | 4% | | | | | | |
| AD-14049 | 72% | 2% | | | | | | |
| AD-14050 | 52% | 9% | | | | | | |
| AD-14051 | 64% | 3% | | | | | | |
| AD-14052 | 89% | 4% | 0.06652968 | 0.30445773 | #N/A | 0.00543153 | 0.04500437 | 1.02650598 |
| AD-14053 | 78% | 3% | | | | 0.01679891 | 0.14666108 | #N/A |
| AD-14054 | 70% | 8% | | | | | | |
| AD-14055 | 26% | 3% | | | | | | |

[a]Percent inhibition of CD45 expression (relative to irrelevant control siRNA-treated cells; mean of three screens); by bDNA assay, 50 nM in P388D1.
[b]Standard Deviation (mean of three screens)

TABLE 4

Exemplary unmodified dsRNAs targeting CD45.

| position of 5' base on transcript NM_002838.2 | SEQ ID NO: | Sense strand sequence (5' to 3') Double overhang Design | SEQ ID NO: | Antisense strand sequence (5' to 3') Double overhang design |
|---|---|---|---|---|
| 2208 | 147 | GAAUAAAAACCGUUAUGUU | 148 | AACAUAACGGUUUUUAUUC |
| 2215 | 149 | AACCGUUAUGUUGACAUUC | 150 | GAAUGUCAACAUAACGGUU |
| 1929 | 151 | UCUGAUUAUUGUGACAUCA | 152 | UGAUGUCACAAUAAUCAGA |
| 2212 | 153 | AAAAACCGUUAUGUUGACA | 154 | UGUCAACAUAACGGUUUUU |
| 2328 | 155 | ACCCAGGAAAUACAUUGCU | 156 | AGCAAUGUAUUUCCUGGGU |
| 2206 | 157 | CAGAAUAAAAACCGUUAUG | 158 | CAUAACGGUUUUUAUUCUG |
| 2207 | 159 | AGAAUAAAAACCGUUAUGU | 160 | ACAUAACGGUUUUUAUUCU |
| 2411 | 161 | CAGUUAUUGUCAUGGUCAC | 162 | GUGACCAUGACAAUAACUG |
| 2209 | 163 | AAUAAAAACCGUUAUGUUG | 164 | CAACAUAACGGUUUUUAUU |
| 2331 | 165 | CAGGAAAUACAUUGCUGCA | 166 | UGCAGCAAUGUAUUUCCUG |
| 2214 | 167 | AAACCGUUAUGUUGACAUU | 168 | AAUGUCAACAUAACGGUUU |
| 2213 | 169 | AAAACCGUUAUGUUGACAU | 170 | AUGUCAACAUAACGGUUUU |
| 2217 | 171 | CCGUUAUGUUGACAUUCUU | 172 | AAGAAUGUCAACAUAACGG |
| 2216 | 173 | ACCGUUAUGUUGACAUUCU | 174 | AGAAUGUCAACAUAACGGU |
| 2211 | 175 | UAAAAACCGUUAUGUUGAC | 176 | GUCAACAUAACGGUUUUUA |

TABLE 4-continued

Exemplary unmodified dsRNAs targeting CD45.

| position of 5' base on transcript NM_002838.2 | Sense strand SEQ ID NO: | Sense strand sequence (5' to 3') Double overhang Design | Antisense strand SEQ ID NO: | Antisense strand sequence (5' to 3') Double overhang design |
|---|---|---|---|---|
| 2218 | 177 | CGUUAUGUUGACAUUCUUC | 178 | GAAGAAUGUCAACAUAACG |
| 2410 | 179 | ACAGUUAUUGUCAUGGUCA | 180 | UGACCAUGACAAUAACUGU |
| 1931 | 181 | UGAUUAUUGUGACAUCAAU | 182 | AUUGAUGUCACAAUAAUCA |
| 1932 | 183 | GAUUAUUGUGACAUCAAUA | 184 | UAUUGAUGUCACAAUAAUC |
| 2332 | 185 | AGGAAAUACAUUGCUGCAC | 186 | GUGCAGCAAUGUAUUUCCU |
| 2030 | 187 | UUGAAAGGGAUGAUGAAAA | 188 | UUUUCAUCAUCCCUUUCAA |
| 2210 | 189 | AUAAAAACCGUUAUGUUGA | 190 | UCAACAUAACGGUUUUUAU |
| 1930 | 191 | CUGAUUAUUGUGACAUCAA | 192 | UUGAUGUCACAAUAAUCAG |
| 2329 | 193 | CCCAGGAAAUACAUUGCUG | 194 | CAGCAAUGUAUUUCCUGGG |
| 2333 | 195 | GGAAAUACAUUGCUGCACA | 196 | UGUGCAGCAAUGUAUUUCC |
| 2409 | 197 | CACAGUUAUUGUCAUGGUC | 198 | GACCAUGACAAUAACUGUG |
| 2438 | 199 | AAGAAGGAAACAGGAACAA | 200 | UUGUUCCUGUUUCCUUCUU |
| 1933 | 201 | AUUAUUGUGACAUCAAUAG | 202 | CUAUUGAUGUCACAAUAAU |
| 2330 | 203 | CCAGGAAAUACAUUGCUGC | 204 | GCAGCAAUGUAUUUCCUGG |
| 2433 | 205 | AUGUGAAGAAGGAAACAGG | 206 | CCUGUUUCCUUCUUCACAU |
| 1934 | 207 | UUAUUGUGACAUCAAUAGC | 208 | GCUAUUGAUGUCACAAUAA |
| 2326 | 209 | GAACCCAGGAAAUACAUUG | 210 | CAAUGUAUUUCCUGGGUUC |
| 2327 | 211 | AACCCAGGAAAUACAUUGC | 212 | GCAAUGUAUUUCCUGGGUU |
| 2407 | 213 | GCCACAGUUAUUGUCAUGG | 214 | CCAUGACAAUAACUGUGGC |
| 2431 | 215 | CGAUGUGAAGAAGGAAACA | 216 | UGUUUCCUUCUUCACAUCG |
| 2432 | 217 | GAUGUGAAGAAGGAAACAG | 218 | CUGUUUCCUUCUUCACAUC |
| 2434 | 219 | UGUGAAGAAGGAAACAGGA | 220 | UCCUGUUUCCUUCUUCACA |
| 2435 | 221 | GUGAAGAAGGAAACAGGAA | 222 | UUCCUGUUUCCUUCUUCAC |
| 2219 | 223 | GUUAUGUUGACAUUCUUCC | 224 | GGAAGAAUGUCAACAUAAC |
| 2408 | 225 | CCACAGUUAUUGUCAUGGU | 226 | ACCAUGACAAUAACUGUGG |
| 2441 | 227 | AAGGAAACAGGAACAAGUG | 228 | CACUUGUUCCUGUUUCCUU |
| 2437 | 229 | GAAGAAGGAAACAGGAACA | 230 | UGUUCCUGUUUCCUUCUUC |
| 2135 | 231 | UGGCUGAAUUUCAGAGCAU | 232 | AUGCUCUGAAAUUCAGCCA |
| 2029 | 233 | GUUGAAAGGGAUGAUGAAA | 234 | UUUCAUCAUCCCUUUCAAC |
| 2134 | 235 | CUGGCUGAAUUUCAGAGCA | 236 | UGCUCUGAAAUUCAGCCAG |
| 1928 | 237 | UUCUGAUUAUUGUGACAUC | 238 | GAUGUCACAAUAAUCAGAA |
| 2439 | 239 | AGAAGGAAACAGGAACAAG | 240 | CUUGUUCCUGUUUCCUUCU |
| 1927 | 241 | UUUCUGAUUAUUGUGACAU | 242 | AUGUCACAAUAAUCAGAAA |

TABLE 4

Exemplary dsRNAs having NN-dinucleotide overhangs and targeting CD45.

| position of 5' base on transcript NM_002838.2 | SEQ ID NO: | Sense strand sequence (5' to 3') Double overhang Design | SEQ ID NO: | Antisense strand sequence (5' to 3') Double overhang design |
|---|---|---|---|---|
| 2208 | 243 | GAAUAAAAACCGUUAUGUUNN | 244 | AACAUAACGGUUUUUAUUCNN |
| 2215 | 245 | AACCGUUAUGUUGACAUUCNN | 246 | GAAUGUCAACAUAACGGUUNN |
| 1929 | 247 | UCUGAUUAUUGUGACAUCANN | 248 | UGAUGUCACAAUAAUCAGANN |
| 2212 | 249 | AAAAACCGUUAUGUUGACANN | 250 | UGUCAACAUAACGGUUUUNN |
| 2328 | 251 | ACCCAGGAAAUACAUUGCUNN | 252 | AGCAAUGUAUUUCCUGGGUNN |
| 2206 | 253 | CAGAAUAAAAACCGUUAUGNN | 254 | CAUAACGGUUUUUAUUCUGNN |
| 2207 | 255 | AGAAUAAAAACCGUUAUGUNN | 256 | ACAUAACGGUUUUUAUUCNN |
| 2411 | 257 | CAGUUAUUGUCAUGGUCACNN | 258 | GUGACCAUGACAAUAACUGNN |
| 2209 | 259 | AAUAAAAACCGUUAUGUUGNN | 260 | CAACAUAACGGUUUUUAUUNN |
| 2331 | 261 | CAGGAAAUACAUUGCUGCANN | 262 | UGCAGCAAUGUAUUUCCUGNN |
| 2214 | 263 | AAACCGUUAUGUUGACAUUNN | 264 | AAUGUCAACAUAACGGUUUNN |
| 2213 | 265 | AAAACCGUUAUGUUGACAUNN | 266 | AUGUCAACAUAACGGUUUNN |
| 2217 | 267 | CCGUUAUGUUGACAUUCUNN | 268 | AAGAAUGUCAACAUAACGGNN |
| 2216 | 269 | ACCGUUAUGUUGACAUUCNN | 270 | AGAAUGUCAACAUAACGGUNN |
| 2211 | 271 | UAAAACCGUUAUGUUGACNN | 272 | GUCAACAUAACGGUUUUUANN |
| 2218 | 273 | CGUUAUGUUGACAUUCUUCNN | 274 | GAAGAAUGUCAACAUAACGNN |
| 2410 | 275 | ACAGUUAUUGUCAUGGUCANN | 276 | UGACCAUGACAAUAACUGUNN |
| 1931 | 277 | UGAUUAUUGUGACAUCAAUNN | 278 | AUUGAUGUCACAAUAAUCANN |
| 1932 | 279 | GAUUAUUGUGACAUCAAUANN | 280 | UAUUGAUGUCACAAUAAUCNN |
| 2332 | 281 | AGGAAAUACAUUGCUGCACNN | 282 | GUGCAGCAAUGUAUUUCCUNN |
| 2030 | 283 | UUGAAAGGGAUGAUGAAAANN | 284 | UUUUCAUCAUCCCUUUCAANN |
| 2210 | 285 | AUAAAAACCGUUAUGUUGANN | 286 | UCAACAUAACGGUUUUUAUNN |
| 1930 | 287 | CUGAUUAUUGUGACAUCAANN | 288 | UUGAUGUCACAAUAAUCAGNN |
| 2329 | 289 | CCCAGGAAAUACAUUGCUGNN | 290 | CAGCAAUGUAUUUCCUGGGNN |
| 2333 | 291 | GGAAAUACAUUGCUGCACANN | 292 | UGUGCAGCAAUGUAUUUCCNN |
| 2409 | 293 | CACAGUUAUUGUCAUGGUCNN | 294 | GACCAUGACAAUAACUGUGNN |
| 2438 | 295 | AAGAAGGAAACAGGAACAANN | 296 | UUGUUCCUGUUUCCUUCUUNN |
| 1933 | 297 | AUUAUUGUGACAUCAAUAGNN | 298 | CUAUUGAUGUCACAAUAAUNN |
| 2330 | 299 | CCAGGAAAUACAUUGCUGCNN | 300 | GCAGCAAUGUAUUUCCUGGNN |
| 2433 | 301 | AUGUGAAGAAGGAAACAGGNN | 302 | CCUGUUUCCUUCUUCACAUNN |
| 1934 | 303 | UUAUUGUGACAUCAAUAGCNN | 304 | GCUAUUGAUGUCACAAUAANN |
| 2326 | 305 | GAACCCAGGAAAUACAUUGNN | 306 | CAAUGUAUUUCCUGGGUUCNN |
| 2327 | 307 | AACCCAGGAAAUACAUUGCNN | 308 | GCAAUGUAUUUCCUGGGUUNN |
| 2407 | 309 | GCCACAGUUAUUGUCAUGGNN | 310 | CCAUGACAAUAACUGUGGCNN |
| 2431 | 311 | CGAUGUGAAGAAGGAAACANN | 312 | UGUUUCCUUCUUCACAUCGNN |
| 2432 | 313 | GAUGUGAAGAAGGAAACAGNN | 314 | CUGUUUCCUUCUUCACAUCNN |

TABLE 4-continued

Exemplary dsRNAs having NN-dinucleotide overhangs and targeting CD45.

| position of 5' base on transcript NM_002838.2 | SEQ ID NO: | Sense strand sequence (5' to 3') Double overhang Design | SEQ ID NO: | Antisense strand sequence (5' to 3') Double overhang design |
|---|---|---|---|---|
| 2434 | 315 | UGUGAAGAAGGAAACAGGANN | 316 | UCCUGUUUCCUUCUUCACANN |
| 2435 | 317 | GUGAAGAAGGAAACAGGAANN | 318 | UUCCUGUUUCCUUCUUCACNN |
| 2219 | 319 | GUUAUGUUGACAUUCUUCCNN | 320 | GGAAGAAUGUCAACAUAACNN |
| 2408 | 321 | CCACAGUUAUUGUCAUGGUNN | 322 | ACCAUGACAAUAACUGUGGNN |
| 2441 | 323 | AAGGAAACAGGAACAAGUGNN | 324 | CACUUGUUCCUGUUUCCUUNN |
| 2437 | 325 | GAAGAAGGAAACAGGAACANN | 326 | UGUUCCUGUUUCCUUCUUCNN |
| 2135 | 327 | UGGCUGAAUUUCAGAGCAUNN | 328 | AUGCUCUGAAAUUCAGCCANN |
| 2029 | 329 | GUUGAAAGGGAUGAUGAAANN | 330 | UUUCAUCAUCCCUUUCAACNN |
| 2134 | 331 | CUGGCUGAAUUUCAGAGCANN | 332 | UGCUCUGAAAUUCAGCCAGNN |
| 1928 | 333 | UUCUGAUUAUUGUGACAUCNN | 334 | GAUGUCACAAUAAUCAGAANN |
| 2439 | 335 | AGAAGGAAACAGGAACAAGNN | 336 | CUUGUUCCUGUUUCCUUCUNN |
| 1927 | 337 | UUUCUGAUUAUUGUGACAUNN | 338 | AUGUCACAAUAAUCAGAAANN |

Unless otherwise defined, all technical and scientific terms used herein have the same meaning as commonly understood by one of ordinary skill in the art to which this invention belongs. Although methods and materials similar or equivalent to those described herein can be used in the practice or testing of the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

EXAMPLES

Example 1

In silico selection of siRNAs targeting CD45. siRNA design was carried out to identify siRNAs targeting CD45 (also known PTPRC, B220, CD45, GP180, LCA, LY5, and T200). Human mRNA sequences to CD45, RefSeq ID number: NM_002838.3, NM_080921.2, NM_080922.2, NM_080923.2, Y00062.1, Y00638.1, BC014239.2, BC017863.1, BC031525.1, BC121086.1, BC121087.1, BC127656.1, BC127657.1, AY429565.1, AY567999.1, AK130573.1, DA670254.1, DA948670.1, AY429566.1, and CR621867.1 were used. Mouse mRNA sequences to CD45, RefSeq ID number: NM_011210.2, AK054056.1, AK088215.1, AK154893.1, AK171802.1, BC028512.1, EF101553.1, L36091.1, M11934.1, M14342.1, M14343.1, M15174.1, M17320.1, and M92933.1 were used. Rhesus monkey mRNA sequence to CD45, RefSeqID number; XR_012672.1 was also used.

siRNA duplexes cross-reactive to human, mouse and rhesus CD45 transcripts were designed. Forty-eight duplexes were synthesized and screened as outlined in Tables 1-3.

The sequences for human, mouse and partial rhesus CD45 mRNAs were downloaded from NCBI Nucleotide database and the human sequence (Human CD45: NM_002838.3, 5330 bp) was further used as reference sequence.

For identification of further rhesus CD45 sequences, a blast search with the human reference sequence was conducted at NCBI against the rhesus reference genome. The downloaded rhesus sequence and the hit regions in the blast hit were assembled to a rhesus consensus sequence with 91% identity to human CD45 reference sequence over the full-length.

All conserved 19 mers were extracted from the human mRNA reference sequence, resulting in the pool of candidate target sites corresponding to 5312 (sense strand) sequences. Human-mouse-rhesus cross-reactivity was defined as a prerequisite for in silico selection of siRNAs out of this candidate pool. As no conserved regions are present in all human and/or mouse variants, the criterion for selection was relaxed to cross-reactivity to most relevant human and mouse CD45 sequences, which we assumed to be RefSeq sequences as well as other mRNAs for which protein expression has been described.

To determine cross-reactivity to human and mouse CD45 variants and rhesus-reactive siRNAs, the presence of each candidate siRNA target site was searched in the sequences.

Further, the predicted specificity of the siRNA was used as criterion for selection out of the pool of human-mouse-rhesus cross-reactive siRNAs, manifested by targeting human CD45 mRNA sequences, but not other human mRNAs.

The specificity of an siRNA can be expressed via its potential to target other genes, which are referred to as "off-target genes." For predicting the off-target potential of an siRNA, the following assumptions were made: (1) off-target potential of a strand can be deduced from the number and distribution of mismatches to an off-target; (2) the most relevant off-target, that is the gene predicted to have the highest probability to be silenced due to tolerance of mismatches, determines the off-target potential of the strand; (3) positions 2 to 9

(counting 5' to 3') of a strand (seed region) may contribute more to off-target potential than the rest of the sequence (that is non-seed and cleavage site region); (4) positions 10 and 11 (counting 5' to 3') of a strand (cleavage site region) may contribute more to off-target potential than non-seed region (that is positions 12 to 18, counting 5' to 3'); (5) positions 1 and 19 of each strand are not relevant for off-target interactions; (6) off-target potential can be expressed by the off-target score of the most relevant off-target, calculated based on number and position of mismatches of the strand to the most homologous region in the off-target gene considering assumptions 3 to 5; and (7) off-target potential of antisense and sense strand will be relevant, whereas potential abortion of sense strand activity by internal modifications introduced is likely.

SiRNAs with low off-target potential were defined as preferable and assumed to be more specific.

In order to identify human CD45-specific siRNAs, all other human transcripts that were considered potential off-targets, were searched for potential target regions for human-mouse-rhesus cross-reactive 19 mer sense strand sequences as well as complementary antisense strands. For this, the fastA algorithm was used to determine the most homologous hit region in each sequence of the human RefSeq database, which we assume to represent the comprehensive human transcriptome.

FastA output files were analyzed further by a Perl script to rank all potential off-targets according to assumptions 3' to 5', and thus to identify the most relevant off-target gene and its off-target score.

The script extracted the following off-target properties for each 19 mer input sequence and each off-target gene to calculate the off-target score:

Number of mismatches in non-seed region, number of mismatches in seed region, and number of mismatches in cleavage site region.

The off-target score was calculated by considering assumptions 3 to 5 as follows:

Off-target score=number of seed mismatches*10+ number of cleavage site mismatches*1.2+number of non-seed mismatches*1

The most relevant off-target gene for each 19 mer sequence was defined as the gene with the lowest off-target score. Accordingly, the lowest off-target score was defined as representative for the off-target potential of a strand.

For the siRNA set in Table 2, cross-reactivity to rhesus, all human and mouse RefSeq sequences as well as to most variants with described protein was defined as prerequisite for selection. Further criterion was an off-target score of 1 or more for the antisense strand, whereas all sequences containing 4 or more consecutive G' s (poly-G sequences) were excluded. 48 human-mouse-rhesus cross-reactive sequences that do not possess most-relevant off-targets predicted to be expressed in immune cells were selected (Tables 1 and 2).

Table 1 shows CD45 target sequences, Table 2 shows CD45 siRNAs, and Table 3 shows the IC values for the siRNAs tested in a dose response assay. Table 4 shows exemplary CD45 siRNAs that are not modified, and Table 5 shows exemplary CD45 siRNAs having dinucleotide overhangs.

Nucleic acid sequences are represented below using standard nomenclature, and specifically the abbreviations of Table 6.

TABLE 6

Abbreviations of nucleotide monomers used in nucleic acid sequence representation. It will be understood that these monomers, when present in an oligonucleotide, are mutually linked by 5'-3'-phosphodiester bonds.

| Abbreviation[a] | Nucleotide(s) |
|---|---|
| A | Adenosine |
| C | cytidine |
| G | guanosine |
| T | thymidine |
| U | uridine |
| N | any nucleotide (G, A, C, U, T) |
| a | 2'-O-methyladenosine |
| c | 2'-O-methylcytidine |
| g | 2'-O-methylguanosine |
| u | 2'-O-methyluridine |
| dT | 2'-deoxythymidine |
| s | a phosphorothioate linkage |

Example 2

Screening assay. 48 human-mouse-rhesus cross-reactive siRNAs were first screened at 50 nM single dose (three independent screens, each done in quadruplicate) by bDNA assay in P388D1 cells. For the most potent siRNAs, dose response was performed by bDNA analysis in P388D1 to identify the IC20, IC50 and IC80 dose that lowers the level of CD45 transcript by 20, 50 and 80%, respectively. siRNAs with the best IC values in the bDNA assay were screened by flow cytometry to identify the IC20, IC50 and IC80 dose required to lower the amount of CD45 protein by 20, 50 and 80%, respectively.

Cell Line. A P388D1 mouse macrophage cell line was obtained from the American Type Culture Collection (ATCC, Rockville Md., USA; ATCC # TIB-63) and grown in DMEM containing 10% heat-inactivated fetal bovine serum (FBS), 4 mM L-glutamine, 1.5 g/L sodium bicarbonate at 37° C. under a 5% CO2/95% air atmosphere at 37° C.

Cell Culture, siRNA transfection. P388D1 cells were plated in 24-well plates at $8 \times 10^4$ cells per well in 0.4 ml growth medium a day before transfection. P388D1 cells were 80% confluent the day of siRNA transfection. Before transfection, cells are fed with 0.25 ml growth medium.

Figure 1B:
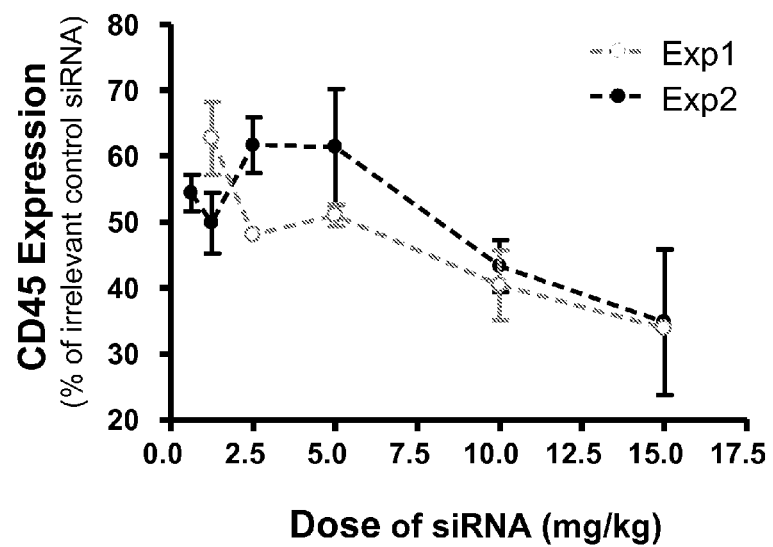

Prior to adding to cells, 1.5 ml (50 µl per well) Optimem I (Invitrogen) and 90 µl (3 µl per well) Lipofectamin 2000 (Invitrogen), the amount sufficient for transfection of one 24 well plate, were combined in a 2 ml Sarstedt tube and incubated for 10-15 minutes at room temperature. The appropriate amount of siRNA dissolved in transfection buffer is then added to the Optimem/lipofectamine 2000 mixture to give the desired final concentration, mixed, and incubated an additional 15-25 minutes at room temperature. 50 µl of the siRNA/reagent complex was then added dropwise to each well as dictated by the experimental design. Plates were then gently rocked to ensure complete mixing and incubated at 37° C. at 5% CO2/95% air for 48 hours. The cells were lysed and CD45 mRNA transcript was quantitated in relation to a house-keeping gene transcript by branched DNA (bDNA) assay. CD45 protein expression level was determined by flow cytometry, for this assay cells were harvested by pipetting without lysing.

siRNA to CD45 silenced CD45 in mouse macrophages in vivo. C57B1/6J mice (Jackson Labs) were injected intraperitoneally with 1 mL of 4% Brewers thioglycollate medium (Difco) 3 days prior to injecting 10 mg/kg of 98N12-5 formulated siCD45 or siGFP i.p. (4 mice per group). The thioglycollate acted as a sterile inflammation stimulus. Peritoneal lavage was collected 4 days later and stained with fluorophore conjugated antibodies to CD11b, Gr1 and CD45 (BD Biosciences). Flow cytometry samples were run on the LSR11 flow cytometer (BD Biosciences) and FlowJo software (Treestar) was used to identify the CD11b$^{high}$ Gr1$^{low}$ macrophage population and quantify CD45 expression. A 65% reduction of CD45 protein expression was observed in the peritoneal macrophage population when treated with the formulated CD45 siRNA (FIG. 1). Two independent dose response experiments were conducted examining the effect of 0.6-15.0 mg/kg administration of 98N12-5 formulated siCD45 or siGFP i.p. (2-3 mice per group). These experiments were conducted identically to those described above and demonstrated effective specific in vivo silencing of CD45 protein expression at all concentrations tested when treated with the formulated CD45 siRNA (FIG. 1, top panel). The 98N12-5 formulation is a lipidoid synthesized by addition of acrylamides or acrylates to amines.

The sequences for the sense and antisense strands of the CD45 siRNA are as follows.

```
5'-cuGGcuGAAuuucAGAGcATsT-3' sense
(SEQ ID NO: 89 single strand # A22825)

5'-UGCUCUGAAAUUcAGCcAGTsT-3' antisense
(SEQ ID NO: 90 single strand #_A22826)
```

The siGFP sequences are as follows:

```
                                       (SEQ ID NO: 145)
5'-CcAcAuGAAGcAGcACGACusU-3' sense
(single strand # AL4545)

(SEQ ID NO: 146)
5'-AAGUCGUGCUGCUUCAUGUGgsusC-3' antisense
(single strand # AL4381)
```

2'-O-Me modified nucleotides are in lower case, and phosphorothioate linkages are represented by an "s". siRNAs were generated by annealing equimolar amounts of complementary sense and antisense strands.

All procedures used in animal studies were approved by the Institutional Animal Care and Use Committee (IACUC) and were consistent with local, state, and federal regulations as applicable.

Lipidoid-based siRNA formulations included lipidoid, cholesterol, poly(ethylene glycol)-lipid (PEG-lipid), and siRNA. Formulations were prepared using a protocol similar to that described by Semple and colleagues (Maurer et al. Biophys. J. 80:2310-2326, 2001; Semple et al., Biochim. Biophys. Acta 1510:152-166, 2001). Stock solutions of 98N12-5(1).4HCl MW 1489, mPEG2000-Ceramide C16 (Avanti Polar Lipids) MW 2634 or mPEG2000-DMG MW 2660, and cholesterol MW 387 (Sigma-Aldrich) were prepared in ethanol and mixed to yield a molar ratio of 42:10:48. Mixed lipids were added to 125 mM sodium acetate buffer pH 5.2 to yield a solution containing 35% ethanol, resulting in spontaneous formation of empty lipidoid nanoparticles. Resulting nanoparticles were extruded through a 0.08μ membrane (2 passes). siRNA in 35% ethanol and 50 mM sodium acetate pH 5.2 was added to the nanoparticles at 1:7.5 (wt:wt) siRNA:total lipids and incubated at 37° C. for 30 min. Ethanol removal and buffer exchange of siRNA-containing lipidoid nanoparticles was achieved by tangential flow filtration against phosphate buffered saline using a 100,000 MWCO membrane. Finally, the formulation was filtered through a 0.2μ sterile filter. Particle size was determined using a Malvern Zetasizer NanoZS (Malvern, UK). siRNA content was determined by UV absorption at 260 nm and siRNA entrapment efficiency was determined by Ribogreen assay 32. Resulting particles had a mean particle diameter of approximately 50 nm, with peak width of 20 nm, and siRNA entrapment efficiency of >95%. See also PCT/US2007/080331.

Example 3

Figure 2:
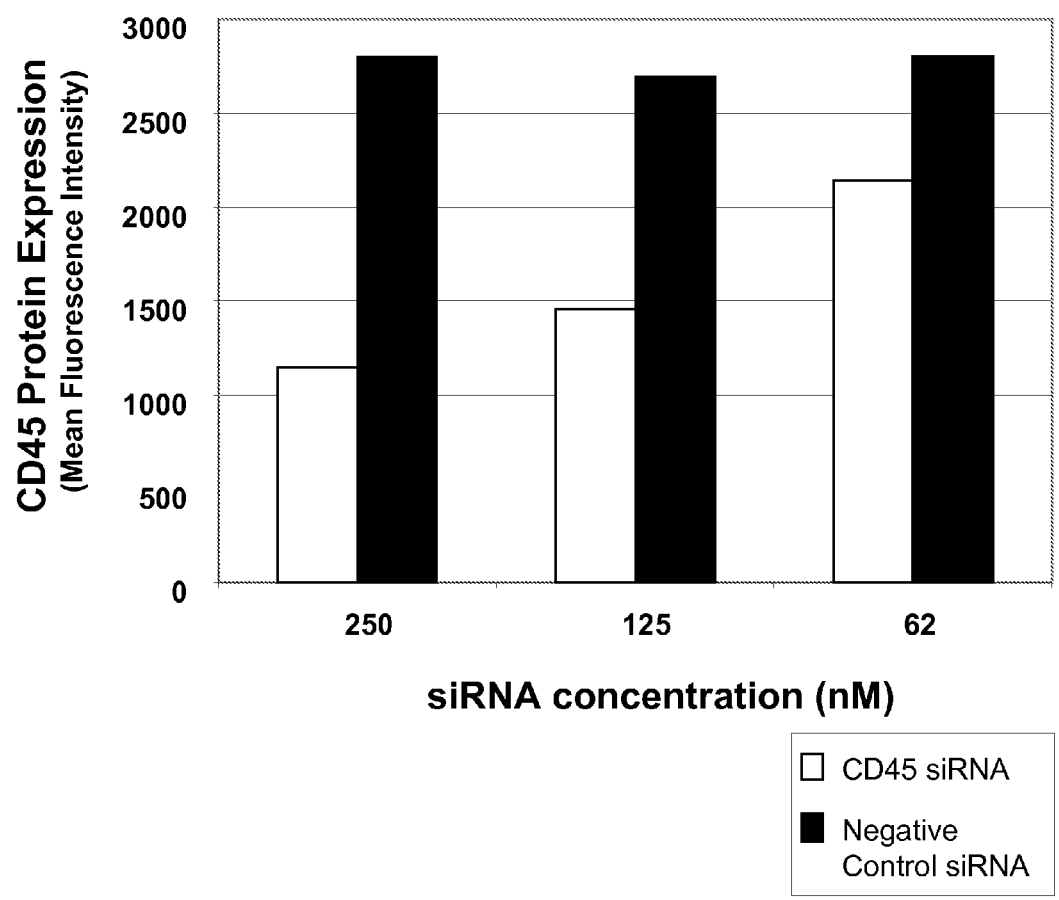
FIG. 2 is a bar graph showing in vitro RNAi-mediated silencing of CD45 in primary mouse bone-marrow derived monocytes using a lipodoid formulation.

Bone marrow-derived macrophage transfection. Murine bone marrow derived macrophages were cultured according to standard protocol (Cunnick et al., *J. Immunol. Methods* 311:96-105, 2006). Cells were cultured in 12-well dishes for five days in the presence of 8 ng/mL of M-CSF. The optimal siRNA to lipidoid ratio was determined for each lipidoid (a ratio of either 5 or 10 wt:wt was used). Mixtures of irrelevant control siRNA or siCD45 (SEQ ID NOs:89 and 90, above) with lipidoids were prepared as described above. siRNA-lipidoid mixtures were added to macrophage cultures at the desired concentrations for 6 hours. Media was exchanged and GFP expression was analyzed by flow cytometry five days later. The formulated CD45 siRNA were shown to effectively silence primary murine bone marrow-derived macrophages with 65% protein reduction (FIG. 2)

Example 4

Figure 3:
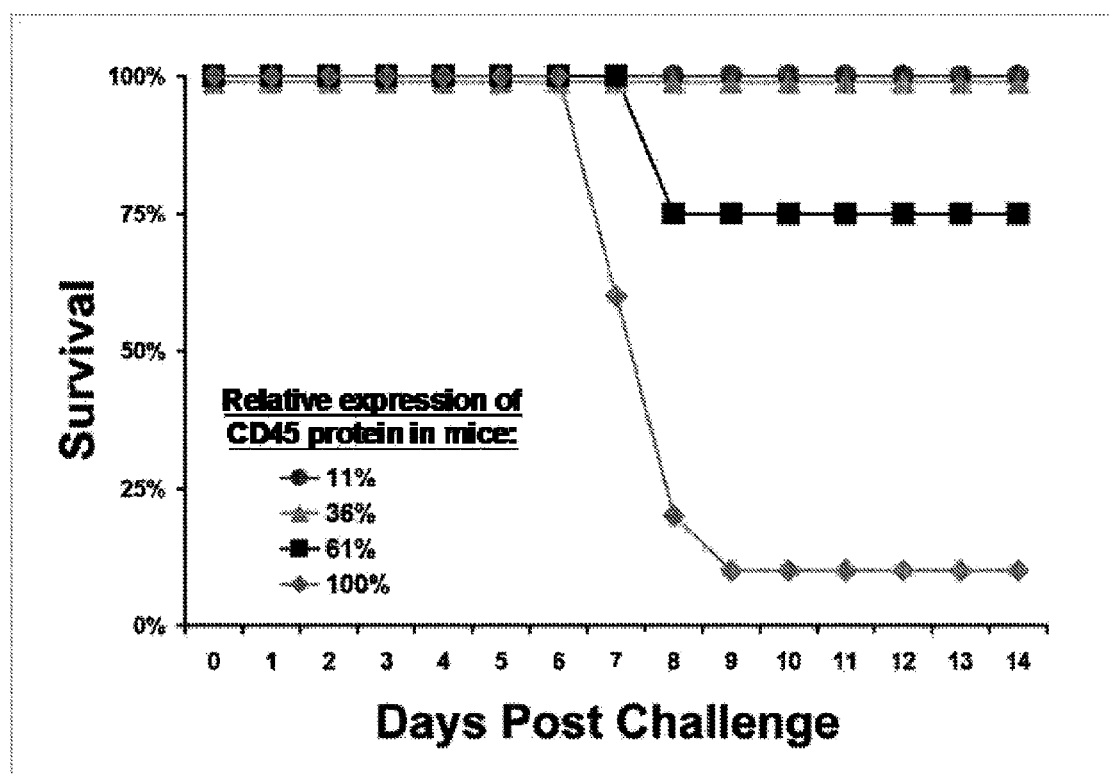
FIG. 3 is a graph showing that genetically modified mice expressing different levels of CD45 are protected from 30,000×LD50 Ebola-Zaire virus challenge.

CD45 as a cellular protein target that regulates infection from a broad range of pathogens. CD45 mitigates viral and bacterial infections. Genetically-modified mice with reduced expression level of CD45 were protected from *B. anthracia*, influenza, and Ebola (see FIG. 3). Given the ability of formulated CD45 siRNA to inhibit CD45 expression in vitro and in vivo by up to 65%, it is notable that significant protective effects against lethal Ebola challenge were seen in genetically-modified mice when CD45 expression was reduced by 11-65% (FIG. 3).

Example 5

Figure 4:
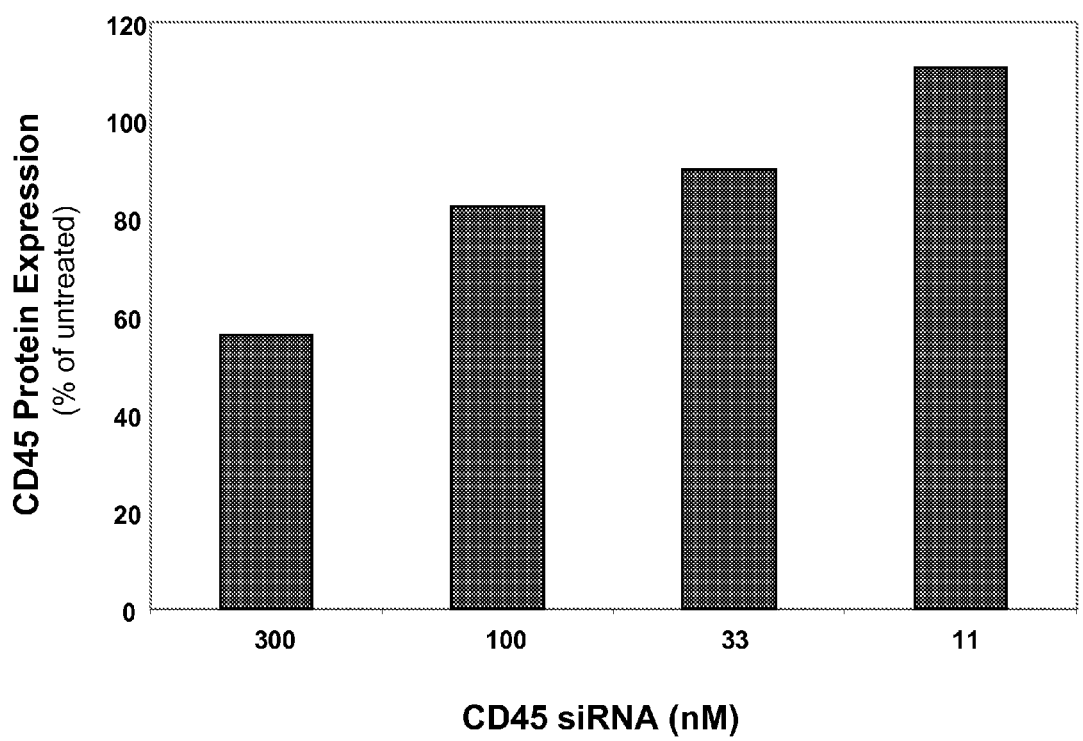
FIG. 4 is a bar graph showing in vitro RNAi-mediated silencing of CD45 in KG1, a human leukemia cell line using a lipodoid formulation.

CD45 siRNA silenced CD45 expression in human cells in vitro. The human acute myelogenous leukemia cell line, KG-1, was cultured according to standard protocol. Cells were plated into 96 wells and then untreated or treated with CD45 siRNA-lipidoid mixtures (as outlined for FIGS. 1 and 2) at the desired concentrations for 6 hours. Media was exchanged and CD45 expression was analyzed by flow cytometry four days later. The liposomally formulated CD45 siRNA were shown to effectively silence in human cells in vitro (FIG. 4). These results are consistent with the fact that the CD45 siRNA has 100% sequence identity to human and rodent CD45 and was shown to be active in reducing murine CD45 in vitro and in vivo (Table 3; FIGS. 1 and 2).

Example 6 dsRNA Synthesis

Source of Reagents

Where the source of a reagent is not specifically given herein, such reagent may be obtained from any supplier of reagents for molecular biology at a quality/purity standard for application in molecular biology.

siRNA Synthesis

Single-stranded RNAs were produced by solid phase synthesis on a scale of 1 µmole using an Expedite 8909 synthesizer (Applied Biosystems, Applera Deutschland GmbH, Darmstadt, Germany) and controlled pore glass (CPG, 500 Å, Proligo Biochemie GmbH, Hamburg, Germany) as solid support. RNA and RNA containing 2'-O-methyl nucleotides were generated by solid phase synthesis employing the corresponding phosphoramidites and 2'-O-methyl phosphoramidites, respectively (Proligo Biochemie GmbH, Hamburg, Germany). These building blocks were incorporated at selected sites within the sequence of the oligoribonucleotide chain using standard nucleoside phosphoramidite chemistry such as described in Current protocols in nucleic acid chemistry, Beaucage, S. L. et al. (Edrs.), John Wiley & Sons, Inc., New York, N.Y., USA. Phosphorothioate linkages were introduced by replacement of the iodine oxidizer solution with a solution of the Beaucage reagent (Chruachem Ltd, Glasgow, UK) in acetonitrile (1%). Further ancillary reagents were obtained from Mallinckrodt Baker (Griesheim, Germany).

Deprotection and purification of the crude oligoribonucleotides by anion exchange HPLC were carried out according to established procedures. Yields and concentrations were determined by UV absorption of a solution of the respective RNA at a wavelength of 260 nm using a spectral photometer (DU 640B, Beckman Coulter GmbH, Unterschleitβheim, Germany). Double stranded RNA was generated by mixing an equimolar solution of complementary strands in annealing buffer (20 mM sodium phosphate, pH 6.8; 100 mM sodium chloride), heated in a water bath at 85-90° C. for 3 minutes and cooled to room temperature over a period of 3-4 hours. The annealed RNA solution was stored at −20° C. until use.

For the synthesis of 3'-cholesterol-conjugated siRNAs (herein referred to as -Chol-3'), an appropriately modified solid support is used for RNA synthesis. The modified solid support is prepared as follows:

Diethyl-2-azabutane-1,4-dicarboxylate AA

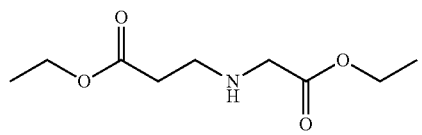

A 4.7 M aqueous solution of sodium hydroxide (50 mL) is added into a stirred, ice-cooled solution of ethyl glycinate hydrochloride (32.19 g, 0.23 mole) in water (50 mL). Then, ethyl acrylate (23.1 g, 0.23 mole) is added and the mixture is stirred at room temperature until completion of the reaction is ascertained by TLC. After 19 h the solution is partitioned with dichloromethane (3×100 mL). The organic layer is dried with anhydrous sodium sulfate, filtered and evaporated. The residue is distilled to afford AA (28.8 g, 61%).

3-{Ethoxycarbonylmethyl-[6-(9H-fluoren-9-yl-methoxycarbonyl-amino)-hexanoyl]-amino}-propionic acid ethyl ester AB

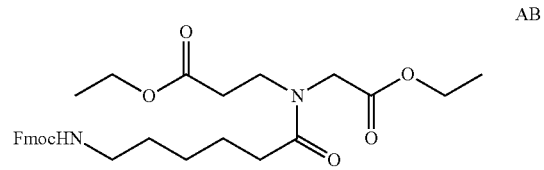

Fmoc-6-amino-hexanoic acid (9.12 g, 25.83 mmol) is dissolved in dichloromethane (50 mL) and cooled with ice. Diisopropylcarbodiimde (3.25 g, 3.99 mL, 25.83 mmol) is added to the solution at 0° C. It is then followed by the addition of Diethyl-azabutane-1,4-dicarboxylate (5 g, 24.6 mmol) and dimethylamino pyridine (0.305 g, 2.5 mmol). The solution is brought to room temperature and stirred further for 6 h. Completion of the reaction is ascertained by TLC. The reaction mixture is concentrated under vacuum and ethyl acetate is added to precipitate diisopropyl urea. The suspension is filtered. The filtrate is washed with 5% aqueous hydrochloric acid, 5% sodium bicarbonate and water. The combined organic layer is dried over sodium sulfate and concentrated to give the crude product which is purified by column chromatography (50% EtOAC/Hexanes) to yield 11.87 g (88%) of AB.

3-[(6-Amino-hexanoyl)-ethoxycarbonylmethyl-amino]-propionic acid ethyl ester AC

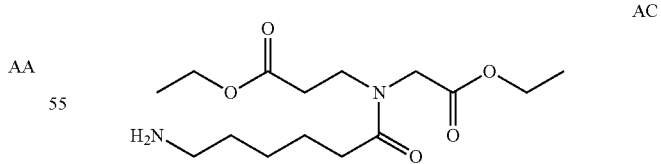

3-{Ethoxycarbonylmethyl-[6-(9H-fluoren-9-ylmethoxy-carbonylamino)-hexanoyl]-amino}-propionic acid ethyl ester AB (11.5 g, 21.3 mmol) is dissolved in 20% piperidine in dimethylformamide at 0° C. The solution is continued stirring for 1 h. The reaction mixture is concentrated under vacuum, water is added to the residue, and the product is extracted with ethyl acetate. The crude product is purified by conversion into its hydrochloride salt.

3-({6-[17-(1,5-Dimethyl-hexyl)-10,13-dimethyl-2,3,
4,7,8,9,10,11,12,13,14,15,16,17-tetradecahydro-1H-
cyclopenta[a]phenanthren-3-yloxycarbonylamino]-
hexanoyl}ethoxycarbonylmethyl-amino)-propionic
acid ethyl ester AD

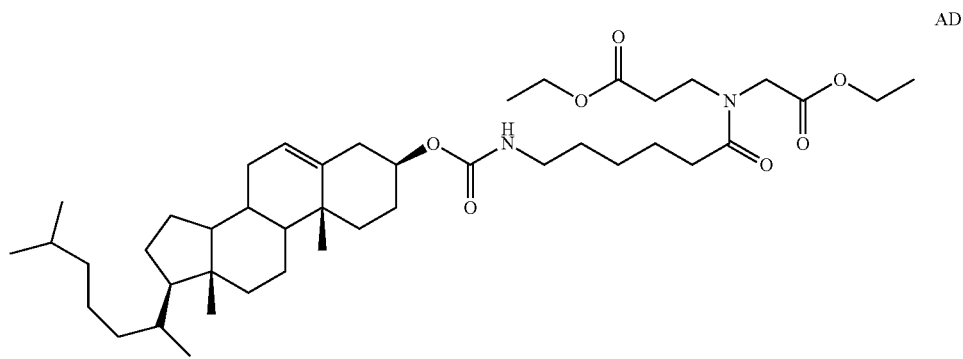

The hydrochloride salt of 3-[(6-Amino-hexanoyl)-ethoxy-carbonylmethyl-amino]-propionic acid ethyl ester AC (4.7 g, 14.8 mmol) is taken up in dichloromethane. The suspension is cooled to 0° C. on ice. To the suspension diisopropylethylamine (3.87 g, 5.2 mL, 30 mmol) is added. To the resulting solution cholesteryl chloroformate (6.675 g, 14.8 mmol) is added. The reaction mixture is stirred overnight. The reaction mixture is diluted with dichloromethane and ished with 10% hydrochloric acid. The product is purified by flash chromatography (10.3 g, 92%).

1-{6-[17-(1,5-Dimethyl-hexyl)-10,13-dimethyl-2,3,
4,7,8,9,10,11,12,13,14,15,16,17-tetradecahydro-1H-
cyclopenta[a]phenanthren-3-yloxycarbonylamino]
hexanoyl}-4-oxo-pyrrolidine-3-carboxylic acid ethyl
ester AE

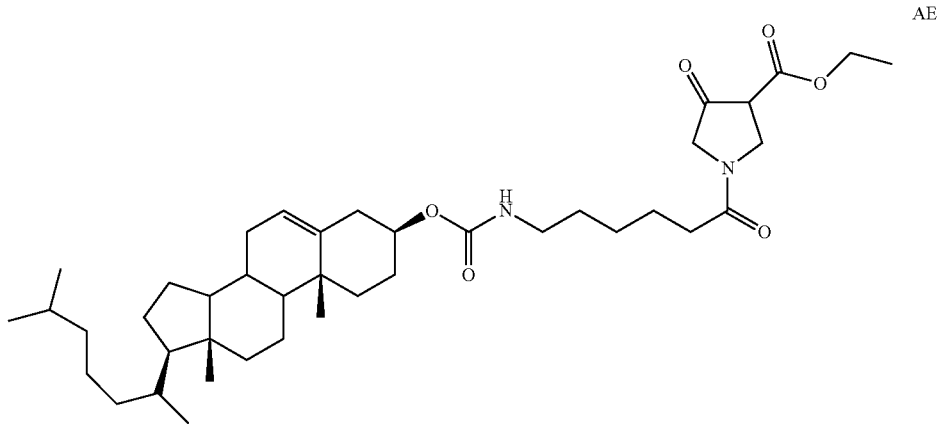

Potassium t-butoxide (1.1 g, 9.8 mmol) is slurried in 30 mL of dry toluene. The mixture is cooled to 0° C. on ice and 5 g (6.6 mmol) of diester AD is added slowly with stirring within 20 mins. The temperature is kept below 5° C. during the addition. The stirring is continued for 30 mins at 0° C. and 1 mL of glacial acetic acid is added, immediately followed by 4 g of $NaH_2PO_4.H_2O$ in 40 mL of water The resultant mixture is extracted twice with 100 mL of dichloromethane each and the combined organic extracts are washed twice with 10 mL of phosphate buffer each, dried, and evaporated to dryness. The residue is dissolved in 60 mL of toluene, cooled to 0° C. and extracted with three 50 mL portions of cold pH 9.5 carbonate buffer. The aqueous extracts are adjusted to pH 3 with phosphoric acid, and extracted with five 40 mL portions of chloroform which are combined, dried and evaporated to dryness. The residue is purified by column chromatography using 25% ethylacetate/hexane to afford 1.9 g of b-ketoester (39%).

[6-(3-Hydroxy-4-hydroxymethyl-pyrrolidin-1-yl)-6-oxo-hexyl]-carbamic acid 17-(1,5-dimethyl-hexyl)-10,13-dimethyl-2,3,4,7,8,9,10,11,12,13,14,15,16,17-tetradecahydro-1H-cyclopenta[a]phenanthren-3-yl ester AF

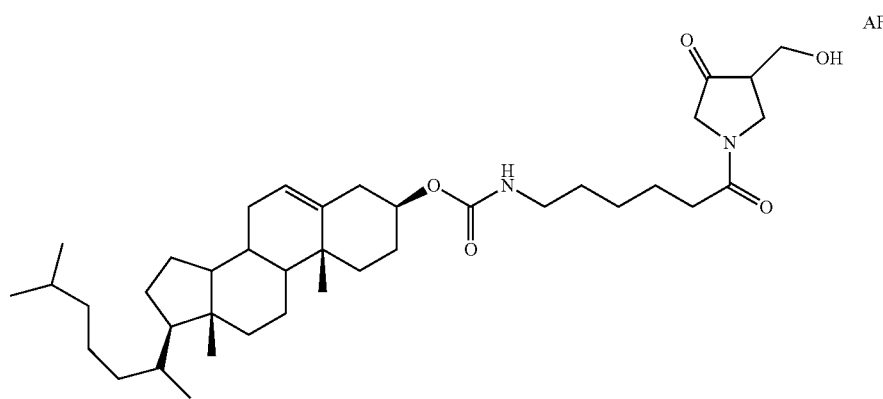

Methanol (2 mL) is added dropwise over a period of 1 h to a refluxing mixture of b-ketoester AE (1.5 g, 2.2 mmol) and sodium borohydride (0.226 g, 6 mmol) in tetrahydrofuran (10 mL). Stirring is continued at reflux temperature for 1 h. After cooling to room temperature, 1 N HCl (12.5 mL) is added, the mixture is extracted with ethylacetate (3×40 mL). The combined ethylacetate layer is dried over anhydrous sodium sulfate and concentrated under vacuum to yield the product which is purified by column chromatography (10% MeOH/$CHCl_3$) (89%).

(6-{3-[Bis-(4-methoxy-phenyl)-phenyl-methoxymethyl]-4-hydroxy-pyrrolidin-1-yl}-6-oxo-hexyl)-carbamic acid 17-(1,5-dimethyl-hexyl)-10,13-dimethyl-2,3,4,7,8,9,10,11,12,13,14,15,16,17-tetradecahydro-1H-cyclopenta[a]phenanthren-3-yl ester AG

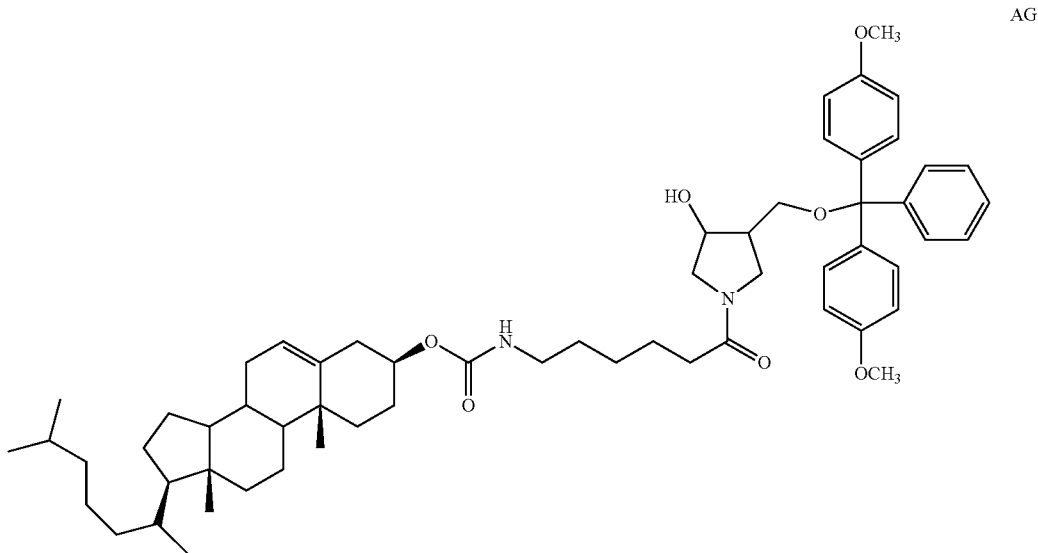

Diol AF (1.25 gm 1.994 mmol) is dried by evaporating with pyridine (2×5 mL) in vacuo. Anhydrous pyridine (10 mL) and 4,4'-dimethoxytritylchloride (0.724 g, 2.13 mmol) are added with stirring. The reaction is carried out at room temperature overnight. The reaction is quenched by the addition of methanol. The reaction mixture is concentrated under vacuum and to the residue dichloromethane (50 mL) is added. The organic layer is washed with 1M aqueous sodium bicarbonate. The organic layer is dried over anhydrous sodium sulfate, filtered and concentrated. The residual pyridine is removed by evaporating with toluene. The crude product is purified by column chromatography (2% MeOH/Chloroform, Rf=0.5 in 5% MeOH/CHCl₃) (1.75 g, 95%).

Succinic acid mono-(4-[bis-(4-methoxy-phenyl)-phenyl-methoxymethyl]-1-{6-[17-(1,5-dimethyl-hexyl)-10,13-dimethyl 2,3,4,7,8,9,10,11,12,13,14,15,16,17-tetradecahydro-1H cyclopenta[a]phenanthren-3-yloxycarbonylamino]-hexanoyl}-pyrrolidin-3-yl) ester AH

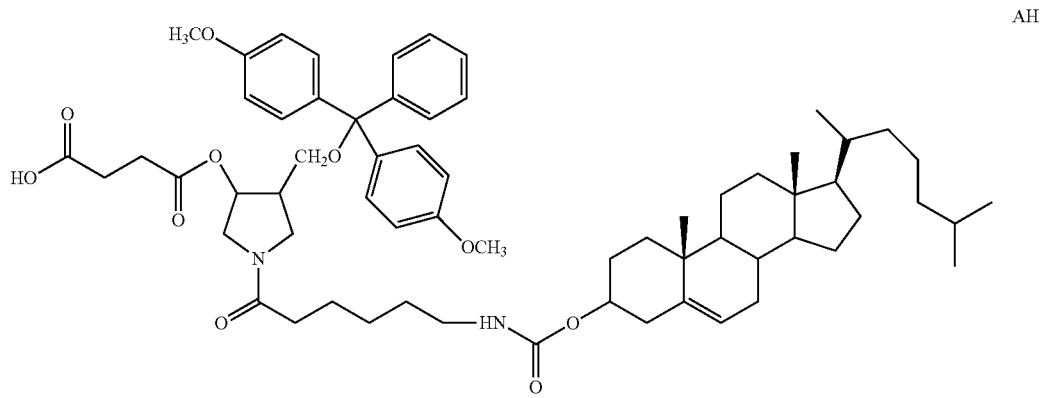

Compound AG (1.0 g, 1.05 mmol) is mixed with succinic anhydride (0.150 g, 1.5 mmol) and DMAP (0.073 g, 0.6 mmol) and dried in a vacuum at 40° C. overnight. The mixture is dissolved in anhydrous dichloroethane (3 mL), triethylamine (0.318 g, 0.440 mL, 3.15 mmol) is added and the solution is stirred at room temperature under argon atmosphere for 16 h. It is then diluted with dichloromethane (40 mL) and washed with ice cold aqueous citric acid (5 wt %, 30 mL) and water (2×20 mL). The organic phase is dried over anhydrous sodium sulfate and concentrated to dryness. The residue is used as such for the next step.

Cholesterol Derivatised CPG AI

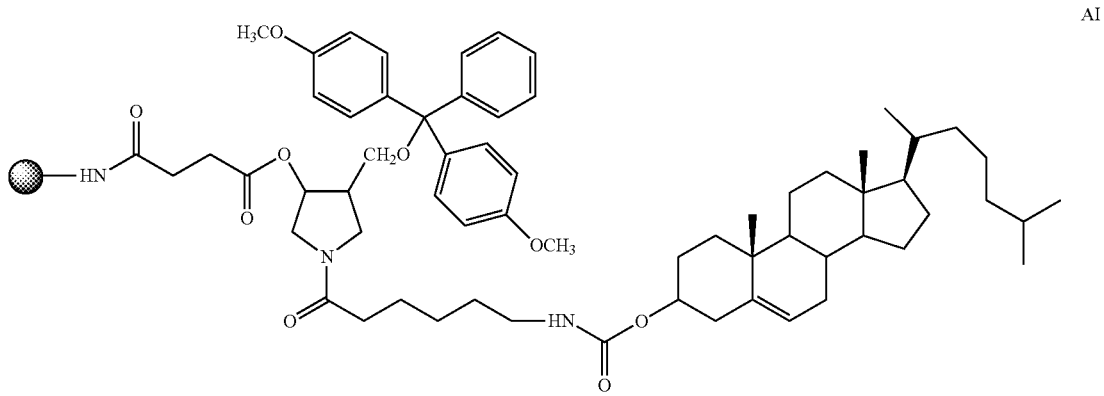

Succinate AH (0.254 g, 0.242 mmol) is dissolved in a mixture of dichloromethane/acetonitrile (3:2, 3 mL). To that solution DMAP (0.0296 g, 0.242 mmol) in acetonitrile (1.25 mL), 2,2'-Dithio-bis(5-nitropyridine) (0.075 g, 0.242 mmol) in acetonitrile/dichloroethane (3:1, 1.25 mL) are added successively. To the resulting solution triphenylphosphine (0.064 g, 0.242 mmol) in acetonitrile (0.6 ml) is added. The reaction mixture turned bright orange in color. The solution is agitated briefly using a wrist-action shaker (5 mins). Long chain alkyl amine-CPG (LCAA-CPG) (1.5 g, 61 mM) is added. The suspension is agitated for 2 h. The CPG is filtered through a sintered funnel and washed with acetonitrile, dichloromethane and ether successively. Unreacted amino groups are masked using acetic anhydride/pyridine. The achieved loading of the CPG is measured by taking UV measurement (37 mM/g).

The synthesis of siRNAs bearing a 5'-12-dodecanoic acid bisdecylamide group (herein referred to as "5'-C32-") or a 5'-cholesteryl derivative group (herein referred to as "5'-Chol-") is performed as described in WO 2004/065601, except that, for the cholesteryl derivative, the oxidation step is performed using the Beaucage reagent in order to introduce a phosphorothioate linkage at the 5'-end of the nucleic acid oligomer.

Other embodiments are in the claims.

---

We claim:

1. A double-stranded ribonucleic acid (dsRNA), wherein said dsRNA comprises a sense strand and an antisense strand that form a duplex structure, wherein the antisense strand consists of the sequence of SEQ ID NO:90 and the sense strand consists of the sequence of SEQ ID NO:89,
    wherein each strand is modified as follows to include a 2'-O-methyl ribonucleotide as indicated by a lower case letter "c" or "u" and a phosphorothioate as indicated by a lower case letter "s";
    SEQ ID NO:89 is cuGGcuGAAuuucAGAGcATsT and
    SEQ ID NO:90 is UGCUCUGAAAUUcAGCcAGTsT, and wherein said dsRNA targets cleavage of a CD45 mRNA.

2. The dsRNA of claim 1, wherein said dsRNA, upon contact with a cell expressing said CD45 gene, inhibits expression of said CD45 gene by at least 40% as compared to expression of a CD45 gene in a cell treated with a control dsRNA.

3. The dsRNA of claim 1, wherein said dsRNA, upon contact with a cell expressing CD45, inhibits expression of CD45 by at least 40% as compared to expression of a CD45 gene in a cell treated with a control dsRNA as measured in the P388D1 cell assay.

4. A cell comprising the dsRNA of claim 1.

5. A pharmaceutical composition comprising a dsRNA of claim 1, and a pharmaceutically acceptable carrier.

6. The pharmaceutical composition of claim 5, wherein said dsRNA, upon contact with a cell expressing said CD45 gene, inhibits expression of said CD45 gene by at least 40%, as compared to expression of a CD45 gene in a cell treated with a control dsRNA, as measured in a P388D1 cell assay.

7. A method for inhibiting expression of a CD45 gene in a cell, the method comprising:
    (a) introducing into the cell a double-stranded ribonucleic acid (dsRNA) of claim 1; and
    (b) maintaining the cell produced in step (a) for a time sufficient to obtain degradation of the mRNA transcript of the CD45 gene, thereby inhibiting expression of the CD45 gene in the cell.

8. The method of claim 7, wherein the cell produced in step (a) is maintained for a time sufficient inhibit expression of CD45 by 40% as compared to expression of a CD45 gene in a cell treated with a control dsRNA.

9. A method of treating or managing an autoimmune disease comprising administering to a patient in need of such treatment, or management of a therapeutically effective amount of a dsRNA of claim 1.

10. The method of claim 9, wherein the autoimmune disease is Graves' disease or multiple sclerosis.

11. A method of treating or managing a viral infection comprising administering to a patient in need of such treatment or management of a therapeutically effective amount of a dsRNA of claim 1.

12. The method of claim 11, wherein the infection is caused by a virus of the group consisting of Ebola, influenza, anthrax, hepatitis B and hepatitis C.

13. A vector for inhibiting the expression of the CD45 gene in a cell, said vector comprising a regulatory sequence operably linked to the dsRNA of claim 1.

14. A cell comprising the vector of claim 13.

* * * * *

UNITED STATES PATENT AND TRADEMARK OFFICE
CERTIFICATE OF CORRECTION

| | | |
|---|---|---|
| PATENT NO. | : 8,288,525 B2 | Page 1 of 1 |
| APPLICATION NO. | : 12/867230 | |
| DATED | : October 16, 2012 | |
| INVENTOR(S) | : Antonin de Fougerolles et al. | |

It is certified that error appears in the above-identified patent and that said Letters Patent is hereby corrected as shown below:

Title Page, Item (73) Assignee: Please add the following

--United States Army
   Frederick, Maryland--.

Signed and Sealed this
Twelfth Day of March, 2013

Teresa Stanek Rea
*Acting Director of the United States Patent and Trademark Office*

SEQUENCE LISTING

```
<160> NUMBER OF SEQ ID NOS: 341

<210> SEQ ID NO 1
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 1
gaauaaaaac cguuauguut t                                          21

<210> SEQ ID NO 2
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 2
aacauaacgg uuuuuauuct t                                          21

<210> SEQ ID NO 3
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 3
aaccguuaug uugacauuct t                                          21

<210> SEQ ID NO 4
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
```

```
<400> SEQUENCE: 4
gaaugucaac auaacgguut t                                          21

<210> SEQ ID NO 5
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 5
ucugauuauu gugacaucat t                                          21

<210> SEQ ID NO 6
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 6
ugaugucaca auaaucagat t                                          21

<210> SEQ ID NO 7
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 7
aaaaaccguu auguugacat t                                          21

<210> SEQ ID NO 8
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 8
ugucaacaua acgguuuuut t                                          21

<210> SEQ ID NO 9
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
```

```
<400> SEQUENCE: 9
acccaggaaa uacauugcut t                                           21

<210> SEQ ID NO 10
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 10
agcaauguau uuccugggut t                                           21

<210> SEQ ID NO 11
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 11
cagaauaaaa accguuaugt t                                           21

<210> SEQ ID NO 12
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 12
cauaacgguu uuuauucugt t                                           21

<210> SEQ ID NO 13
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 13
agaauaaaaa ccguuaugut t                                           21

<210> SEQ ID NO 14
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
```

```
<400> SEQUENCE: 14
acauaacggu uuuuauucut t                                              21

<210> SEQ ID NO 15
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 15
caguuauugu cauggucact t                                              21

<210> SEQ ID NO 16
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 16
gugaccauga caauaacugt t                                              21

<210> SEQ ID NO 17
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 17
aauaaaaacc guuauguugt t                                              21

<210> SEQ ID NO 18
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 18
caacauaacg guuuuuauut t                                              21

<210> SEQ ID NO 19
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
```

<400> SEQUENCE: 19
caggaaauac auugcugcat t                                          21

<210> SEQ ID NO 20
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 20
ugcagcaaug uauuuccugt t                                          21

<210> SEQ ID NO 21
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 21
aaaccguuau guugacauut t                                          21

<210> SEQ ID NO 22
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 22
aaugucaaca uaacgguuut t                                          21

<210> SEQ ID NO 23
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 23
aaaaccguua uguugacaut t                                          21

<210> SEQ ID NO 24
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 24
augucaacau aacgguuuut t                                          21

<210> SEQ ID NO 25
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 25
ccguuauguu gacauucuut t                                          21

<210> SEQ ID NO 26
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 26
aagaauguca acauaacggt t                                          21

<210> SEQ ID NO 27
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 27
accguuaugu ugacauucut t                                          21

<210> SEQ ID NO 28
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 28
agaaugucaa cauaacggut t                                          21

<210> SEQ ID NO 29
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

```
<400> SEQUENCE: 29
uaaaaaccgu uauguugact t                                              21

<210> SEQ ID NO 30
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 30
gucaacauaa cgguuuuuat t                                              21

<210> SEQ ID NO 31
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 31
cguuauguug acauucuuct t                                              21

<210> SEQ ID NO 32
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 32
gaagaauguc aacauaacgt t                                              21

<210> SEQ ID NO 33
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 33
acaguuauug ucauggucat t                                              21

<210> SEQ ID NO 34
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
```

<400> SEQUENCE: 34
ugaccaugac aauaacugut t                                              21

<210> SEQ ID NO 35
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 35
ugauuauugu gacaucaaut t                                              21

<210> SEQ ID NO 36
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 36
auugauguca caauaaucat t                                              21

<210> SEQ ID NO 37
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 37
gauuauugug acaucaauat t                                              21

<210> SEQ ID NO 38
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 38
uauugauguc acaauaauct t                                              21

<210> SEQ ID NO 39
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide -continued

<400> SEQUENCE: 39
aggaaauaca uugcugcact t        21

<210> SEQ ID NO 40
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 40
gugcagcaau guauuuccut t        21

<210> SEQ ID NO 41
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 41
uugaaaggga ugaugaaaat t        21

<210> SEQ ID NO 42
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 42
uuuucaucau cccuuucaat t        21

<210> SEQ ID NO 43
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 43
auaaaaaccg uuauguugat t        21

<210> SEQ ID NO 44
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

```
<400> SEQUENCE: 44
ucaacauaac gguuuuuaut t                                              21

<210> SEQ ID NO 45
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 45
cugauuauug ugacaucaat t                                              21

<210> SEQ ID NO 46
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 46
uugaugucac aauaaucagt t                                              21

<210> SEQ ID NO 47
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 47
cccaggaaau acauugcugt t                                              21

<210> SEQ ID NO 48
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 48
cagcaaugua uuuccugggt t                                              21

<210> SEQ ID NO 49
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
```

-continued

<400> SEQUENCE: 49
ggaaauacau ugcugcacat t                                              21

<210> SEQ ID NO 50
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 50
ugugcagcaa uguauuucct t                                              21

<210> SEQ ID NO 51
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 51
cacaguuauu gucaugguct t                                              21

<210> SEQ ID NO 52
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 52
gaccaugaca auaacugugt t                                              21

<210> SEQ ID NO 53
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 53
aagaaggaaa caggaacaat t                                              21

<210> SEQ ID NO 54
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 54 uguuccugu uccuucuut t                                              21

<210> SEQ ID NO 55
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 55
auuauuguga caucaauagt t                                            21

<210> SEQ ID NO 56
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 56
cuauugaugu cacaauaaut t                                            21

<210> SEQ ID NO 57
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 57
ccaggaaaua cauugcugct t                                            21

<210> SEQ ID NO 58
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 58
gcagcaaugu auuccuggt t                                             21

<210> SEQ ID NO 59
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 59
augugaagaa ggaaacaggt t                                              21

<210> SEQ ID NO 60
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 60
ccuguuuccu ucuucacaut t                                              21

<210> SEQ ID NO 61
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 61
uuauugugac aucaauagct t                                              21

<210> SEQ ID NO 62
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 62
gcuauugaug ucacaauaat t                                              21

<210> SEQ ID NO 63
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 63
gaacccagga aauacauugt t                                              21

<210> SEQ ID NO 64
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide -continued

<400> SEQUENCE: 64
caauguauuu ccugggumct t                                              21

<210> SEQ ID NO 65
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 65
aacccaggaa auacauugct t                                              21

<210> SEQ ID NO 66
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 66
gcaauguauu uccuggguut t                                              21

<210> SEQ ID NO 67
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 67
gccacaguua uugucauggt t                                              21

<210> SEQ ID NO 68
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 68
ccaugacaau aacuguggct t                                              21

<210> SEQ ID NO 69
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

```
<400> SEQUENCE: 69
cgaugugaag aaggaaacat t                                              21

<210> SEQ ID NO 70
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 70 uguuccuuc uucacaucgt t                                               21

<210> SEQ ID NO 71
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 71
gaugugaaga aggaaacagt t                                              21

<210> SEQ ID NO 72
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 72
cuguuuccuu cuucacauct t                                              21

<210> SEQ ID NO 73
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 73
ugugaagaag gaaacaggat t                                              21

<210> SEQ ID NO 74
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
```

<400> SEQUENCE: 74
uccuguuucc uucuucacat t                                            21

<210> SEQ ID NO 75
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 75
gugaagaagg aaacaggaat t                                            21

<210> SEQ ID NO 76
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 76
uuccuguuuc cuucuucact t                                            21

<210> SEQ ID NO 77
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 77
guuauguuga cauucuucct t                                            21

<210> SEQ ID NO 78
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 78
ggaagaaugu caacauaact t                                            21

<210> SEQ ID NO 79
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

```
<400> SEQUENCE: 79
ccacaguuau ugucauggut t                                              21

<210> SEQ ID NO 80
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 80
accaugacaa uaacuguggt t                                              21

<210> SEQ ID NO 81
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 81
aaggaaacag gaacaagugt t                                              21

<210> SEQ ID NO 82
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 82
cacuuguucc uguuuccuut t                                              21

<210> SEQ ID NO 83
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 83
gaagaaggaa acaggaacat t                                              21

<210> SEQ ID NO 84
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
```

<400> SEQUENCE: 84 uguccuguu uccuucuuct t					21

<210> SEQ ID NO 85
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 85
uggcugaauu ucagagcaut t					21

<210> SEQ ID NO 86
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 86
augcucugaa auucagccat t					21

<210> SEQ ID NO 87
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 87
guugaaaggg augaugaaat t					21

<210> SEQ ID NO 88
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 88
uuucaucauc ccuuucaact t					21

<210> SEQ ID NO 89
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 89
cuggcugaau uucagagcat t                                              21

<210> SEQ ID NO 90
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 90
ugcucugaaa uucagccagt t                                              21

<210> SEQ ID NO 91
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 91
uucugauuau ugugacauct t                                              21

<210> SEQ ID NO 92
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 92
gaugucacaa uaaucagaat t                                              21

<210> SEQ ID NO 93
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 93
agaaggaaac aggaacaagt t                                              21

<210> SEQ ID NO 94
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

```
<400> SEQUENCE: 94
cuuguuccug uuuccuucut t                                              21

<210> SEQ ID NO 95
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 95
uuucugauua uugugacaut t                                              21

<210> SEQ ID NO 96
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 96
augucacaau aaucagaaat t                                              21

<210> SEQ ID NO 97
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 97
cagaauaaaa accguuaugu uga                                            23

<210> SEQ ID NO 98
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 98
aaaaccguua uguugacauu cuu                                            23

<210> SEQ ID NO 99
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 99
uuucugauua uugugacauc aau                                            23

<210> SEQ ID NO 100
<211> LENGTH: 23
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 100
auaaaaaccg uuauguugac auu                                           23

<210> SEQ ID NO 101
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 101
gaacccagga aauacauugc ugc                                           23

<210> SEQ ID NO 102
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 102
accagaauaa aaaccguuau guu                                           23

<210> SEQ ID NO 103
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 103
ccagaauaaa aaccguuaug uug                                           23

<210> SEQ ID NO 104
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 104
cacaguuauu gucaugguca cuc                                           23

<210> SEQ ID NO 105
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 105
agaauaaaaa ccguuauguu gac                                           23

<210> SEQ ID NO 106
<211> LENGTH: 23
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 106
cccaggaaau acauugcugc aca                                              23

<210> SEQ ID NO 107
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 107
aaaaaccguu auguugacau ucu                                              23

<210> SEQ ID NO 108
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 108
uaaaaaccgu uauguugaca uuc                                              23

<210> SEQ ID NO 109
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 109
aaccguuaug uugacauucu ucc                                              23

<210> SEQ ID NO 110
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 110
aaaccguuau guugacauuc uuc                                              23

<210> SEQ ID NO 111
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 111
aauaaaaacc guuauguuga cau                                              23

<210> SEQ ID NO 112
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 112
accguuaugu ugacauucuu ccu                                              23

<210> SEQ ID NO 113
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 113
ccacaguuau ugucaugguc acu                                              23

<210> SEQ ID NO 114
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 114
ucugauuauu gugacaucaa uag                                              23

<210> SEQ ID NO 115
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 115
cugauuauug ugacaucaau agc                                              23

<210> SEQ ID NO 116
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 116
ccaggaaaua cauugcugca caa                                              23

<210> SEQ ID NO 117
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 117
uguugaaagg gaugaugaaa aac                                              23

<210> SEQ ID NO 118
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 118
```
gaauaaaaac cguuauguug aca                                        23

<210> SEQ ID NO 119
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 119
uucugauuau ugugacauca aua                                        23

<210> SEQ ID NO 120
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 120
aacccaggaa auacauugcu gca                                        23

<210> SEQ ID NO 121
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 121
caggaaauac auugcugcac aag                                        23

<210> SEQ ID NO 122
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 122
gccacaguua uugucauggu cac                                        23

<210> SEQ ID NO 123
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 123
ugaagaagga aacaggaaca agu                                        23

<210> SEQ ID NO 124
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 124
ugauuauugu gacaucaaua gcc                                        23

```
<210> SEQ ID NO 125
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 125
acccaggaaa uacauugcug cac                                              23

<210> SEQ ID NO 126
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 126
cgaugugaag aaggaaacag gaa                                              23

<210> SEQ ID NO 127
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 127
gauuauugug acaucaauag ccc                                              23

<210> SEQ ID NO 128
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 128
aagaacccag gaaauacauu gcu                                              23

<210> SEQ ID NO 129
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 129
agaacccagg aaauacauug cug                                              23

<210> SEQ ID NO 130
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 130
aagccacagu uauugucaug guc                                              23
```

```
<210> SEQ ID NO 131
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 131
cucgauguga agaaggaaac agg                                              23

<210> SEQ ID NO 132
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 132
ucgaugugaa gaaggaaaca gga                                              23

<210> SEQ ID NO 133
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 133
gaugugaaga aggaaacagg aac                                              23

<210> SEQ ID NO 134
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 134
augugaagaa ggaaacagga aca                                              23

<210> SEQ ID NO 135
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 135
ccguuauguu gacauucuuc cuu                                              23

<210> SEQ ID NO 136
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 136
agccacaguu auugucaugg uca                                              23

<210> SEQ ID NO 137
<211> LENGTH: 23
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 137
agaaggaaac aggaacaagu gug                                              23

<210> SEQ ID NO 138
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 138
gugaagaagg aaacaggaac aag                                              23

<210> SEQ ID NO 139
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 139
ucuggcugaa uuucagagca ucc                                              23

<210> SEQ ID NO 140
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 140
uuguugaaag ggaugaugaa aaa                                              23

<210> SEQ ID NO 141
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 141
uucuggcuga auuucagagc auc                                              23

<210> SEQ ID NO 142
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 142
auuucugauu auugugacau caa                                              23

<210> SEQ ID NO 143
<211> LENGTH: 23
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 143
gaagaaggaa acaggaacaa gug                                              23

<210> SEQ ID NO 144
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 144
cauuucugau uauugugaca uca                                              23

<210> SEQ ID NO 145
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 145
ccacaugaag cagcacgacu u                                                21

<210> SEQ ID NO 146
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 146
aagucgugcu gcuucaugug guc                                              23

<210> SEQ ID NO 147
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 147
gaauaaaaac cguuauguu                                                   19

<210> SEQ ID NO 148
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 148
aacauaacgg uuuuuauuc                                                   19

<210> SEQ ID NO 149
<211> LENGTH: 19
<212> TYPE: RNA
<213> ORGANISM: Artificial Sequence
<220> FEATURE:
<223> OTHER INFORMATION: Description of Artificial Sequence: Synthetic
```

```
                             oligonucleotide

<400> SEQUENCE: 149
aaccguuaug uugacauuc                                                19

<210> SEQ ID NO 150
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 150
gaaugucaac auaacgguu                                                19

<210> SEQ ID NO 151
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 151
ucugauuauu gugacauca                                                19

<210> SEQ ID NO 152
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 152
ugaugucaca auaaucaga                                                19

<210> SEQ ID NO 153
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 153
aaaaaccguu auguugaca                                                19

<210> SEQ ID NO 154
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 154
ugucaacaua acgguuuuu                                                19

<210> SEQ ID NO 155
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
```

-continued

```
<400> SEQUENCE: 155
acccaggaaa uacauugcu                                                19

<210> SEQ ID NO 156
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 156
agcaauguau uuccugggu                                                19

<210> SEQ ID NO 157
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 157
cagaauaaaa accguuaug                                                19

<210> SEQ ID NO 158
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 158
cauaacgguu uuuauucug                                                19

<210> SEQ ID NO 159
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 159
agaauaaaaa ccguuaugu                                                19

<210> SEQ ID NO 160
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 160
acauaacggu uuuuauucu                                                19

<210> SEQ ID NO 161
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 161
```
caguuauugu cauggucac 19

<210> SEQ ID NO 162
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 162
gugaccauga caauaacug 19

<210> SEQ ID NO 163
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 163
aauaaaaacc guuauguug 19

<210> SEQ ID NO 164
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 164
caacauaacg guuuuuauu 19

<210> SEQ ID NO 165
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 165
caggaaauac auugcugca 19

<210> SEQ ID NO 166
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 166
ugcagcaaug uauuuccug 19

<210> SEQ ID NO 167
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 167
aaaccguuau guugacauu 19

```
<210> SEQ ID NO 168
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 168
aaugucaaca uaacgguuu                                                    19

<210> SEQ ID NO 169
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 169
aaaaccguua uguugacau                                                    19

<210> SEQ ID NO 170
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 170
augucaacau aacgguuuu                                                    19

<210> SEQ ID NO 171
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 171
ccguuauguu gacauucuu                                                    19

<210> SEQ ID NO 172
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 172
aagaauguca acauaacgg                                                    19

<210> SEQ ID NO 173
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 173
accguuaugu ugacauucu                                                    19

<210> SEQ ID NO 174
```

```
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 174
agaaugucaa cauaacggu                                                        19

<210> SEQ ID NO 175
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 175
uaaaaaccgu uauguugac                                                        19

<210> SEQ ID NO 176
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 176
gucaacauaa cgguuuuua                                                        19

<210> SEQ ID NO 177
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 177
cguuauguug acauucuuc                                                        19

<210> SEQ ID NO 178
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 178
gaagaauguc aacauaacg                                                        19

<210> SEQ ID NO 179
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 179
acaguuauug ucaugguca                                                        19

<210> SEQ ID NO 180
<211> LENGTH: 19
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 180
ugaccaugac aauaacugu                                                    19

<210> SEQ ID NO 181
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 181
ugauuauugu gacaucaau                                                    19

<210> SEQ ID NO 182
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 182
auugauguca caauaauca                                                    19

<210> SEQ ID NO 183
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 183
gauuauugug acaucaaua                                                    19

<210> SEQ ID NO 184
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 184
uauugauguc acaauaauc                                                    19

<210> SEQ ID NO 185
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 185
aggaaauaca uugcugcac                                                    19

<210> SEQ ID NO 186
<211> LENGTH: 19
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 186
gugcagcaau guauuuccu                                                    19

<210> SEQ ID NO 187
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 187
uugaaaggga ugaugaaaa                                                    19

<210> SEQ ID NO 188
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 188
uuuucaucau cccuuucaa                                                    19

<210> SEQ ID NO 189
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 189
auaaaaaccg uuauguuga                                                    19

<210> SEQ ID NO 190
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 190
ucaacauaac gguuuuuau                                                    19

<210> SEQ ID NO 191
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 191
cugauuauug ugacaucaa                                                    19

<210> SEQ ID NO 192
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 192
uugaugucac aauaaucag                                                19

<210> SEQ ID NO 193
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 193
cccaggaaau acauugcug                                                19

<210> SEQ ID NO 194
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 194
cagcaaugua uuuccuggg                                                19

<210> SEQ ID NO 195
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 195
ggaaauacau ugcugcaca                                                19

<210> SEQ ID NO 196
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 196
ugugcagcaa uguauuucc                                                19

<210> SEQ ID NO 197
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 197
cacaguuauu gucaugguc                                                19

<210> SEQ ID NO 198
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 198
```

```
gaccaugaca auaacugug                                              19

<210> SEQ ID NO 199
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 199
aagaaggaaa caggaacaa                                              19

<210> SEQ ID NO 200
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 200
uuguuccugu uuccuucuu                                              19

<210> SEQ ID NO 201
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 201
auuauuguga caucaauag                                              19

<210> SEQ ID NO 202
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 202
cuauugaugu cacaauaau                                              19

<210> SEQ ID NO 203
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 203
ccaggaaaua cauugcugc                                              19

<210> SEQ ID NO 204
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 204
gcagcaaugu auuuccugg                                              19
```

```
<210> SEQ ID NO 205
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 205
augugaagaa ggaaacagg                                              19

<210> SEQ ID NO 206
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 206 ccuguuccu ucuucacau                                               19

<210> SEQ ID NO 207
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 207
uuauugugac aucaauagc                                              19

<210> SEQ ID NO 208
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 208
gcuauugaug ucacaauaa                                              19

<210> SEQ ID NO 209
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 209
gaacccagga aauacauug                                              19

<210> SEQ ID NO 210
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 210
caauguauuu ccuggguuc                                              19
```

```
<210> SEQ ID NO 211
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 211
aacccaggaa auacauugc                                                    19

<210> SEQ ID NO 212
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 212
gcaauguauu uccuggguu                                                    19

<210> SEQ ID NO 213
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 213
gccacaguua uugucaugg                                                    19

<210> SEQ ID NO 214
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 214
ccaugacaau aacuguggc                                                    19

<210> SEQ ID NO 215
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 215
cgaugugaag aaggaaaca                                                    19

<210> SEQ ID NO 216
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 216 uguuccuuc uucacaucg                                                     19

<210> SEQ ID NO 217
<211> LENGTH: 19
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 217
gaugugaaga aggaaacag                                                 19

<210> SEQ ID NO 218
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 218 cuguuccuu cuucacauc                                                  19

<210> SEQ ID NO 219
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 219
ugugaagaag gaaacagga                                                 19

<210> SEQ ID NO 220
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 220
uccuguuucc uucuucaca                                                 19

<210> SEQ ID NO 221
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 221
gugaagaagg aaacaggaa                                                 19

<210> SEQ ID NO 222
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 222
uuccuguuuc cuucuucac                                                 19

<210> SEQ ID NO 223
<211> LENGTH: 19
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 223
guuauguuga cauucuucc                                                 19

<210> SEQ ID NO 224
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 224
ggaagaaugu caacauaac                                                 19

<210> SEQ ID NO 225
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 225
ccacaguuau ugucauggu                                                 19

<210> SEQ ID NO 226
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 226
accaugacaa uaacugugg                                                 19

<210> SEQ ID NO 227
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 227
aaggaaacag gaacaagug                                                 19

<210> SEQ ID NO 228
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 228
cacuuguucc uguuuccuu                                                 19

<210> SEQ ID NO 229
<211> LENGTH: 19
<212> TYPE: RNA
<213> ORGANISM: Artificial Sequence
<220> FEATURE:
<223> OTHER INFORMATION: Description of Artificial Sequence: Synthetic
```

```
                                    oligonucleotide

<400> SEQUENCE: 229
gaagaaggaa acaggaaca                                                19

<210> SEQ ID NO 230
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 230
uguuccuguu uccuucuuc                                                19

<210> SEQ ID NO 231
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 231
uggcugaauu ucagagcau                                                19

<210> SEQ ID NO 232
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 232
augcucugaa auucagcca                                                19

<210> SEQ ID NO 233
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 233
guugaaaggg augaugaaa                                                19

<210> SEQ ID NO 234
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 234
uuucaucauc ccuuucaac                                                19

<210> SEQ ID NO 235
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
```

-continued

```
<400> SEQUENCE: 235
cuggcugaau uucagagca                                               19

<210> SEQ ID NO 236
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 236
ugcucugaaa uucagccag                                               19

<210> SEQ ID NO 237
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 237
uucugauuau ugugacauc                                               19

<210> SEQ ID NO 238
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 238
gaugucacaa uaaucagaa                                               19

<210> SEQ ID NO 239
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 239
agaaggaaac aggaacaag                                               19

<210> SEQ ID NO 240
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 240 cuuguccug uuuccuucu                                                19

<210> SEQ ID NO 241
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 241
```
uuucugauua uugugacau                                          19

<210> SEQ ID NO 242
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 242
augucacaau aaucagaaa                                          19

<210> SEQ ID NO 243
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: a, c, g, u or t

<400> SEQUENCE: 243
gaauaaaaac cguuauguun n                                       21

<210> SEQ ID NO 244
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: a, c, g, u or t

<400> SEQUENCE: 244
aacauaacgg uuuuuauucn n                                       21

<210> SEQ ID NO 245
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: a, c, g, u or t

<400> SEQUENCE: 245
aaccguuaug uugacauucn n                                       21

<210> SEQ ID NO 246
<211> LENGTH: 21
<212> TYPE: DNA
<213> ORGANISM: Artificial Sequence

```
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: a, c, g, u or t

<400> SEQUENCE: 246
gaaugucaac auaacgguun n                                               21

<210> SEQ ID NO 247
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: a, c, g, u or t

<400> SEQUENCE: 247
ucugauuauu gugacaucan n                                               21

<210> SEQ ID NO 248
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: a, c, g, u or t

<400> SEQUENCE: 248
ugaugucaca auaaucagan n                                               21

<210> SEQ ID NO 249
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: a, c, g, u or t

<400> SEQUENCE: 249
aaaaaccguu auguugacan n                                               21

<210> SEQ ID NO 250
<211> LENGTH: 21
<212> TYPE: DNA
<213> ORGANISM: Artificial Sequence
```

```
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: a, c, g, u or t

<400> SEQUENCE: 250
ugucaacaua acgguuuuun n                                                    21

<210> SEQ ID NO 251
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: a, c, g, u or t

<400> SEQUENCE: 251
acccaggaaa uacauugcun n                                                    21

<210> SEQ ID NO 252
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: a, c, g, u or t

<400> SEQUENCE: 252
agcaauguau uuccugggun n                                                    21

<210> SEQ ID NO 253
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: a, c, g, u or t

<400> SEQUENCE: 253
cagaauaaaa accguuaugn n                                                    21

<210> SEQ ID NO 254
<211> LENGTH: 21
<212> TYPE: DNA
<213> ORGANISM: Artificial Sequence
```

```
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: a, c, g, u or t

<400> SEQUENCE: 254
cauaacgguu uuuauucugn n                                              21

<210> SEQ ID NO 255
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: a, c, g, u or t

<400> SEQUENCE: 255
agaauaaaaa ccguuaugun n                                              21

<210> SEQ ID NO 256
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: a, c, g, u or t

<400> SEQUENCE: 256
acauaacggu uuuuauucun n                                              21

<210> SEQ ID NO 257
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: a, c, g, u or t

<400> SEQUENCE: 257
caguuauugu cauggucacn n                                              21

<210> SEQ ID NO 258
<211> LENGTH: 21
<212> TYPE: DNA
<213> ORGANISM: Artificial Sequence
```

```
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: a, c, g, u or t

<400> SEQUENCE: 258
gugaccauga caauaacugn n                                            21

<210> SEQ ID NO 259
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: a, c, g, u or t

<400> SEQUENCE: 259
aauaaaaacc guuauguugn n                                            21

<210> SEQ ID NO 260
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: a, c, g, u or t

<400> SEQUENCE: 260
caacauaacg guuuuuauun n                                            21

<210> SEQ ID NO 261
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: a, c, g, u or t

<400> SEQUENCE: 261
caggaaauac auugcugcan n                                            21

<210> SEQ ID NO 262
<211> LENGTH: 21
<212> TYPE: DNA
<213> ORGANISM: Artificial Sequence
```

```
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: a, c, g, u or t

<400> SEQUENCE: 262
ugcagcaaug uauuuccugn n                                            21

<210> SEQ ID NO 263
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: a, c, g, u or t

<400> SEQUENCE: 263
aaaccguuau guugacauun n                                            21

<210> SEQ ID NO 264
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: a, c, g, u or t

<400> SEQUENCE: 264
aaugucaaca uaacgguuun n                                            21

<210> SEQ ID NO 265
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: a, c, g, u or t

<400> SEQUENCE: 265 aaaccguua uguugacaun n                                             21

<210> SEQ ID NO 266
<211> LENGTH: 21
<212> TYPE: DNA
<213> ORGANISM: Artificial Sequence
```

```
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: a, c, g, u or t

<400> SEQUENCE: 266
augucaacau aacgguuuun n                                           21

<210> SEQ ID NO 267
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: a, c, g, u or t

<400> SEQUENCE: 267
ccguuauguu gacauucuun n                                           21

<210> SEQ ID NO 268
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: a, c, g, u or t

<400> SEQUENCE: 268
aagaauguca acauaacggn n                                           21

<210> SEQ ID NO 269
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: a, c, g, u or t

<400> SEQUENCE: 269
accguuaugu ugacauucun n                                           21

<210> SEQ ID NO 270
<211> LENGTH: 21
<212> TYPE: DNA
<213> ORGANISM: Artificial Sequence
```

```
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: a, c, g, u or t

<400> SEQUENCE: 270
agaaugucaa cauaacggun n                                             21

<210> SEQ ID NO 271
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: a, c, g, u or t

<400> SEQUENCE: 271
uaaaaaccgu uauguugacn n                                             21

<210> SEQ ID NO 272
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: a, c, g, u or t

<400> SEQUENCE: 272
gucaacauaa cgguuuuuan n                                             21

<210> SEQ ID NO 273
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: a, c, g, u or t

<400> SEQUENCE: 273
cguuauguug acauucuucn n                                             21

<210> SEQ ID NO 274
<211> LENGTH: 21
<212> TYPE: DNA
<213> ORGANISM: Artificial Sequence
```

```
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: a, c, g, u or t

<400> SEQUENCE: 274
gaagaauguc aacauaacgn n                                                21

<210> SEQ ID NO 275
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: a, c, g, u or t

<400> SEQUENCE: 275
acaguuauug ucauggucan n                                                21

<210> SEQ ID NO 276
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: a, c, g, u or t

<400> SEQUENCE: 276
ugaccaugac aauaacugun n                                                21

<210> SEQ ID NO 277
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: a, c, g, u or t

<400> SEQUENCE: 277
ugauuauugu gacaucaaun n                                                21

<210> SEQ ID NO 278
<211> LENGTH: 21
<212> TYPE: DNA
<213> ORGANISM: Artificial Sequence
```

```
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: a, c, g, u or t

<400> SEQUENCE: 278
auugauguca caauaaucan n                                                   21

<210> SEQ ID NO 279
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: a, c, g, u or t

<400> SEQUENCE: 279
gauuauugug acaucaauan n                                                   21

<210> SEQ ID NO 280
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: a, c, g, u or t

<400> SEQUENCE: 280
uauugauguc acaauaaucn n                                                   21

<210> SEQ ID NO 281
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: a, c, g, u or t

<400> SEQUENCE: 281
aggaaauaca uugcugcacn n                                                   21

<210> SEQ ID NO 282
<211> LENGTH: 21
<212> TYPE: DNA
<213> ORGANISM: Artificial Sequence
```

```
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: a, c, g, u or t

<400> SEQUENCE: 282
gugcagcaau guauuuccun n                                              21

<210> SEQ ID NO 283
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: a, c, g, u or t

<400> SEQUENCE: 283
uugaaaggga ugaugaaaan n                                              21

<210> SEQ ID NO 284
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: a, c, g, u or t

<400> SEQUENCE: 284
uuuucaucau cccuuucaan n                                              21

<210> SEQ ID NO 285
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: a, c, g, u or t

<400> SEQUENCE: 285
auaaaaaccg uuauguugan n                                              21

<210> SEQ ID NO 286
<211> LENGTH: 21
<212> TYPE: DNA
<213> ORGANISM: Artificial Sequence
```

```
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: a, c, g, u or t

<400> SEQUENCE: 286
ucaacauaac gguuuuuaun n                                                    21

<210> SEQ ID NO 287
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: a, c, g, u or t

<400> SEQUENCE: 287
cugauuauug ugacaucaan n                                                    21

<210> SEQ ID NO 288
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: a, c, g, u or t

<400> SEQUENCE: 288
uugaugucac aauaaucagn n                                                    21

<210> SEQ ID NO 289
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: a, c, g, u or t

<400> SEQUENCE: 289
cccaggaaau acauugcugn n                                                    21

<210> SEQ ID NO 290
<211> LENGTH: 21
<212> TYPE: DNA
<213> ORGANISM: Artificial Sequence
```

```
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: a, c, g, u or t

<400> SEQUENCE: 290
cagcaaugua uuuccugggn n                                              21

<210> SEQ ID NO 291
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: a, c, g, u or t

<400> SEQUENCE: 291
ggaaauacau ugcugcacan n                                              21

<210> SEQ ID NO 292
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: a, c, g, u or t

<400> SEQUENCE: 292
ugugcagcaa uguauuuccn n                                              21

<210> SEQ ID NO 293
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: a, c, g, u or t

<400> SEQUENCE: 293
cacaguuauu gucauggucn n                                              21

<210> SEQ ID NO 294
<211> LENGTH: 21
<212> TYPE: DNA
<213> ORGANISM: Artificial Sequence
```

```
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: a, c, g, u or t

<400> SEQUENCE: 294
gaccaugaca auaacugugn n                                              21

<210> SEQ ID NO 295
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: a, c, g, u or t

<400> SEQUENCE: 295
aagaaggaaa caggaacaan n                                              21

<210> SEQ ID NO 296
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: a, c, g, u or t

<400> SEQUENCE: 296
uuguuccugu uuccuucuun n                                              21

<210> SEQ ID NO 297
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: a, c, g, u or t

<400> SEQUENCE: 297
auuauuguga caucaauagn n                                              21

<210> SEQ ID NO 298
<211> LENGTH: 21
<212> TYPE: DNA
<213> ORGANISM: Artificial Sequence
```

```
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: a, c, g, u or t

<400> SEQUENCE: 298
cuauugaugu cacaauaaun n                                              21

<210> SEQ ID NO 299
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: a, c, g, u or t

<400> SEQUENCE: 299
ccaggaaaua cauugcugcn n                                              21

<210> SEQ ID NO 300
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: a, c, g, u or t

<400> SEQUENCE: 300
gcagcaaugu auuuccuggn n                                              21

<210> SEQ ID NO 301
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: a, c, g, u or t

<400> SEQUENCE: 301
augugaagaa ggaaacaggn n                                              21

<210> SEQ ID NO 302
<211> LENGTH: 21
<212> TYPE: DNA
<213> ORGANISM: Artificial Sequence
```

```
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: a, c, g, u or t

<400> SEQUENCE: 302
ccuguuuccu ucuucacaun n                                              21

<210> SEQ ID NO 303
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: a, c, g, u or t

<400> SEQUENCE: 303
uuauugugac aucaauagcn n                                              21

<210> SEQ ID NO 304
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: a, c, g, u or t

<400> SEQUENCE: 304
gcuauugaug ucacaauaan n                                              21

<210> SEQ ID NO 305
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: a, c, g, u or t

<400> SEQUENCE: 305
gaacccagga aauacauugn n                                              21

<210> SEQ ID NO 306
<211> LENGTH: 21
<212> TYPE: DNA
<213> ORGANISM: Artificial Sequence
```

```
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: a, c, g, u or t

<400> SEQUENCE: 306
caauguauuu ccuggguucn n                                            21

<210> SEQ ID NO 307
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: a, c, g, u or t

<400> SEQUENCE: 307
aacccaggaa auacauugcn n                                            21

<210> SEQ ID NO 308
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: a, c, g, u or t

<400> SEQUENCE: 308
gcaauguauu uccuggguun n                                            21

<210> SEQ ID NO 309
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: a, c, g, u or t

<400> SEQUENCE: 309
gccacaguua uugucauggn n                                            21

<210> SEQ ID NO 310
<211> LENGTH: 21
<212> TYPE: DNA
<213> ORGANISM: Artificial Sequence
```

```
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: a, c, g, u or t

<400> SEQUENCE: 310
ccaugacaau aacugugggcn n                                              21

<210> SEQ ID NO 311
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: a, c, g, u or t

<400> SEQUENCE: 311
cgaugugaag aaggaaacan n                                               21

<210> SEQ ID NO 312
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: a, c, g, u or t

<400> SEQUENCE: 312 uguuccuuc uucacaucgn n                                                21

<210> SEQ ID NO 313
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: a, c, g, u or t

<400> SEQUENCE: 313
gaugugaaga aggaaacagn n                                               21

<210> SEQ ID NO 314
<211> LENGTH: 21
<212> TYPE: DNA
<213> ORGANISM: Artificial Sequence
```

```
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: a, c, g, u or t

<400> SEQUENCE: 314 cguuuccuu cuucacaucn n                                              21

<210> SEQ ID NO 315
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: a, c, g, u or t

<400> SEQUENCE: 315
ugugaagaag gaaacaggan n                                             21

<210> SEQ ID NO 316
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: a, c, g, u or t

<400> SEQUENCE: 316
uccuguuucc uucuucacan n                                             21

<210> SEQ ID NO 317
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: a, c, g, u or t

<400> SEQUENCE: 317
gugaagaagg aaacaggaan n                                             21

<210> SEQ ID NO 318
<211> LENGTH: 21
<212> TYPE: DNA
<213> ORGANISM: Artificial Sequence
```

```
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: a, c, g, u or t

<400> SEQUENCE: 318
uuccuguuuc cuucuucacn n                                              21

<210> SEQ ID NO 319
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: a, c, g, u or t

<400> SEQUENCE: 319
guuauguuga cauucuuccn n                                              21

<210> SEQ ID NO 320
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: a, c, g, u or t

<400> SEQUENCE: 320
ggaagaaugu caacauaacn n                                              21

<210> SEQ ID NO 321
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: a, c, g, u or t

<400> SEQUENCE: 321
ccacaguuau ugucauggun n                                              21

<210> SEQ ID NO 322
<211> LENGTH: 21
<212> TYPE: DNA
<213> ORGANISM: Artificial Sequence
```

-continued

```
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: a, c, g, u or t

<400> SEQUENCE: 322
accaugacaa uaacuguggn n                                              21

<210> SEQ ID NO 323
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: a, c, g, u or t

<400> SEQUENCE: 323
aaggaaacag gaacaagugn n                                              21

<210> SEQ ID NO 324
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: a, c, g, u or t

<400> SEQUENCE: 324
cacuuguucc uguuuccuun n                                              21

<210> SEQ ID NO 325
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: a, c, g, u or t

<400> SEQUENCE: 325
gaagaaggaa acaggaacan n                                              21

<210> SEQ ID NO 326
<211> LENGTH: 21
<212> TYPE: DNA
<213> ORGANISM: Artificial Sequence
```

```
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: a, c, g, u or t

<400> SEQUENCE: 326
uguuccuguu uccuucuucn n                                                   21

<210> SEQ ID NO 327
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: a, c, g, u or t

<400> SEQUENCE: 327
uggcugaauu ucagagcaun n                                                   21

<210> SEQ ID NO 328
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: a, c, g, u or t

<400> SEQUENCE: 328
augcucugaa auucagccan n                                                   21

<210> SEQ ID NO 329
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: a, c, g, u or t

<400> SEQUENCE: 329
guugaaaggg augaugaaan n                                                   21

<210> SEQ ID NO 330
<211> LENGTH: 21
<212> TYPE: DNA
<213> ORGANISM: Artificial Sequence
```

```
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: a, c, g, u or t

<400> SEQUENCE: 330
uuucaucauc ccuuucaacn n                                              21

<210> SEQ ID NO 331
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: a, c, g, u or t

<400> SEQUENCE: 331
cuggcugaau uucagagcan n                                              21

<210> SEQ ID NO 332
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: a, c, g, u or t

<400> SEQUENCE: 332
ugcucugaaa uucagccagn n                                              21

<210> SEQ ID NO 333
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: a, c, g, u or t

<400> SEQUENCE: 333
uucugauuau ugugacaucn n                                              21

<210> SEQ ID NO 334
<211> LENGTH: 21
<212> TYPE: DNA
<213> ORGANISM: Artificial Sequence
```

```
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: a, c, g, u or t

<400> SEQUENCE: 334
gaugucacaa uaaucagaan n                                              21

<210> SEQ ID NO 335
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: a, c, g, u or t

<400> SEQUENCE: 335
agaaggaaac aggaacaagn n                                              21

<210> SEQ ID NO 336
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: a, c, g, u or t

<400> SEQUENCE: 336
cuuguuccug uuuccuucun n                                              21

<210> SEQ ID NO 337
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: a, c, g, u or t

<400> SEQUENCE: 337
uuucugauua uugugacaun n                                              21

<210> SEQ ID NO 338
<211> LENGTH: 21
<212> TYPE: DNA
<213> ORGANISM: Artificial Sequence
```

```
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: a, c, g, u or t

<400> SEQUENCE: 338
augucacaau aaucagaaan n                                              21

<210> SEQ ID NO 339
<211> LENGTH: 5330
<212> TYPE: DNA
<213> ORGANISM: Homo sapiens

<400> SEQUENCE: 339 agtattttg  gagaagttag  taaaaccgaa  tctgacatca  tcacctagca  gttcatgcag     60
ctagcaagtg  gtttgttctt  agggtaacag  aggaggaaat  tgttcctcgt  ctgataagac    120
aacagtggag  aaaggacgca  tgctgtttct  tagggacacg  gctgacttcc  agatatgacc    180
atgtatttgt  ggcttaaact  cttggcattt  ggctttgcct  ttctggacac  agaagtattt    240
gtgacagggc  aaagcccaac  accttccccc  actggattga  ctacagcaaa  gatgcccagt    300
gttccacttt  caagtgaccc  cttacctact  cacaccactg  cattctcacc  cgcaagcacc    360
tttgaaagag  aaaatgactt  ctcagagacc  acaacttctc  ttagtccaga  caatacttcc    420
acccaagtat  ccccggactc  tttggataat  gctagtgctt  ttaataccac  aggtgtttca    480
tcagtacaga  cgcctcacct  tcccacgcac  gcagactcgc  agacgccctc  tgctggaact    540
gacacgcaga  cattcagcgg  ctccgccgcc  aatgcaaaac  tcaaccctac  cccaggcagc    600
aatgctatct  cagatgtccc  aggagagagg  agtacagcca  gcacctttcc  tacagaccca    660
gtttccccat  tgacaaccac  cctcagcctt  gcacaccaca  gctctgctgc  cttacctgca    720
cgcacctcca  acaccaccat  cacagcgaac  acctcagatg  cctaccttaa  tgcctctgaa    780
acaaccactc  tgagcccttc  tggaagcgct  gtcatttcaa  ccacaacaat  agctactact    840
ccatctaagc  caacatgtga  tgaaaaatat  gcaaacatca  ctgtggatta  cttatataac    900
aaggaaacta  aattatttac  agcaaagcta  aatgttaatg  agaatgtgga  atgtggaaac    960
aatacttgca  caaacaatga  ggtgcataac  cttacagaat  gtaaaaatgc  gtctgtttcc   1020
atatctcata  attcatgtac  tgctcctgat  aagacattaa  tattagatgt  gccaccaggg   1080
gttgaaaagt  ttcagttaca  tgattgtaca  caagttgaaa  aagcagatac  tactatttgt   1140
ttaaaatgga  aaaatattga  aacctttact  tgtgatacac  agaatattac  ctacagattt   1200
cagtgtggta  atatgatatt  tgataataaa  gaattaaat  tagaaaacct  tgaacccgaa   1260
catgagtata  agtgtgactc  agaaatactc  tataataacc  acaagtttac  taacgcaagt   1320
aaaattatta  aaacagattt  tgggagtcca  ggagagcctc  agattatttt  ttgtagaagt   1380
gaagctgcac  atcaaggagt  aattacctgg  aatccccctc  aaagatcatt  tcataatttt   1440
accctctgtt  atataaaaga  gacagaaaaa  gattgcctca  atctggataa  aaacctgatc   1500
aaatatgatt  tgcaaaattt  aaaaccttat  acgaaatatg  ttttatcatt  acatgcctac   1560
atcattgcaa  aagtgcaacg  taatggaagt  gctgcaatgt  gtcatttcac  aactaaaagt   1620
gctcctccaa  gccaggtctg  gaacatgact  gtctccatga  catcagataa  tagtatgcat   1680
gtcaagtgta  ggcctcccag  ggaccgtaat  ggccccatg   aacgttacca  tttggaagtt   1740
```

```
gaagctggaa atactctggt tagaaatgag tcgcataaga attgcgattt ccgtgtaaaa   1800
gatcttcaat attcaacaga ctacactttt aaggcctatt ttcacaatgg agactatcct   1860
ggagaaccct ttattttaca tcattcaaca tcttataatt ctaaggcact gatagcattt   1920
ctggcatttc tgattattgt gacatcaata gccctgcttg ttgttctcta caaaatctat   1980
gatctacata agaaaagatc ctgcaattta gatgaacagc aggagcttgt tgaaagggat   2040
gatgaaaaac aactgatgaa tgtggagcca atccatgcag atattttgtt ggaaacttat   2100
aagaggaaga ttgctgatga aggaagactt tttctggctg aatttcagag catcccgcgg   2160
gtgttcagca agtttcctat aaaggaagct cgaaagccct taaccagaa taaaaaccgt   2220
tatgttgaca ttcttcctta tgattataac cgtgttgaac tctctgagat aaacggagat   2280
gcagggtcaa actacataaa tgccagctat attgatggtt tcaaagaacc caggaaatac   2340
attgctgcac aaggtcccag ggatgaaact gttgatgatt tctggaggat gatttgggaa   2400
cagaaagcca cagttattgt catggtcact cgatgtgaag aaggaaacag gaacaagtgt   2460
gcagaatact ggccgtcaat ggaagagggc actcgggctt ttggagatgt tgttgtaaag   2520
atcaaccagc acaaaagatg tccagattac atcattcaga aattgaacat tgtaaataaa   2580
aaagaaaaag caactggaag agaggtgact cacattcagt tcaccagctg gccagaccac   2640
ggggtgcctg aggatcctca cttgctcctc aaactgagaa ggagagtgaa tgccttcagc   2700
aatttcttca gtggtcccat tgtggtgcac tgcagtgctg tgttgggcg cacaggaacc   2760
tatatcggaa ttgatgccat gctagaaggc ctggaagccg agaacaaagt ggatgtttat   2820
ggttatgttg tcaagctaag gcgacagaga tgcctgatgg ttcaagtaga ggcccagtac   2880
atcttgatcc atcaggcttt ggtggaatac aatcagtttg gagaaacaga agtgaatttg   2940
tctgaattac atccatatct acataacatg aagaaaaggg atccacccag tgagccgtct   3000
ccactagagg ctgaattcca gagacttcct tcatatagga gctggaggac acagcacatt   3060
ggaaatcaag aagaaaataa agtaaaaac aggaattcta atgtcatccc atatgactat   3120
aacagagtgc cacttaaaca tgagctggaa atgagtaaag agagtgagca tgattcagat   3180
gaatcctctg atgatgacag tgattcagag gaaccaagca aatacatcaa tgcatctttt   3240
ataatgagct actggaaacc tgaagtgatg attgctgctc agggaccact gaaggagacc   3300
attggtgact tttggcagat gatcttccaa agaaaagtca agttattgt tatgctgaca   3360
gaactgaaac atggagacca ggaaatctgt gctcagtact ggggagaagg aaagcaaaca   3420
tatggagata ttgaagttga cctgaaagac acagacaaat cttcaactta tacccttcgt   3480
gtctttgaac tgagacattc caagaggaaa gactctcgaa ctgtgtacca gtaccaatat   3540
acaaactgga gtgtggagca gcttcctgca gaacccaagg aattaatctc tatgattcag   3600
gtcgtcaaac aaaaacttcc ccagaagaat tcctctgaag gaacaagca tcacaagagt   3660
acacctctac tcattcactg cagggatgga tctcagcaaa cgggaatatt ttgtgctttg   3720
ttaaatctct tagaaagtgc ggaaacagaa gaggtagtgg atattttca agtggtaaaa   3780
gctctacgca aagctaggcc aggcatggtt tccacattcg agcaatatca attcctatat   3840
gacgtcattg ccagcaccta ccctgctcag aatggacaag taagaaaaa caaccatcaa   3900
gaagataaaa ttgaatttga taatgaagtg acaaagtaa agcaggatgc taattgtgtt   3960
aatccacttg gtgccccaga aaagctccct gaagcaaagg aacaggctga aggttctgaa   4020
cccacgagtg gcactgaggg gccagaacat tctgtcaatg gtcctgcaag tccagcttta   4080
aatcaaggtt cataggaaaa gacataaatg aggaaactcc aaacctcctg ttagctgtta   4140
```

```
tttctattttt tgtagaagta ggaagtgaaa ataggtatac agtggattaa ttaaatgcag    4200
cgaaccaata tttgtagaag ggttatattt tactactgtg gaaaaatatt taagatagtt    4260
ttgccagaac agtttgtaca gacgtatgct tattttaaaa ttttatctct tattcagtaa    4320
aaaacaactt ctttgtaatc gttatgtgtg tatatgtatg tgtgtatggg tgtgtgtttg    4380
tgtgagagac agagaaagag agagaattct ttcaagtgaa tctaaaagct tttgcttttc    4440
ctttgttttt atgaagaaaa aatacatttt atattagaag tgttaactta gcttgaagga    4500
tctgttttta aaaatcataa actgtgtgca gactcaataa aatcatgtac atttctgaaa    4560
tgacctcaag atgtcctcct tgttctactc atatatatct atcttatata gtttactatt    4620
ttacttctag agatagtaca taaaggtggt atgtgtgtgt atgctactac aaaaaagttg    4680
ttaactaaat taacattggg aaatcttata ttccatatat tagcatttag tccaatgtct    4740
ttttaagctt atttaattaa aaaatttcca gtgagcttat catgctgtct ttacatgggg    4800
ttttcaattt tgcatgctcg attattccct gtacaatatt taaaatttat tgcttgatac    4860
ttttgacaac aaattaggtt ttgtacaatt gaacttaaat aaatgtcatt aaaataaata    4920
aatgcaatat gtattaatat tcattgtata aaaatagaag aatacaaaca tatttgttaa    4980
atatttacat atgaaattta atatagctat ttttatggaa ttttttcattg atatgaaaaa    5040 tatgatattg catatgcata gttcccatgt taaatcccat tcataacttt cattaaagca    5100
tttactttga atttctccaa tgcttagaat gttttttacca ggaatggatg tcgctaatca    5160
taataaaatt caaccattat tttttttcttg tttataatac attgtgttat atgttcaaat    5220
atgaaatgtg tatgcaccta ttgaaatatg tttaatgcat ttattaacat ttgcaggaca    5280
cttttacagg ccccaattat ccaatagtct aataattgtt taagatctag                5330

<210> SEQ ID NO 340
<211> LENGTH: 5247
<212> TYPE: DNA
<213> ORGANISM: Mus musculus

<400> SEQUENCE: 340
gacatcacca tttagcagtg catgtagcta gcaagtggtt tgttcttagg gtaagagagt      60
aggaaacttg ctccccatct gataagacag agtgcaaagg agaccctatt tcttaggggc     120
acagctgatc tccagatatg accatgggtt tgtggctcaa acttctggcc tttggatttg     180
cccttctgga cacagaagtc tttgtcacag ggcaaacacc tacacccagt gatggtgcca     240
gcctcacaac tcttacacca tccactctgg gccttgcaag cactgaccct ccaagcacaa     300
ccatagctac cacaacgaag caaacatgtg ctgccatgtt tgggaacatt actgtgaatt     360
acacctatga atctagtaat cagactttta aggcagacct caaagatgtc caaaatgcta     420
agtgtggaaa tgaggattgt gaaaacgtgt taaataatct agaagaatgc tcacagataa     480
aaaacatcag tgtgtctaat gactcatgtg ctccagctac aactatagat ttatatgtac     540
caccagggac tgacaagttt tcgctacatg actgcacacc aaaagaaaag gctaatactt     600
caatttgttt ggagtggaaa acaaaaaacc ttgatttcag aaaatgcaac agtgacaata     660
tttcatatgt actccactgt gagccagaaa ataatacaaa atgcattaga agaaatacat     720
tcatacctga aagatgtcag ttggacaacc ttcgtgccca acaaattac acatgtgtag     780 cagaaatctt atatcgcggt gtaaaactcg tcaaaaatgt tataaatgtg cagacagatt     840
tggggattcc agaaacgcct aagcctagtt gtggggatcc agctgcaaga aaaacgttag     900
tctcttggcc tgagcctgta tctaaacctg agtctgcatc taaaccccat ggatatgttt     960
```

-continued

```
tatgctataa gaacaattca gaaaaatgta aaagtttgcc taataatgtg accagttttg    1020
aggtggaaag cttgaaacct tataaatact atgaagtgtc cctacttgcc tatgtcaatg    1080
ggaagattca agaaatggg actgctgaga agtgcaattt tcacacaaaa gcagatcgtc     1140
cggacaaggt caatggaatg aaaacctccc ggccgacaga caatagtata aatgttacat    1200
gtggtcctcc ttatgaaact aatggcccta aaaccttta cattttggta gtcagaagtg     1260
gaggttcttt tgttacaaaa tacaacaaga caaactgtca gttttatgta gataatctct    1320
actattcaac tgactatgag tttctggtct cttttcacaa tggagtgtac gagggagatt    1380
cagttataag aaatgagtca acaaattta atgctaaagc actgattata ttcctggtgt     1440
ttctgattat tgtgacatca atagccttgc ttgttgtttt gtataaaatc tatgatctgc    1500
gcaagaaaag atccagcaat ttagatgaac aacaggaact cgttgaaagg gatgatgaaa    1560
agcagctgat ggatgtggag ccaatccatt ctgacatttt gttggaaaca tacaaaagga    1620
agattgctga tgagggcaga ctgttcctgg ctgaatttca gagcattcca cgggtattca    1680
gcaagtttcc catcaaagat gcccgaaagc cccacaatca gaataaaaac cgttatgttg    1740
acattcttcc ctatgattat aaccgtgtgg aactctctga aataaatgga gatgcagggt    1800
ccacctacat aaatgccagc tacattgatg cttcaagga acccaggaaa tacattgctg     1860
cacaagggcc ccgggatgag acagttgatg acttctggag gatgatctgg gagcaaaagg    1920
ccacagttat tgtcatggtc acacgatgtg aagaaggaaa caggaacaag tgcgcagaat    1980
actggccaag catggaggaa ggcactcggg ctttcaaaga tattgttgtg acaatcaatg    2040
accacaaacg atgtcctgat tacatcattc agaagctgaa cgttgcacat aaaaaagaaa    2100
aagcaactgg aagagaagtg actcatatcc aattcaccag ctggccagac catggggttc    2160
ctgaagaccc tcacctgctc ctcaaacttc gacggagagt taatgctttt agcaacttct    2220
tcagtggtcc cattgtggtg cactgcagtg ctggtgttgg gcgtacaggt acctacattg    2280
gaattgatgc catgctggaa ggcctggaag cagagggcaa agtggatgtc tatggttatg    2340
ttgtcaagct aaggcgacag aggtgtctga tggtgcaagt ggaggcacag tatatcctga    2400
ttcatcaggc tttagtggaa tacaatcagt ttggagaaac agaagtgaac ttgtctgagt    2460
tacattcatg cctacacaac atgaagaaga gagatccacc cagtgacccc tcccctctgg    2520
aggctgaata ccagagactt ccttcataca ggagttggag gacacagcac attggaaatc    2580
aagaagaaaa taagaagaag aacaggaatt ctaatgttgt tccatatgac tttaacagag    2640
tgccacttaa gcatgaactg gagatgagca aagagagtga gcctgaatca gatgagtctt    2700
cagatgatga cagtgactca gaagaaacca gcaaatacat taatgcatcc tttgtgatga    2760
gttactggaa accagaaatg atgattgctg ctcaggggcc actaaaagaa acgatcggtg    2820
acttttggca gatgatattc caaagaaaag tcaaagttat tgtgatgttg acagagttag    2880
tgaatggaga ccaggaagtc tgtgctcagt actggggcga aggaaagcag acttatggag    2940
acatggaagt ggagatgaaa gacacaaaca gagcctcagc ctacactctc cgaacttttg    3000
agctgagaca ttccaagagg aaggagccca gaactgtgta ccagtaccag tgtaccacat    3060
ggaaagggga agagctgcct gcagaaccca agacctggt gtctatgatt caggacctca    3120
aacagaagct tcccaaggct tccccagaag ggatgaagta tcacaagcat gcatccatcc    3180
tcgtccactg cagagatgga tcccagcaga cagggttgtt ctgtgccttg ttcaatctct    3240
tggaaagtgc agaaacagaa gatgtggttg atgttttcca agtggtaaag tctctacgca    3300
aagcacggcc tgggtgtgtg tgcagctatg agcaatacca gttcctctat gacatcatcg    3360
```

```
ccagcatcta tcccgcccag aatggacaag tcaagaaaac aaacagccaa gacaaaattg      3420
aatttcataa tgaagtggat ggaggcaagc aggatgctaa ctgtgtccgt ccagatggtc      3480
ctctgaataa agcccaggaa gacagcagag gggtgggaac cccggagcct accaatagtg      3540
ctgaggaacc agaacatgct gccaatggtt ctgcgagccc agctccaacc cagagttcat      3600
aggaaaggag tcatgtggga caacgcagac tctcacatta gttctttcta tttttctaga      3660
cctaatgaaa gaacatggct gtgcagtggt ttatggaatc tgtgttcacc tttgccactg      3720
tataaaaata tttaagtttg tcaaaacatt ttgtacagtt ttatgcttat tttaaaagtg      3780
tatctatgtc attcagcagg aatgtatatg tgagagaggg tgtctgtgtg tgtgagagtg      3840
tgtttatgta tgagtgactg tgtgtgtgca tgtttgtgcg tgtgtatgac atctaaatgt      3900
gattggagaa tactttcaag ccatttcaaa tgctttcgag aaacagtgtg cctttctcc       3960 tcttgaggaa actatacatt ttatatctaa actgttaatt tgtttgaggg attaattttt      4020
taaaatccca ttgaaagtgg attcagttgt aagaataaca atgtgtacca ttctggaatg      4080
acctcaaggt gtcctccttg tcctgttgat gatcttgtag tttaagatgc tcttttga       4140 tatagataag cgtatgtaag agtgctgtgg gtgtgtacag ctgatctggg acgtgaacaa      4200
aatcaacatg tgagacttat gttccatata ctgtcatttc atcactatct cttaatgcat      4260
atttaatcaa acatgaaaat ctcaagggag actattttg tatccacatg ggaagtagaa       4320
cattgcaagt cagttgctgt ctacacaata gataaaaatt actagttaat gctcttggtc      4380
atatcgatat atgctatgaa cctaaataat tgcccttagc caaatataat gtatgttaaa      4440
aacacataga ataaaacag gggcatgaaa acttgtttgt actgaatatt tacataggta       4500
acctcgtaca gttagttctg ttatggaatt caccatttat gggaaatgta aaattgacta      4560
tggccatttc ctatgcttaa gaccatcttt gacttgcatt actgtgtatt tatcttgaat      4620
ttccccactg ttttgtttac tcttactgag atataatatt gataaccata taaactttc       4680 aactattatc ttctttgctt atgtggcgtg tgttacatgt ttgtaattga cagtgaagca      4740
atttcttctt caagctgaga ttggttttcc catttgttc attgatgaga aaatgaata        4800 attatcagat aggcgcatca gaaggggata aagaggactc tgttttctca ctagccactc      4860
acagatttct atctcatgtc atctgggaaa ggttctgttg ctctttgctg gaaaacattg      4920
tggaagtttg cagttctgat gctgatgtac cttcaggctg gttttttatgt tgatttgtga    4980 tttgtgattt gcttcagaat gctgatcatc ttcaatgata tcttttggaa cacagtttac      5040
ttagtagctg tttacttagc agcacatttg caacagcatc aaaagctatg ttactataaa      5100
atcagtgcgt gaagtctgat ttacattttg ctcaaggatc tgggtaaagt tttctaccaa      5160
gaatgttgag gactcatgaa aatgtgaagt tctccaactt ctaaaatttt ttaggacttt      5220
caataaacta taaattatt caaaatc                                           5247
```

<210> SEQ ID NO 341
<211> LENGTH: 5354
<212> TYPE: DNA
<213> ORGANISM: Macaca mulatta

<400> SEQUENCE: 341

```
atgaccatgt gtttgtggct taaacttttg gcatttgtct ttgcctttct ggacacagaa       60
gtatttgtga cagggcaagg ctcaacactt tcccccactg gctgtctgca agctgaggag      120
caaggaagcc aatcggagtc ccaaaacctc aaaagcaggg aagctgacag tgcagcctca      180
gtcagtggcc aaaggcctga gaaccctggc aaatcactgg agacggagaa cgacaaagat      240
```

-continued

```
gcccagtgtt ccactttcaa gtgacccctt acctactcac accactgcat tctcacccgc    300
aagcatctct gaaagagaaa atgacttctc agagaccaca ccatctctta gttcagacaa    360
tacttcaacc cacgtatccc cggactctt  ggataacgct agtgcttta atacgacagg     420 tgtttcatca gcactgacgc ctcaccttcc cacgcatgca gactcgcaga cgccctctac    480
tggaactgac acgcagacac ccagcggctc cgccgccaat accacactca gccctacccc    540
acgcagcaat gatatctcag atgtcccagg agagaggagt acagccagca cctttcctac    600
agacccaatt tccccattag caaccaccct catccctgca cgcaacagct ctgctgcctt    660
acctgcacgc acctccaaca ccaccatcac agcgaacacc tcagtttcct accttaatgc    720
ctctgaaaca accactccga gcccttctgg aagcactgtc atttcaaccc caacaatagc    780
tactactaca tctaagccaa catgtgctga aaaatatgca accatccctg tggattactt    840
atataacaac aaaactaaat tatttacagc aaagctaaat gttaatgaga atgtggaatg    900
tacaaacaat aatcacacac acaatatttg cacaaacaat gaggtgctta atcttccaga    960
atgtaaagaa atgaatgttt tcgtatctca taattcatgt acagatcgtc ataaagaatt    1020
aaaattagat gtgccaccag aggttgaaaa gtttcagtta gatgattgta caccggatgt    1080
agaagcaaat accactattt gtttaaaatg gaaaattatt gaaacctttg cttgtgataa    1140
aagtaaaatt acctacagat ttcaatgtgg taataaaaca tataataagg aaggcattta    1200
tttagaaaac cttgaacctg aatatgagta taagtgtgac tcagaaatac tctataataa    1260
ccacaagtat attaacataa ccaaacttat aaaaacagat tttgggattc caggacagcc    1320
tcagaatgtt gtttgtagac atgaagatgc acatcaagga gtaattaccc tggaatcccc    1380
tcaaagatca tttcataatt ttactctctg ttatgtaagc aagacagcaa aaaaatgcct    1440
cagtctggat aaacacctga caacatatca tttgcaaaat ttgaaacctt atacaaacta    1500
tagtttatca ttcatgcct  acatcattgc aaaagtgcaa cgtaatggaa ctgctgcaac    1560
atgtaatttc acaactgaaa gtgcacctcc aagccaggtc cagaacatga ttgtctccac    1620
atcagataat agtatgcgtg tcaagtgtga gggtcccagg gacgttaatg gccccactgg    1680
actttaccat ctggaagtcg aagctggaaa tactctagtt agaaatctgt cacaatctaa    1740
gtgcgatttc tctgtaaaca atcttcaata ttcaacatac tacaatctta aggtaaaagt    1800
atgctctcta cattactata gtaccaacat acatgataat gattgattca tattcatata    1860
tagcactccc tataattcta aggcactgat agcatttctg gcatttctga ttattgtgac    1920
atcaatagcc ctacttgttg ttctctataa aatctatgat ctacataaga aaagatcctg    1980
caatttggat gaacaacagg agcttgttga aagggatgat gaaaaacaac tgatgaatgt    2040
ggagccaatc catgcagata ttttgttgga aacttataag aggaagattg ctgatgaagg    2100
aagacttttt ctggctgaat tcagagcat  cccgcgggtg ttcagcaagt ttcctataaa    2160
ggaagctcga aagcccttta accagaataa aaaccgttat gttgacattc ttccttatga    2220
ttataaccgt gttgaactct ctgagataaa tggagatgca gggtcaaact acataaatgc    2280
cagctatatt gatggtttca agaacccag  gaaatacatt gctgcacaag gtcccaggga    2340
tgaaaccgtt gatgatttct ggaggatgat ttgggaacag aaagccacag ttattgtcat    2400
ggtcactcga tgtgaagaag aaacaggaa  caagtgtgca gaatactggc cgtcaatgga    2460
agagggcact cgggcttttg gagatgttgt tgtaaagatc aaccagcaca aagatgtcc     2520 agattacatc attcagaaat tgaacattgt aaataaaaaa gaaaagcaa  ctggaagaga    2580 ggtgactcac attcagttta ccagctggcc agaccacggg gtgcctgagg atcctcactt    2640
```

```
gctcctcaaa ctgagaagga gagtgaatgc cttcagcaat ttcttcagtg gtcccattgt   2700
ggtgcactgc agtgctggtg tcgggcgcac aggcacctat attggaattg atgccatgct   2760
agaaggcctg gaagctgaga acaaagtaga tgtttatggt tacgttgtca agctaaggcg   2820
acagagatgc ctgatggttc aagtagaggc ccagtacatc ttgatccatc aggctttggt   2880
tgaatacaat cagtttggag aaacagaagt gaatttgtct gaattacatc catatctaca   2940
taacatgaag aaaagggatc cacccagtga gccatctcca ctagaggctg aattccagag   3000
acttccttca tataggagct ggaggacaca gcacattgga aatcaggaag aaaataaaaa   3060
taaaaacagg aattctaatg tcatcccata tgactataac agagtgccac ttaaacatga   3120
gctggaaatg agtaaagaga gtgaccatga ttcagatgaa tcctctgatg atgacagtga   3180
ttcagaggaa ccaagcaaat acatcaatgc atctttata atgagctact ggaaacctga   3240
agtgatgatt gctgctcagg gaccactgaa ggagaccatt ggtgactttt ggcagatgat   3300
cttccaaaga aaagtcaaag ttattgttat gctgacagaa ctgaaacacg agaccagga   3360 aatctgtgct cagtactggg gagaaggaaa gcaaacatat ggagatatcg aagttgacat   3420
gaaagacaca aacaaatctt caacttacac ccttcgtgtc tttgaactga gacattccaa   3480
gaggaaagac tctcgaactg tgtaccagta ccaatataca aactggagtg tggagcagct   3540
tcctgcagaa cccaaggaat tagtctctct gattcaggtc ctcaaagaaa aacttcccca   3600
gaagaattcc tccgaaggga acaagcatca aagagtaca cctctcctca ttcactgcag   3660
ggatggatct cagcaaacgg gaatattttg tgctttgtta aatctcttag aaagtgcgga   3720
aacagaagag gtagtggata ttttcaagt ggtaaaagct ctacgcaaag ctaggcctgg   3780 catggttttcc acatttgagc aataccaatt cctatatgac atcattgcca gcacctaccc   3840
tgctcagaat ggacaagtaa agaaaaacaa ccatcaagaa gataaaattg aatttgataa   3900
tgaagtggaa aaagtaaagc aggatgctaa ttgtgttaat ccacttggtg ccacagaaaa   3960
gctccctgaa gcaaaggaac aggctacagg ttctgaaccc acaagtggca ctgaggggcc   4020
agaacattct gtcaatggtc ctgcaagtcc agctttaaat caaggttcat aggaaaagac   4080
ataaatgggg aaactccaaa cctcctgtta gctgttattt ctattttct agaagtagga   4140 agtgaaaata gtacagtg gattaattaa atgtattgaa ccaatatttg tggaagggtt   4200 ctatttact actgtggaaa aatatttaag atagttttgc cagaacagtt tgtacagacg   4260
tatgcttatt ttaaaatttt atttcttatt cagtaagaaa caacttctttt gtaacccttta   4320 catgtgtatg tatatgtgtg tatgcgtgtg tttgtgtgag agagaaagag aattctttca   4380
agtgaatcta aaagcttttg ctttgccttt tgtttttat caagaaaaaa tacattttat   4440
attagaagtg tttacttagc ttgaaggatc tgttttaaa atcataaact gtgtgcagac   4500 tataaatca tgtacatttc taaaatgacc tcaagatgtc ctccttgttc tactcatata   4560
tatcttatat atcttatata gttccagatt ttacttctag agatagtaca taaagtggt   4620 atgtgtgtgt atagctacta caaaacagtt aactaaatta acatttggaa atcttatat   4680 ccatatatta tcatttaatc caatatctttt ttaagcttat ttaattaaaa atttccagt   4740 gagcttatct ggctgtcttt acatggggtt tacaatttt tatcatctat tattccctgt   4800
acaatattta aaatttattg cttgatactt ttgaccacga attatgtttt gtacaattga   4860
acttaaataa acgtcattaa aataaaccaa tgcaatatgt attaatattc attgtataaa   4920 aataaaaaa tacaaatata tttgttaaat gtttacatat gaaatttaac atagctattt   4980
ttatggaatt tttcattgat atgaaaaata taatattgca tatgcatagg tctcatgtta   5040
```

```
ataccattc  ataactttca  ttaaagcatt  tactttgaac  ttctccaatg  cttagattct        5100
ttttaccggg aatggatatc  actaatcata  ataaaattca  acgattttt   tttcttgttt        5160 ataatacatt gtgttatatg  ttcaaatctg  aaatgtgtat  gcacctgttg  aaatatgttt        5220
aatgcagtta ttaacatttg  cagaacaatt  ttacaggccc  cagttatcca  atagtctaat        5280
aattgtttaa gatctagaaa  aaaatcaaga  atagtggtat  gtttcatgaa  gtaataaaaa        5340
ctcattttca tgaa                                                              5354
```